United States Patent
Nielsen et al.

(10) Patent No.: US 12,139,520 B2
(45) Date of Patent: Nov. 12, 2024

(54) $hAM_{15-52}$ ANALOGUES WITH IMPROVED AMYLIN RECEPTOR (hAMY3R) POTENCY

(71) Applicant: GUBRA A/S, Høsholm (DK)

(72) Inventors: Jens Christian Frøslev Nielsen, Høsholm (DK); Kristoffer Tobias Gustav Rigbolt, Høsholm (DK); Esben Matzen Bech, Høsholm (DK); Morten Lundh, Høsholm (DK); Paola Magotti, Høsholm (DK); Borja Ballarín-González, Høsholm (DK); Søren Ljungberg Pedersen, Borup (DK); Niels Vrang, Høsholm (DK)

(73) Assignee: GUBRA A/S, Hørsholm (DK)

( * ) Notice: Subject to any disclaimer, the term of this patent is extended or adjusted under 35 U.S.C. 154(b) by 0 days.

(21) Appl. No.: 18/024,879

(22) PCT Filed: Sep. 23, 2021

(86) PCT No.: PCT/EP2021/076250
§ 371 (c)(1),
(2) Date: Mar. 6, 2023

(87) PCT Pub. No.: WO2022/063925
PCT Pub. Date: Mar. 31, 2022

(65) Prior Publication Data
US 2024/0101634 A1 Mar. 28, 2024

(30) Foreign Application Priority Data
Sep. 24, 2020 (EP) .......... 20198117

(51) Int. Cl.
*C07K 14/575* (2006.01)
(52) U.S. Cl.
CPC .............. *C07K 14/575* (2013.01)
(58) Field of Classification Search
None
See application file for complete search history.

(56) References Cited

U.S. PATENT DOCUMENTS

| | | | | |
|---|---|---|---|---|
| 5,288,931 | A * | 2/1994 | Chang | C07K 1/1133 530/825 |
| 7,112,660 | B1 * | 9/2006 | Domingues | A61P 37/08 424/85.2 |
| 2003/0045474 | A1 * | 3/2003 | Sailer | A61K 38/1875 514/8.8 |
| 2009/0286723 | A1 | 11/2009 | Levy et al. | |
| 2013/0005646 | A1 | 1/2013 | Schaeffer | |
| 2014/0154743 | A1 * | 6/2014 | Levy | C07K 16/00 435/69.6 |
| 2016/0272693 | A1 | 9/2016 | Ramus et al. | |
| 2020/0115430 | A1 | 4/2020 | Blackwell | |
| 2020/0339649 | A1 | 10/2020 | Hsu | |

FOREIGN PATENT DOCUMENTS

WO 2015040182 3/2015

OTHER PUBLICATIONS

Tokuriki et al., 2009, Curr. Opin. Struc. Biol. 19:596-604).*
Fenton et al. (2020, Medicinal Chemistry Research 29:1133-1146).*
Bhattacharya et al. (2017, PLoS ONE 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Fischer Jan-Patrick et al, "The Impact of Adrenomedullin Thr22 on Selectivity within the Calcitonin Receptor-like Receptor/Receptor Activity-Modifying Protein System", DE, vol. 13, No. 17, doi:10.1002/cmdc.201800329, ISSN 1860-7179, (Jul. 31, 2018), pp. 1797-1805, ChemMedChem, URL: https://api.wiley.com/onlinelibrary/tdm/v1/articles/10.1002%2Fcmdc.201800329, XP055777098 [A] 1-14 abstract p. 1798, col. 2, lines 1-33 DOI: http://dx.doi.org/10.1002/cmdc.201800329.
S. D. Robinson et al, "Novel Peptide Antagonists of Adrenomedullin and Calcitonin Gene-Related Peptide Receptors: Identification, Pharmacological Characterization, and Interactions with Position 74 in Receptor Activity-Modifying Protein 1/3", Journal of Pharmacology and Experimental Therapeutics, (Nov. 1, 2009), vol. 331, No. 2, doi:10.1124/jpet.109.156448, ISSN 0022-3565, pp. 513-521, XP055058497 [A] 1-14 abstract figure 1 DOI: http://dx.doi.org/10.1124/jpet.109.156448.
Dalboege Louise S. et al, "2037-P: Characterization of Novel Unimolecular Amylin-Adrenomedullin Dual Agonists", Diabetes, US, (Jun. 4, 2019), vol. 68, No. Supplement 1, doi: 10.2337/db19-2037-P, ISSN 0012-1797, pp. 2037-P, XP055863394 [A] 1-14 the whole document DOI: http://dx.doi.org/10.2337/db19-2037-P.
Breiman, L., "Random Forests", Machine Learning, (20010000), vol. 45, No. 1, doi: 10.1023/A:1010933404324, pp. 5-32, XP019213368 DOI: http://dx.doi.org/10.1023/A:1010933404324.
A. Liaw and M. Wiener, "Classification and Regression by randomForest", R News, (20020000), vol. 2, No. 3, pp. 18-22, XP055305332.

(Continued)

*Primary Examiner* — Elizabeth C. Kemmerer
(74) *Attorney, Agent, or Firm* — DUANE MORRIS LLP; Gregory M. Lefkowitz; Brandon A. Chan

(57) ABSTRACT

The present invention relates to $hAM_{15-52}$ analogues with improved amylin receptor (hAMY3R) potency (hAMY3R-$EC_{50} \leq 250$ pM) and which are largely based on the sequence of the human adrenomedullin fragment $hAM_{15-52}$. The invention further relates to $hAM_{15-52}$ analogues that are selective amylin receptor (hAMY3R) agonists (hAMY3R-$EC_{50} \leq 250$ pM and an hAM1R-$EC_{50} \leq 25$ nM) and which are largely based on the sequence of the human adrenomedullin fragment $hAM_{15-52}$. The $hAM_{15-52}$ analogues according to the invention maintain the good physical stability of $hAM_{15-52}$. The invention further relates to pharmaceutical compositions comprising such polypeptides and their use in the treatment of a medical condition such as obesity, NASH and/or diabetes.

10 Claims, No Drawings
Specification includes a Sequence Listing.

(56) References Cited

OTHER PUBLICATIONS

Fischer Jan-Patrick et al, "The Impact of Adrenomedullin Thr22 on Selectivity within the Calcitonin Receptor-like Receptor/Receptor Activity-Modifying Protein System", DE, vol. 13, No. 17, doi:10.1002/cmdc.201800329, ISSN 1860-7179, (Jul. 2018), pp. 1797-1805, ChemMedChem, URL: https://api.wiley.com/onlinelibrary/tdm/v1/articles/10.1002%2Fcmdc.201800329, XP055777098 [A] 1-14 abstract p. 1798, col. 2, lines 1-33 DOI: http://dx.doi.org/10.1002/cmdc.201800329.

Chang, C.L., et al., "Development of chimeric and bifunctional antagonists for CLR/RAMP receptors," PLoS ONE, May 31, 2019, 14(5): e0216996; dps://doi.org/10.1371/journal.pone.0216996.

Hay, D.L., et al., "Update on the pharmacology of calcitonin/CGRP family of peptides: IUPHAR Review 25," British Journal of Pharmacol., Jan. 2018;175(1): 3-17; doi: 10.1111/bph.14075.

Mack, C.M., et al., "Davalintide (AC2307), a novel amylin-mimetic peptide: enhanced pharmacological properties over native amylin to reduce food intake and body weight," International Journal of Obesity, 2010, vol. 34; pp. 385-395.

Poyner, D.R., et al., "International Union of Pharmacology. XXXII. The mammalian calcitonin gene-related peptides, adrenomedullin, amylin, and calcitonin receptors." Pharmacol Rev., Jun. 2022;54(2): 233-46; doi: 10.1124/pr.54.2.233.

Coppock, H.A., et al., "Rat-2 fibroblasts express specific adrenomedullin receptors, but not calcitonin-gene-related-peptide receptors, which mediate increased intracellular cAMP and inhibit mitogen-activated protein kinase activity," Biochem J., 1999, 338, pp. 15-22.

Hinson, J.P., et al., "Adrenomedullin, a multifunctional regulatory peptide," Endocrine Reviews, 2000, 21(2): 138-67; doi: 10.1210/edrv.21.2.0396.

Bailey, R.J., et al., "Pharmacological characterization of rat amylin receptors: Implications for the identification of amylin receptor subtypes," British Journal of Pharmacol., 2012, 166(1): 151-67. doi: 10.1111/j.1476-5381.2011.01717.x.

Hay, D.L., et al., "Amylin: Pharmacology, Physiology, and Clinical Potential," Pharmacol Rev., 2015, 67(3): 564-600. doi: 10.1124/pr.115.010629.

Fischer, J.P., et al., "Adrenomedullin—Current perspective on a peptide hormone with significant therapeutic potential," Peptides, 2020, 131:170347. doi: 10.1016/j.peptides.2020.170347.

Schönauer, R., et al., "Adrenomedullin 2.0: Adjusting Key Levers for Metabolic Stability," J Med Chem., 2016, 23;59(12): 5695-705. doi: 10.1021/acs.jmedchem.6b00126. Epub Jun. 6, 2016. PMID: 27166982.

\* cited by examiner hAM$_{15-52}$ ANALOGUES WITH IMPROVED AMYLIN RECEPTOR (hAMY3R) POTENCY

CROSS-REFERENCE TO RELATED APPLICATIONS

This application is a § 371 national stage entry of International Application No. PCT/EP2021/076250 filed Sep. 23, 2021, based on priority European Patent Application No. 20198117.2, filed Sep. 24, 2020, the entire contents of which are incorporated herein by reference.

FIELD OF THE INVENTION

The present invention relates to hAM$_{15-52}$ analogues with improved amylin receptor (hAMY3R) potency (hAMY3R-EC$_{50}$≤250 pM) and which are largely based on the sequence of the human adrenomedullin fragment hAM$_{15-52}$. The invention further relates to hAM$_{15-52}$ analogues that are selective amylin receptor (hAMY3R) agonists (hAMY3R-EC$_{50}$≤250 pM and an hAM1R-EC$_{50}$≤25 nM). In particularly, the present invention is based on the realization that the human adrenomedullin fragment hAM$_{15-52}$ may be converted into highly selective amylin receptor agonists (hAMY3R-EC$_{50}$≤250 pM and an hAM1R-EC$_{50}$≤25 nM) by replacing the amino acid in position X$_{11}$ in hAM$_{15-52}$ together with one or more of the amino acids in the positions X$_4$, X$_{37}$ and/or X$_{38}$ in hAM$_{15-52}$. Thus, replacing at least two amino acids on hAM$_{15-52}$ resulted in hAM$_{15-52}$ analogues with AMY3R and AM1R potencies comparable to hAMY$_{1-37}$ (amylin). The invention further relates to pharmaceutical compositions comprising such hAM$_{15-52}$ analogues and their medical use in the treatment of a medical condition, such as obesity and/or diabetes.

SEQUENCE LISTING

The instant application contains a Sequence Listing which has been filed electronically in ASCII format and is hereby incorporated by reference in its entirety. Said ASCII copy, created on May 29, 2024, is named G3075-02705_ST25 and is 216,301 bytes in size.

BACKGROUND OF THE INVENTION

Obesity is a medical condition in which excess body fat has accumulated to the extent that it has a negative impact on health. It is affecting a huge number of individuals worldwide and increasing rapidly in certain parts of the world. The World Health Organisation (WHO) estimated that in 2016, approximately 650 million people were obese worldwide. Obesity is defined as a body mass index (BMI) above 30. Obesity is considered a major risk factor for developing a variety of medical conditions, such as cardiovascular diseases (e.g. hypertension, atherosclerosis, heart attacks or stroke), NASH musculoskeletal disorders, certain kinds of cancers, depression and diabetes type II, and hence is detrimental to human health. Cardiovascular diseases and diabetes are two main diseases associated with obesity. A large amount of research has been conducted in the obesity field in search for new treatments for obesity or obesity-related diseases and disorders.

Diabetes is a group of metabolic disorders characterized by a high blood sugar level. As of 2019, the International Diabetes Federation estimated that 463 million people are suffering from diabetes worldwide, approximately half of the individuals being diagnosed. Diabetes is divided into two types, namely type I and type II diabetes. Type I diabetes results from the pancreas's failure to produce enough insulin due to loss of beta cells caused by an autoimmune response. On the other hand, type II diabetes is a condition that begins with insulin resistance in which cells fail to respond to insulin properly and as the disease progresses may also result in a lack of insulin.

Human amylin (hAMY$_{1-37}$ or amylin) is a 37-residues peptide hormone that is co-secreted with insulin from the pancreatic β-cells with the amino acid sequence Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO: 2) with a disulphide bridge between residues 2 and 7. Amylin suppresses glucagon release and inhibits gastric emptying and hence plays an important role in maintaining glucose homeostasis by decreasing the blood sugar concentration. Therefore, amylin is a potential candidate for treating diabetes. Furthermore, amylin has been shown to reduce food intake and plays an important role in satiety, also making it a potential candidate for treating obesity. However, amylin possesses some drawbacks such as a high tendency of fibrillation, a short in vivo half-life, and chemical instability at pH 7. Thus, native amylin is suboptimal for use as a pharmaceutically active ingredient.

A large number of amylin derivatives are known in the prior art, such as the ones disclosed in WO2016/146739. These amylin analogues attempt to solve some of the known drawbacks that human amylin possesses. One successful example is the amylin analogue Pramlintide, which has been approved by the FDA for use in type I and type II diabetes. However, Pramlintide is formulated at pH 4 as it fibrillates at pH 7. Thus, there is still a need for new amylin analogues with increased chemical stability, increased metabolic stability, and/or a reduced tendency for fibrillation. In particular, amylin analogues that are stable over a broader pH range are desirable. Furthermore, there is a need for new amylin analogues with increased effectiveness through e.g. increased potency, higher efficacy, and/or longer half-lives to allow less frequent dosing and increased patient compliance. The present invention sets out to solve one or more of the problems known from the prior art by applying a new chemical strategy.

SUMMARY OF THE INVENTION

In a first aspect, the present invention relates to hAM$_{15-52}$ analogues with improved amylin receptor (hAMY3R) potency (hAMY3R-EC$_{50}$≤250 pM). Thus, in a first aspect the invention relates to hAM$_{15-52}$ analogues or a pharmaceutically acceptable salt thereof comprising 38 amino acids (X$_1$-X$_{38}$), wherein the amino acid in position X$_{11}$ is selected from R, W or Cit and wherein the hAM$_{15-52}$ analogue has at least 50% homology to hAM$_{15-52}$ (SEQ ID NO: 1), such as at least 60% homology to hAM$_{15-52}$ (SEQ ID NO: 1). The inventors surprisingly found that the amino acid position X$_{11}$ was highly important for increasing amylin receptor potency of hAM$_{15-52}$. Thus, a single substitution in X$_{11}$ from K to R, W or Cit was enough to improve the amylin receptor potency (hAMY3R-EC$_{50}$≤250 pM) of hAM$_{15-52}$ significantly while retaining adrenomedullin potency (hAM1R).

In a second aspect, the present invention provides selective hAM$_{15-52}$ analogues (hAMY3R-EC$_{50}$≤250 pM and an hAM1R-EC$_{50}$≥25 nM), which act as agonists on the amylin receptor hAMY3R but which, unlike in the prior art (e.g. WO2016/146739), are derived from the backbone of the adrenomedullin fragment hAM$_{15-52}$. The inventors surprisingly found that each of the positions $X_4$, $X_{37}$ and $X_{38}$ were highly important for the hAM1R potency of hAM$_{15-52}$ and that hAM1R potency of hAM$_{15-52}$ could be abolished or reduced (hAM1R-EC$_{50}$≥25 nM) by certain amino acid substitutions in either of the positions $X_4$, $X_{37}$ and/or $X_{38}$. Thus, in a second aspect, the invention relates to hAM$_{15-52}$ analogues comprising 38 amino acids ($X_1$-$X_{38}$) or a pharmaceutically acceptable salt thereof, wherein the amino acid in position $X_{11}$ is selected from R, W or Cit and wherein the hAM$_{15-52}$ analogue has at least 50% homology to hAM$_{15-52}$ (SEQ ID NO: 1), such as at least 60% homology to hAM$_{15-52}$ (SEQ ID NO: 1) and further wherein $X_4$ is selected as F, Y, W, T, M, I, A or C; $X_{37}$ is selected as G, Y, S, W, T, Q, P, M, I, H, F, E, A, R, C or K; $X_{38}$ is selected as Hyp, Y, W, T, Q, P, M, I, H, F, E, A, R, or K, with the proviso that at least one of the positions $X_4$, $X_{37}$ or $X_{38}$ is not the amino acid present in hAM$_{15-52}$ (SEQ ID NO: 1) in said position. The inventors surprisingly found that the human adrenomedullin fragment hAM$_{15-52}$ may be converted into highly selective amylin receptor agonists (hAMY3R-EC$_{50}$ value≤250 pM and an hAM1R-EC$_{50}$≥25 nM) by replacing the amino acid in position $X_{11}$ in hAM$_{15-52}$ together with one or more of the amino acids in the positions $X_4$, $X_{37}$ and/or $X_{38}$ in hAM$_{15-52}$. Thus, replacing at least two amino acids on hAM$_{15-52}$ resulted in hAM$_{15-52}$ analogues with hAMY3R and hAM1R potencies comparable to amylin rather than hAM$_{15-52}$. One benefit of this approach is that unlike human amylin, hAM$_{15-52}$ is not prone to fibrillation, and by using this new chemical strategy, the inventors further envisaged that the good fibrillation properties of hAM$_{15-52}$ could be maintained in the new hAM$_{15-52}$ analogues. Therefore, the hAM$_{15-52}$ analogues according to the invention comprise a significant part of the backbone present in hAM$_{15-52}$ as an important part of the sequence (i.e. at least least 50% homology to hAM$_{15-52}$ (SEQ ID NO: 1)). Thus, in the second aspect of the invention, the first problem solved is the provision of new potent hAMY3R agonists with high selectivity over hAM1R, which are obtained by tweaking the polypharmacology of the hAM$_{15-52}$ fragment into hAMY3R agonism. The second problem solved by the second aspect is the provision of new hAMY3R agonists which are less prone to fibrillation, thereby overcoming a problem inherent to human amylin. Unlike the amylin derivatives known from the prior art, the hAM$_{15-52}$ analogues of the present invention possess a structurally distinct sequence belonging to the hAM$_{15-52}$ fragment. Thus, the hAM$_{15-52}$ analogues of the invention possess different physical-chemical properties compared to the amylin derivatives in the prior art, such as different solubility, chemical-, physical-, and/or metabolic stability.

In a third aspect, the invention relates to hAM$_{15-52}$ analogues according to the first and/or second aspect for use as a medicament. More particularly, the third aspect of the invention relates to hAM$_{15-52}$ analogues according to the first and/or second aspect for use in treating, preventing or ameliorating a variety of diseases, disorders or conditions, such as but not limited to excess food intake, excess body weight, obesity, Binge eating disorder, Prader-Willi syndrome, dyslipidemia, metabolic diseases/disorders, diabetes I or II, impaired glucose tolerance, insulin resistance syndrome and/or NASH.

In a fourth aspect, the invention relates to pharmaceutical compositions comprising one or more of the hAM$_{15-52}$ analogues according to the first and/or second aspect and their medical use(s) in treating, preventing, or ameliorating a variety of diseases, disorders or conditions according to the third aspect. The pharmaceutical compositions may comprise a pharmaceutically acceptable carrier (vehicle) and/or one or more excipient(s).

In a fifth aspect, the invention relates to a method of treating a human or animal subject with one or more hAM$_{15-52}$ analogue(s) according to the first and/or second aspect, wherein the human or animal subject is diagnosed with or suffering from one or more of the diseases, disorders or conditions, such as but not limited to excess food intake, excess body weight, obesity, Binge eating disorder, Prader-Willi syndrome, dyslipidemia, metabolic diseases/disorders, diabetes I or II, impaired glucose tolerance, insulin resistance syndrome and/or NASH, preferably obesity, diabetes I or II and/or NASH.

The invention will now be explained in more detail from the alignment of the amylin (hAMY$_{1-37}$) and the adrenomedullin fragment (hAM$_{15-52}$) as shown in Table 1 below.

Definitions

In the present context, when the disclosure refers to positions of amino acids in the hAM$_{15-52}$ analogues (i.e. $X_1$-$X_{38}$) that are derived/selected from hAMY$_{1-37}$ or retained/selected from the hAM$_{15-52}$ fragment, the following alignment shown in Table 1 applies. Thus, position $X_1$ in the hAM$_{15-52}$ analogues according to the invention corresponds to the first amino acid in human amylin (hAMY$_{1-37}$) and amino acid number 15 (hAM$_{15}$) in the hAM$_{15-52}$ fragment.

TABLE 1

| Position $X_{1-38}$ SEQ ID NO: 1 | | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| hAM$_{15-52}$ | G | C | R | F | G | T | C | T | V | Q | K | L | A | H | Q | I | Y | Q | F |
| hAMY$_{1-37}$ | K | C | N | T | A | T | C | A | T | Q | R | L | A | N | F | L | V | H | S |

| Position $X_{1-38}$ SEQ ID NO: 2 | | | | | | | | | | | | | | | | | | |
|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| hAM$_{15-52}$ | T | D | K | D | K | D | N | V | A | P | R | S | K | I | S | P | Q | G | Y |
| hAMY$_{1-37}$ | S | N | N | F | - | G | A | I | L | S | S | T | N | V | G | S | N | T | Y |

According to the present invention, the hAM$_{15-52}$ analogues are generally amidated at the C-terminal (—CONH$_2$), like the native peptides; amylin and adrenomedullin. However, the hAM$_{15-52}$ analogues of the present invention may also have either a free carboxylic acid (—COOH) or another post-translational modification such as a methyl ester (—COOMe). In a highly preferred embodiment of the invention, the $hAM_{15-52}$ analogues are amidated at the C-terminal. The $hAM_{15-52}$ analogues according to the present invention may have a free amine (—$NH_2$), be N-acylated (—NHCOR), N-methylated (—$NHCH_3$ or —$N(CH_3)_2$) or deaminated at the N-terminal. The $hAM_{15-52}$ analogues may also be lipidated, e.g. at the N-terminal as exemplified herein, depending on the desired half-life of the polypeptides.

According to the present invention, lipidation has the usual meaning in the art. Thus, lipidation in the present context refers to the covalent attachment of a lipid optionally through a linker to $hAM_{15-52}$ analogues of the invention. Lipidation is typically performed to improve the pharmacokinetic profile of a polypeptide by e.g. improving metabolic stability, reducing enzymatic degradation, lowering excretion and metabolism, all in all resulting in a prolonged in vivo half-life ($t_{1/2}$) of the $hAM_{15-52}$ analogues. The $hAM_{15-52}$ analogues according to the invention may be lipidated or non-lipidated. The lipidated $hAM_{15-52}$ analogues exemplified herein are lipidated with a saturated $C_{20}$-diacid through various linkers as shown in table 2.

According to the present invention, the abbreviations Hyp, Cit, Aib, Aad, (NMe)G/Sar, (NMe)I have the usual meaning in the art. Thus, Hyp refers to L-hydroxyproline, Cit refers to L-citrulline, Aib refers to 2-aminoisobutyric acid, Aad refers to L-homoglutamic acid, (NMe)G refers to N-methylglycine also known as Sar or sarcosine and (NMe)I refer to N-methyl-L-isoleucine.

According to the present invention, $EC_{50}$ values are used as a measure of agonist potency at a given receptor. An $EC_{50}$ value is a measure of the concentration of a compound required to achieve half of that compound's maximal activity in a particular assay. Thus, an $hAM_{15-52}$ analogue according to the invention having an $hAMY3R-EC_{50}$ lower than the $hAMY3R-EC_{50}$ of $hAM_{15-52}$ in the given assay is considered to have higher potency or activity at the hAMY3R receptor than the adrenomedullin fragment $hAM_{15-52}$. Likewise, an $hAM_{15-52}$ analogue according to the invention having an $hAM1R-EC_{50}$ higher than the $hAM1R-EC_{50}$ of $hAM_{15-52}$, in the given assay may be considered to have lower potency or activity at the hAM1R receptor than the adrenomedullin fragment $hAM_{15-52}$.

According to the present invention, an $hAM_{15-52}$ analogue or derivative thereof may be in the form of a pharmaceutically acceptable salt. Thus, pharmaceutically acceptable salts are intended to include any salts that are commonly used in formulations of peptides. Such salts include both acid addition salts and basic salts, and examples may be found e.g. in Remington's Pharmaceutical Sciences, $17^{th}$ edition. Likewise, various solvates of the $hAM_{15-52}$ analogues or pharmaceutically acceptable salts thereof are also within the scope of the invention.

According to the present invention, $hAM_{15-52}$ analogues are short chains of amino acids that have been linked by amide bonds. In the most preferred embodiment of the invention, the $hAM_{15-52}$ analogues are 38 amino acids in length, not including any amino acids that function as spacers between an optional lipid and the hybrid polypeptides.

In the present context, unless otherwise stated, the amino acids are all L-amino acids (L-stereoisomer, natural amino acids). Thus, the absolute configuration of the amino acids is the (S)-configuration with the exception of L-cysteine and L-selenocysteine having the (R)-configuration.

In the present context, it should be understood that the amino acid Cys ($X_2$) and Cys ($X_7$) in the $hAM_{15-52}$ analogues are covalently connected by a bridge, preferably a disulfide bridge (—S—S—) such as present in $hAMY_{1-37}$ and $hAM_{15-52}$. The cyclization of the disulfide bridge may be performed after purification of the hybrid polypeptides or prior to cleavage from the resin in the solid-phase peptide synthesis, optionally in the presence of suitable protecting groups. The disulfide bridge may be formed spontaneously by stirring the hybrid polypeptide in the presence of oxygen or may be formed by treating the hybrid polypeptides with another suitable oxidant such as iodine ($I_2$), optionally in the presence of a base.

In the present context, the $hAM_{15-52}$ analogues or derivatives thereof according to the first or second aspect have an hAMY3R potency ($EC_{50}$)≤250 pM, such as 200 pM, preferably an $hAMY3R-EC_{50}$≤150 pM, such as ≤125 pM, more preferably an $hAMY3R-EC_{50}$≤100 pM, such as 75 pM, yet more preferably an $hAMY3R-EC_{50}$≤50 pM, such as ≤25 pM, most preferably an $hAMY3R-EC_{50}$≤15 pM, such as ≤10 pM. Thus, the most hAMY3R potent $hAM_{15-52}$ analogues may be more or less equipotent with native human amylin $hAMY_{1-37}$. For example, SEQ ID NOs: 3-44 have an $hAMY3R-EC_{50}$ between 6.0-10 pM and are thus more or equipotent compared to $hAMY_{1-37}$ ($hAMY3R-EC_{50}$=10 pM) when measured under the same assay conditions.

In the present context, the $hAM_{15-52}$ analogues or derivatives thereof according to the second aspect have an abolished or reduced $EC_{50}$ when the $EC_{50}$ value on hAM1R≥25 nM, such as $EC_{50}$ value on hAM1R≥50 nM, such as an $hAM1R-EC_{50}$≤100 nM, preferably an $hAM1R-EC_{50}$≤150 nM, such as ≥200 nM, more preferably $hAM1R-EC_{50}$≥250 nM, such as ≥300 nM, even more preferably an $hAM1R-EC_{50}$≥350 nM, such as ≥400 nM, yet more preferably an $hAM1R-EC_{50}$≥450 nM, such as ≥500 nM, yet more preferably an $hAM1R-EC_{50}$≤600 nM, such as ≥700 nM, yet more preferably an $hAM1R-EC_{50}$≥800 nM, such as ≥900 nM, yet more preferably an $hAM1R-EC_{50}$≤1000 nM, most preferably an $hAM1R-EC_{50}$≤5000 nM. Thus, in the present context, selectively in terms of potency towards the amylin receptor hAMY3R over the adrenomedullin receptor hAM1R (i.e. a selective amylin receptor agonist) should be understood as an $hAM_{15-52}$ analogue or a derivative thereof according to the second aspect having an $hAMY3R-EC_{50}$ value≤250 pM and an $hAM1R-EC_{50}$≤25 nM. Thus, a selective $hAM_{15-52}$ analogue or a derivative thereof has a selectivity ratio ($hAM1R\ EC_{50}/hAMY3R\ EC_{50}$) of at least 100. Preferably, the $hAM_{15-52}$ analogues or derivatives thereof have an $hAMY3R-EC_{50}$ value≤250 pM and an $hAM1R-EC_{50}$≤50 nM and thus a selectivity ratio ($hAM1R\ EC_{50}/hAMY3R\ EC_{50}$)≥200. More preferably, the $hAM_{15-52}$ analogues or derivatives thereof have an $hAMY3R-EC_{50}$≤200 pM, an $hAM1R-EC_{50}$≤100 nM and thus a selectivity ratio ($hAM1R\ EC_{50}/hAMY3R\ EC_{50}$)≥500. More preferably, an $hAM_{15-52}$ analogue or a derivative thereof has an $hAMY3R-EC_{50}$≤125 pM, an $hAM1R-EC_{50}$≥200 nM and thus a selectivity ratio ($hAM1R\ EC_{50}/hAMY3R\ EC_{50}$)≥1600. Even more preferably, the $hAM_{15-52}$ analogue or a derivative thereof has an $hAMY3R-EC_{50}$≤100 pM, an $hAM1R-EC_{50}$≥500 nM and thus a selectivity ratio ($hAM1R\ EC_{50}/hAMY3R\ EC_{50}$)≥5000. Most preferably, the $hAM_{15-52}$ analogue or a derivative thereof has an $hAMY3R-EC_{50}$≤50 pM, an $hAM1R-EC_{50}$≥1000 nM and thus a selectivity ratio ($hAM1R\ EC_{50}/hAMY3R\ EC_{50}$)≥20000. For example, any of SEQ ID NOs: 3-42 have a selectivity ratio of at least 6000 and most of them much higher.

A person skilled in the art is well aware that $EC_{50}$ values depend on the assay type and assay conditions. Thus, in the present context when the disclosure refers to an $EC_{50}$ value, it should be understood as an $EC_{50}$ value obtained when measured according to the procedure described in the examples under general protocols for cAMP assays for measuring in vitro receptor activation. However, variation may also be present within the same assay under apparently identical assay conditions due to variation in e.g. receptor expression in the cells (i.e. receptor density). Thus, in order to compare $EC_{50}$ values, $hAMY_{1-37}$ (SEQ ID NO: 2) and $hAM_{15-52}$ (SEQ ID NO: 1) have been tested as internal standards for comparison between different assay runs or even different assays. The hAMY3R-$EC_{50}$ and the hAM1R-$EC_{50}$ of $hAMY_{1-37}$ (SEQ ID NO: 2) was determined to 10 pM and 5000 nM, respectively, using the same assay conditions and cell line as the $hAM_{15-52}$ analogues (SEQ ID NO: 3-392). Likewise, the hAMY3R-$EC_{50}$ and the hAM1R-$EC_{50}$ of the $hAM_{15-52}$ (SEQ ID NO: 1) was determined to 1.3 nM and 1.1 nM, respectively, using the same assay conditions and cell line as the $hAM_{15-52}$ analogues (SEQ ID NO: 3-392). Thus, it follows that the $hAM_{15-52}$ analogues or derivatives thereof according to the first or second aspect have a relative hAMY3R-$EC_{50}$ ratio (hAMY3R-$EC_{50}$)/(h$AMY_{1-37}$-hAMY3R-$EC_{50}$)≤(250 pM)/(10 pM)≤25. Preferably, the relative hAMY3R-$EC_{50}$ ratio (hAMY3R-$EC_{50}$)/(h$AMY_{1-37}$-hAMY3R-$EC_{50}$)≤20. More preferably, the relative hAMY3R-$EC_{50}$ ratio (hAMY3R-$EC_{50}$)/(h$AMY_{1-37}$-hAMY3R-$EC_{50}$)≤12.5. Even more preferably, the relative hAMY3R-$EC_{50}$ ratio (hAMY3R-$EC_{50}$)/(h$AMY_{1-37}$-hAMY3R-$EC_{50}$)≤10. Even more preferably, the relative hAMY3R-$EC_{50}$ ratio (hAMY3R-$EC_{50}$)/(h$AMY_{1-37}$-hAMY3R-$EC_{50}$)≤5. Yet more preferably, the relative hAMY3R-$EC_{50}$ ratio (hAMY3R-$EC_{50}$)/(h$AMY_{1-37}$-hAMY3R-$EC_{50}$)≤2. Most preferably, the relative hAMY3R-$EC_{50}$ ratio (hAMY3R-$EC_{50}$)/(h$AMY_{1-37}$-AMY3R-$EC_{50}$)≤1 such that the $hAM_{15-52}$ analogues or derivatives thereof an equipotent or more potent than $hAMY_{1-37}$. Likewise, the selective $hAM_{15-52}$ analogues or derivatives thereof according to the second aspect have a relative hAMY3R-$EC_{50}$ ratio (hAMY3R-$EC_{50}$)/(h$AM_{15-52}$-AMY3R-$EC_{50}$)≤(250 pM)/(1300 pM)≤0.19 and a relative hAM1R-$EC_{50}$ ratio (hAM1R-$EC_{50}$)/(h$AM_{15-52}$-hAM1R-$EC_{50}$)≤(25 nM)/(1.1 nM)≤22.7. Preferably, the relative hAMY3R-$EC_{50}$ ratio (hAMY3R-$EC_{50}$)/(h$AM_{15-52}$-hAMY3R-$EC_{50}$)≤(250 pM)/(1300 pM)≤0.19 and a relative hAM1R-$EC_{50}$ ratio (hAM1R-$EC_{50}$)/(h$AM_{15-52}$-hAM1R-$EC_{50}$)≥(50 nM)/(1.1 nM)≥45.5. More preferably, the relative hAMY3R-$EC_{50}$ ratio (hAMY3R-$EC_{50}$)/(h$AM_{15-52}$-hAMY3R-$EC_{50}$)≤0.15 and a relative hAM1R-$EC_{50}$ ratio (hAM1R-$EC_{50}$)/(h$AM_{15-52}$-hAM1R-$EC_{50}$)≥76.9. Yet more preferably, the relative hAMY3R-$EC_{50}$ ratio (hAMY3R-$EC_{50}$)/(h$AM_{15-52}$-hAMY3R-$EC_{50}$)≤0.096 and a relative hAM1R-$EC_{50}$ ratio (hAM1R-$EC_{50}$)/(h$AM_{15-52}$-hAM1R-$EC_{50}$)≥154. Even more preferably, the relative hAMY3R-$EC_{50}$ ratio (hAMY3R-$EC_{50}$)/(h$AM_{15-52}$-hAMY3R-$EC_{50}$)≤0.077 and a relative hAM1R-$EC_{50}$ ratio (hAM1R-$EC_{50}$)/(h$AM_{15-52}$-hAM1R-$EC_{50}$)≥384. Yet more preferably, the relative hAMY3R-$EC_{50}$ ratio (hAMY3R-$EC_{50}$)/(h$AM_{15-52}$-AMY3R-$EC_{50}$)≤0.038 and a relative hAM1R-$EC_{50}$ ratio (hAM1R-$EC_{50}$)/(h$AM_{15-52}$-hAM1R-$EC_{50}$)≥769. Most preferably, the relative hAM1R-$EC_{50}$ ratio (hAM1R-$EC_{50}$)/(h$AM_{15-52}$-hAM1R-$EC_{50}$)≥2000.

According to the present invention, the term "treatment" should be understood in the broadest sense as prevention, amelioration, or treatment. Thus, treatment is also intended to include prophylactic treatment.

According to the present invention, from the aspect(s)/embodiment(s) which refer to "wherein $hAM_{15-52}$ analogue has (e.g.) at least 50% homology to $hAM_{15-52}$ (SEQ ID NO: 1)" or "a derivative thereof with (e.g.) at least 50% homology to $hAM_{15-52}$", it should be understood that the $hAM_{15-52}$ analogue or derivative thereof has at least 50% sequence identity with $hAM_{15-52}$ (SEQ ID NO: 1) when aligned. As an example, SEQ ID NO: 169 illustrated below differs in two amino acids ($X_{11}$ and $X_{38}$) from $hAM_{15-52}$ (SEQ ID NO: 1) and thus has (38−2)/38=94.7% sequence identity to $hAM_{15-52}$ (SEQ ID NO: 1).

```
SEQ ID NO: 1    G C R F G T C T V Q K L A H Q I Y Q F T D K D K D N V A P R S K I S P Q G Y

Derivative X:   G C R F G T C T V Q R L A H Q I Y Q F T D K D K D N V A P R S K I S P Q G Hyp
SEQ ID NO: 169
```

DETAILED DESCRIPTION OF THE INVENTION

The Calcitonin Peptide Family

The calcitonin family of peptides consists of the hormone peptides calcitonin (CT), calcitonin gene-related peptide (CGRP), islet amyloid polypeptide (IAPP, amylin or $hAMY_{1-37}$), and adrenomedullin (hAM) as well as their precursors. $hAMY_{1-37}$ is a 37-residues peptide hormone that is co-secreted with insulin from the pancreatic β-cells with the amino acid sequence Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO: 2). Amylin supresses glucagon release and inhibits gastric emptying and hence plays an important role in maintaining glucose homeostasis by decreasing the blood sugar concentration. Furthermore, amylin has shown to reduce food intake and plays an important role in satiety, making it a potential candidate for treating e.g. obesity and/or diabetes. hAM is a 52-residues peptide hormone expressed in all tissues with the amino acid sequence Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO: 393). It is a potent vasodilator and has shown positive influence in cardiovascular diseases, such as myocardial infarction, limb ischemia and hypertension.

The biological activity of the calcitonin protein family is generally mediated via binding to the calcitonin receptor (CTR) and the calcitonin receptor like receptor (CRLR), both belonging to family 2 of the G-protein-coupled receptors (GPCR). These receptors may be co-expressed in combination with different receptor modifying proteins (RAMP1-3) generating functional receptors for the individual peptides in the calcitonin protein family. Co-expression of CTR with RAMP1 leads to formation of a receptor for amylin and CGRP (AMY1R), co-expression of CTR with RAMP2 leads to the amylin receptor 2 (AMY2R) and co-expression of CTR with RAMP3 leads to the amylin receptor (AMY3R). Co-expression of CRLR with RAMP1 leads to a formation of a receptor for CGRP (CGRP1R), co-expression of CRLR with RAMP2 leads to a formation of a receptor for adrenomedullin (AM1R) and co-expression of CRLR with RAMP3 leads to a formation of a receptor for adrenomedullin and CGRP (AM2R).

Several of the native peptides in the calcitonin protein family show considerable overlap in pharmacology between receptors. For example, adrenomedullin is approximately 100 times less potent on AMY3R compared to $hAMY_{1-37}$. The adrenomedullin fragment ($hAM_{15-52}$) is almost equipotent on AMY3R and AM1R with an $EC_{50}$ of 1.3 nM on AMY3R and an $EC_{50}$ value of 1.1 nM on AM1R (said $EC_{50}$ value being measured according to the examples herein). $hAMY_{1-37}$ on the other hand has an $EC_{50}$ value of 10 pM on AMY3R while being inactive on AM1R.

Determination of Important Amino Acid Positons in $hAM_{15-52}$

The inventors initially hypothesized that since $hAM_{15-52}$ and $hAMY_{1-37}$ belong to the same family of hormones, the Calcitonin/CGRP/IAPP family, the AMY3R potency of $hAM_{15-52}$ could be improved or even converted into selective AMY3R agonism over hAM1R agonism, by substituting certain amino acids in $hAM_{15-52}$ with amino acids derived from $hAMY_{1-37}$, thereby overcoming some of the drawbacks that are inherent to $hAMY_{1-37}$. All 37 $hAMY_{1-37}$ amino acids were systematically substituted into the $hAM_{15-52}$. Furthermore, $X_{38}$ was selected as Hyp (Hydroxyproline), which is neither present in $hAMY_{1-37}$ nor in $hAM_{15-52}$. The inventors constructed random forest models (Breiman, L. (2001), Random Forests, Machine Learning 45(1), 5-32.) describing the relationship between peptides sequence and hAMY3R and the hAM1R potency, respectively, and systematically synthesised and screened peptide sequences. For each $hAM_{15-52}$ analogue, the amino acid in each sequence position were used as features, and receptor $EC_{50}$ values were used as response to construct the models. The "randomForest" package implemented in the statistical programming language R was used to calculate the importance of each position and the most important positions were identified to be critical for hAMY3R and/or hAM1R activity (A. Liaw and M. Wiener (2002). Classification and Regression by randomForest. R News 2(3), 18-22.). Based on this systematic analysis the inventors identified $X_4$, $X_{37}$ and $X_{38}$ to be important for hAM1R activity, while of less importance for hAMY3R activity. The inventors identified $X_{11}$ to be critical for hAMY3R activity, while of less importance for hAM1R activity. Finally, the inventors identified $X_{17}$ to be of some importance for hAMY3R activity, while of less importance for hAM1R activity. Thus, the inventors identified $X_{11}$ as a key position for improving hAMY3R potency in $hAM_{15-52}$ and $X_4$, $X_{37}$ and $X_{38}$ as key positions for eliminating hAM1R potency in $hAM_{15-52}$. Since $X_{17}$ was only of some importance for hAMY3R activity, this position was not considered a key position but only a preferred position to further improve the AMY3R potency of the $hAM_{15-52}$ analogues.

The systematic investigation showed that the hAMY3R potency of $hAM_{15-52}$ could be improved by substituting the amino acid K present in $hAM_{15-52}$ in position $X_{11}$ with the amino acid R present in $hAMY_{1-37}$. Furthermore, the systematic investigation showed that the hAM1R potency of $hAM_{15-52}$ could be decreased by substituting the amino acids present in position $X_4$, $X_{37}$ and $X_{38}$ in $hAM_{15-52}$ with the corresponding amino acids found in present in $hAMY_{1-37}$.

Deeper Investigation of Amino Acids in the Position $X_4$, $X_{11}$, $X_{17}$, $X_{37}$ and $X_{38}$.

The inventors systematically substituted representative amino acids covering representative amino acids for all the known amino acids into the 5 identified positions, at one position at the time (Table 6). As shown in example 1, all (SEQ ID: 1-360 had lost their activity on the hAM1R, with varying degree of potency on AMY3R. In order to score the individual amino acids on the 5 positions, the average $EC_{50}$ value for peptides containing a given amino acid in a given position was compared to the average $EC_{50}$ value $hAM_{15-52}$ analogues containing the reference amino acid in that position. Given a cut-off of 4-fold changes in potency, each amino acid in each position was scored as giving increased (I), decreased (D) or unchanged (U) potency, relative to the reference amino acid, on hAMY3R. The results are summarized in Table 6. From this data, it was shown that any of the amino acids R, W or Cit were capable of maintaining the AMY3R potency when present in position $X_{11}$ when compared to the reference whereas other representative amino acids decreased the potency. It was further shown that any of the amino acids Y, W, T, M, I, F, A, or C in $X_4$, any of the amino acids Y, W, T, Q, P, M, I, H, F, E, A, R, C or K in $X_{37}$ and any of the amino acids Hyp, Y, W, T, Q, P, M, I, H, F, E, A, R, or K in $X_{38}$ were able to maintain or improve AMY3R potency while remaining inactive on hAM1R.

Aspect 1: $hAM_{15-52}$ Analogues with Improved Amylin Potency

Thus, in a first aspect, the invention relates to an $hAM_{15-52}$ analogue or a pharmaceutically acceptable salt thereof comprising 38 amino acids ($X_1$-$X_{38}$) with an $hAMY3R$-$EC_{50} \leq 250$ pM, wherein the amino acid in position $X_{11}$ is selected from R, W or Cit and wherein the $hAM_{15-52}$ analogue has at least 50% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, (SEQ ID NO: 1). From example 1 (Table 2), it can be seen that almost all of the synthesized $hAM_{15-52}$ analogues have at least 50% homology to $hAM_{15-52}$, that a vast majority of the synthesized $hAM_{15-52}$ analogues have at least 60% of homology to $hAM_{15-52}$, and that a large portion of the synthesized $hAM_{15-52}$ analogues have at least 80% homology to $hAM_{15-52}$ (SEQ ID NO: 1). All of these $hAM_{15-52}$ analogues maintain the good fibrillation properties of $hAM_{15-52}$ (SEQ ID NO: 1) compared to $hAMY_{1-37}$ (SEQ ID NO: 2) (see example 2, Table 3). E.g., SEQ ID NO: 32 shows that the good physical stability (i.e. low fibrillation) of $hAM_{15-52}$ can be maintained as long as the $hAM_{15-52}$ analogues have at least 50% homology to $hAM_{15-52}$.

Thus, in a first aspect, the invention relates to a way to highly improve the hAMY3R potency of the $hAM_{15-52}$ fragment by a single substitution to R, W or Cit in position $X_{11}$, while maintaining the good physical stability (i.e. good fibrillation properties of $hAM_{15-52}$). These $hAM_{15-52}$ analogues will therefore be highly potent agonists on both hAMY3R and hAM1R (see SEQ ID NO: 361-392).

In the most preferred embodiment of the invention, $X_{11}$ is selected as R. In another embodiment, $X_{11}$ is selected as W. In yet an embodiment, $X_{11}$ is selected as Cit. The inventors found that this single amino acid substitution in $X_{11}$ provided increased hAMY3R potency to the $hAM_{15-52}$ analogue(s) while retaining hAM1R potency. The inventors further found that the hAMY3R potency could be maintained when $X_{17}$ was Y, T, Q, M, I, F, A, R or K, or even further improved by selecting $X_{17}$ as W or H. Thus, in an embodiment $X_{17}$ is selected as Y, W, T, Q, M, I, H, F, A, R or K. In a preferred embodiment, $X_{17}$ is selected as Y, W or H, more preferably W or H.

In an embodiment, the invention relates to an $hAM_{15-52}$ analogue comprising 38 amino acids ($X_1$-$X_{38}$) or a pharmaceutically acceptable salt thereof, wherein the amino acid in position $X_{11}$ is selected from R, W or Cit; $X_{17}$ is selected as Y, W, T, Q, M, I, H, F, A, R or K, preferably $X_{17}$ is selected as W or H and wherein the $hAM_{15-52}$ analogue has at least 50% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$ (SEQ ID NO: 1).

In yet an embodiment, the invention relates to an $hAM_{15-52}$ analogue comprising 38 amino acids ($X_1$-$X_{38}$) or a pharmaceutically acceptable salt thereof, wherein the amino acid in position $X_{11}$ is R; $X_{17}$ is selected as Y, W, T, Q, M, I, H, F, A, R or K, preferably $X_{17}$ is selected as W or H and wherein the $hAM_{15-52}$ analogue has at least 50% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, (SEQ ID NO: 1).

In yet an embodiment, the invention relates to an $hAM_{15-52}$ analogue comprising 38 amino acids ($X_1$-$X_{38}$) or a pharmaceutically acceptable salt thereof, wherein the amino acid in position $X_{11}$ is W; $X_{17}$ is selected as Y, W, T, Q, M, I, H, F, A, R or K, preferably $X_{17}$ is selected as W or H and wherein the $hAM_{15-52}$ analogue has at least 50% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, (SEQ ID NO: 1).

In yet an embodiment, the invention relates to an $hAM_{15-52}$ analogue comprising 38 amino acids ($X_1$-$X_{38}$) or a pharmaceutically acceptable salt thereof, wherein the amino acid in position $X_{11}$ is Cit; $X_{17}$ is selected as Y, W, T, Q, M, I, H, F, A, R or K, preferably $X_{17}$ is selected as W or H and wherein the $hAM_{15-52}$ analogue has at least 50% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, (SEQ ID NO: 1).

In a preferred embodiment, the invention relates to an $hAM_{15-52}$ analogue or a pharmaceutically acceptable salt thereof comprising the amino acid sequence of formula (I):

(I) (SEQ ID NO: 394)

$$\text{G—C—R—}X_4\text{—G—T—C—T—V—Q—}X_{11}\text{—L—A—H—Q—I—}X_{17}\text{—Q—F—T—D—K—D—K—D—N—V—A—P—R—S—K—I—S—P—Q—}X_{37}\text{-}X_{38}$$

with a disulfide bond between the two C residues.

wherein
$X_{11}$ is selected from R, W or Cit;
$X_{17}$ is selected as Y, W, T, Q, M, I, H, F, A, R, or K;
$X_4$ is selected from F, Y, W, T, M, I, A, or C;
$X_{37}$ is selected from G, Y, S, W, T, Q, P, M, I, H, F, E, A, R, C, or K;
$X_{38}$ is selected from Hyp, Y, W, T, Q, P, M, I, H, F, E, A, R, or K;
or a derivative thereof with at least 50% homology to $hAM_{15-52}$, preferably at least 60% homology to $hAM_{15-52}$, such as at least 70% homology to $hAM_{15-52}$, more preferably at least 80% homology to $hAM_{15-52}$, even more preferably at least 85% homology to $hAM_{15-52}$, such as at least 90% homology to $hAM_{15-52}$, most preferably at least 95% homology to $hAM_{15-52}$, wherein $X_{11}$ is selected from R, W, or Cit; $X_{17}$ is selected as Y, W, T, Q, M, I, H, F, A, R, or K; $X_4$ is selected from F, Y, W, T, M, I, A or C; $X_{37}$ is selected from G, Y, S, W, T, Q, P, M, I, H, F, E, A, R, C, or K; $X_{38}$ is selected from Hyp, Y, W, T, Q, P, M, I, H, F, E, A, R, or K.

In another preferred embodiment, the invention relates to an $hAM_{15-52}$ analogue or a pharmaceutically acceptable salt thereof comprising the amino acid sequence of formula (I):

(I) (SEQ ID NO: 395)

$$\text{G—C—R—}X_4\text{—G—T—C—T—V—Q—}X_{11}\text{—L—A—H—Q—I—}X_{17}\text{—Q—F—T—D—K—D—K—D—N—V—A—P—R—S—K—I—S—P—Q—}X_{37}\text{-}X_{38}$$

with a disulfide bond between the two C residues.

wherein
X$_{11}$ is selected from R;
X$_{17}$ is selected as Y, W, T, Q, M, I, H, F, A, R, or K;
X$_4$ is selected from F, Y, W, T, M, I, A, or C;
X$_{37}$ is selected from G, Y, S, W, T, Q, P, M, I, H, F, E, A, R, C, or K;
X$_{38}$ is selected from Hyp, Y, W, T, Q, P, M, I, H, F, E, A, R, or K;
or a derivative thereof with at least 50% homology to hAM$_{15-52}$, preferably at least 60% homology to hAM$_{15-52}$, such as at least 70% homology to hAM$_{15-52}$, more preferably at least 80% homology to hAM$_{15-52}$, even more preferably at least 85% homology to hAM$_{15-52}$, such as at least 90% homology to hAM$_{15-52}$, most preferably at least 95% homology to hAM$_{15-52}$, wherein X$_{11}$ is selected from R; X$_{17}$ is selected as Y, W, T, Q, M, I, H, F, A, R, or K; X$_4$ is selected from F, Y, W, T, M, I, A, or C; X$_{37}$ is selected from G, Y, S, W, T, Q, P, M, I, H, F, E, A, R, C, or K; X$_{38}$ is selected from Hyp, Y, W, T, Q, P, M, I, H, F, E, A, R, or K.

In a more preferred embodiment, the invention relates to an hAM$_{15-52}$ analogue or a pharmaceutically acceptable salt thereof comprising the amino acid sequence of formula (I):

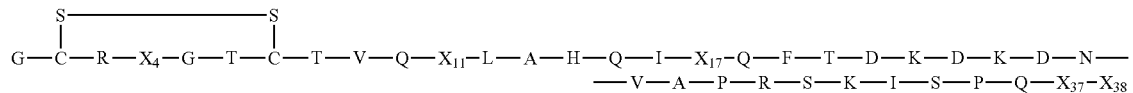

(I) (SEQ ID NO: 396)

wherein
X$_{11}$ is selected from R;
X$_{17}$ is selected as Y, W, or H;
X$_4$ is selected from F, Y, W, T, M, I, A, or C;
X$_{37}$ is selected from G, Y, S, W, T, Q, P, M, I, H, F, E, A, R, C, or K;
X$_{38}$ is selected from Hyp, Y, W, T, Q, P, M, I, H, F, E, A, R, or K;
or a derivative thereof with at least 50% homology to hAM$_{15-52}$, preferably at least 60% homology to hAM$_{15-52}$, such as at least 70% homology to hAM$_{15-52}$, more preferably at least 80% homology to hAM$_{15-52}$, even more preferably at least 85% homology to hAM$_{15-52}$, such as at least 90% homology to hAM$_{15-52}$, most preferably at least 95% homology to hAM$_{15-52}$, wherein X$_{11}$ is selected from R; X$_{17}$ is selected as Y, W, or H; X$_4$ is selected from F, Y, W, T, M, I, A, or C; X$_{37}$ is selected from G, Y, S, W, T, Q, P, M, I, H, F, E, A, R, C, or K; X$_{38}$ is selected from Hyp, Y, W, T, Q, P, M, I, H, F, E, A, R, or K.

In yet a more preferred embodiment, the invention relates to an hAM$_{15-52}$ analogue or a pharmaceutically acceptable salt thereof comprising the amino acid sequence of formula (I):

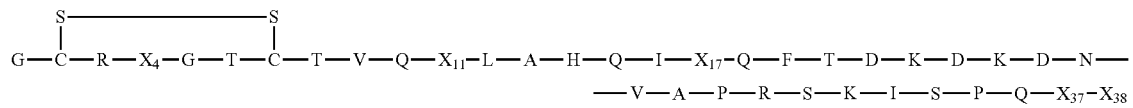

(I) (SEQ ID NO: 397)

wherein
- $X_{11}$ is selected from R;
- $X_{17}$ is selected as Y, W, or H;
- $X_4$ is selected from F, W, M, I, or C;
- $X_{37}$ is selected from G, Y, S, W, T, Q, P, M, I, H, F, E, A, R, C, or K;
- $X_{38}$ is selected from Hyp, Y, W, T, Q, P, M, I, H, F, E, A, R, or K;
- or a derivative thereof with at least 50% homology to hAM$_{15\text{-}52}$, preferably at least 60% homology to hAM$_{15\text{-}52}$, such as at least 70% homology to hAM$_{15\text{-}52}$, more preferably at least 80% homology to hAM$_{15\text{-}52}$, even more preferably at least 85% homology to hAM$_{15\text{-}52}$, such as at least 90% homology to hAM$_{15\text{-}52}$, most preferably at least 95% homology to hAM$_{15\text{-}52}$, wherein $X_{11}$ is selected from R; $X_{17}$ is selected as Y, W, or H; $X_4$ is selected from F, W, M, I, or C; $X_{37}$ is selected from G, Y, S, W, T, Q, P, M, I, H, F, E, A, R, C, or K; $X_{38}$ is selected from Hyp, Y, W, T, Q, P, M, I, H, F, E, A, R, or K.

In yet a more preferred embodiment, the invention relates to an hAM$_{15\text{-}52}$ analogue or a pharmaceutically acceptable salt thereof comprising the amino acid sequence of formula (I):

(I) (SEQ ID NO: 398)

$$\begin{array}{c}\overset{S\text{———}S}{\underset{|\quad\quad\quad\quad|}{}}\\ G-C-R-X_4-G-T-C-T-V-Q-X_{11}-L-A-H-Q-I-X_{17}-Q-F-T-D-K-D-K-D-N-\\ -V-A-P-R-S-K-I-S-P-Q-X_{37}-X_{38}\end{array}$$

wherein
- $X_{11}$ is selected from R;
- $X_{17}$ is selected as Y, W, or H;
- $X_4$ is selected from F, Y, W, T, M, I, A, or C;
- $X_{37}$ is selected from G, Y, W, P, H, or F;
- $X_{38}$ is selected from Hyp, Y, W, T, Q, P, M, I, H, F, E, A, R, or K;
- or a derivative thereof with at least 50% homology to hAM$_{15\text{-}52}$, preferably at least 60% homology to hAM$_{15\text{-}52}$, such as at least 70% homology to hAM$_{15\text{-}52}$, more preferably at least 80% homology to hAM$_{15\text{-}52}$, even more preferably at least 85% homology to hAM$_{15\text{-}52}$, such as at least 90% homology to hAM$_{15\text{-}52}$, most preferably at least 95% homology to hAM$_{15\text{-}52}$, $X_{11}$ is selected from R; $X_{17}$ is selected as Y, W or H; $X_4$ is selected from F, Y, W, T, M, I, A, or C; $X_{37}$ is selected from G, Y, W, P, H, or F; $X_{38}$ is selected from Hyp, Y, W, T, Q, P, M, I, H, F, E, A, R, or K.

In yet a more preferred embodiment, the invention relates to an hAM$_{15\text{-}52}$ analogue or a pharmaceutically acceptable salt thereof comprising the amino acid sequence of formula (I):

(I) (SEQ ID NO: 399)

$$\begin{array}{c}\overset{S\text{———}S}{\underset{|\quad\quad\quad\quad|}{}}\\ G-C-R-X_4-G-T-C-T-V-Q-X_{11}-L-A-H-Q-I-X_{17}-Q-F-T-D-K-D-K-D-N-\\ -V-A-P-R-S-K-I-S-P-Q-X_{37}-X_{38}\end{array}$$

wherein $X_{11}$ is selected from R;

$X_{17}$ is selected as Y, W, or H;

$X_4$ is selected from F, Y, W, T, M, I, A, or C;

$X_{37}$ is selected from G, Y, S, W, T, Q, P, M, I, H, F, E, A, R, C, or K;

$X_{38}$ is selected from Hyp, Y, W, M, or F;

or a derivative thereof with at least 50% homology to $hAM_{15-52}$, preferably at least 60% homology to $hAM_{15-52}$, such as at least 70% homology to $hAM_{15-52}$, more preferably at least 80% homology to $hAM_{15-52}$, even more preferably at least 85% homology to $hAM_{15-52}$, such as at least 90% homology to $hAM_{15-52}$, most preferably at least 95% homology to $hAM_{15-52}$, wherein $X_{11}$ is selected from R; $X_{17}$ is selected as Y, W, or H; $X_4$ is selected from F, Y, W, T, M, I, A, or C; $X_{37}$ is selected from G, Y, S, W, T, Q, P, M, I, H, F, E, A, R, C, or K; $X_{38}$ is selected from Hyp, Y, W, M, or F.

In yet a more preferred embodiment, the invention relates to an $hAM_{15-52}$ analogue or a pharmaceutically acceptable salt thereof comprising the amino acid sequence of formula (I):

(I) (SEQ ID NO: 400)

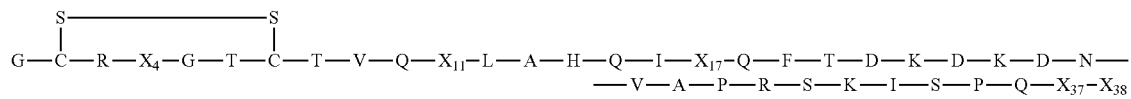

wherein $X_{11}$ is selected from R;

$X_{17}$ is selected as Y, W, or H;

$X_4$ is selected from F, W, M, I, or C;

$X_{37}$ is selected from G, Y, W, P, H, or F;

$X_{38}$ is selected from Hyp, Y, W, T, Q, P, M, I, H, F, E, A, R, or K;

or a derivative thereof with at least 50% homology to $hAM_{15-52}$, preferably at least 60% homology to $hAM_{15-52}$, such as at least 70% homology to $hAM_{15-52}$, more preferably at least 80% homology to $hAM_{15-52}$, even more preferably at least 85% homology to $hAM_{15-52}$, such as at least 90% homology to $hAM_{15-52}$, most preferably at least 95% homology to $hAM_{15-52}$, wherein $X_{11}$ is selected from R; $X_{17}$ is selected as Y, W or H; $X_4$ is selected from F, W, M, I, or C; $X_{37}$ is selected from G, Y, W, P, H, or F; $X_{38}$ is selected from Hyp, Y, W, T, Q, P, M, I, H, F, E, A, R, or K.

In yet a more preferred embodiment, the invention relates to an $hAM_{15-52}$ analogue or a pharmaceutically acceptable salt thereof comprising the amino acid sequence of formula (I):

(I) (SEQ ID NO: 401)

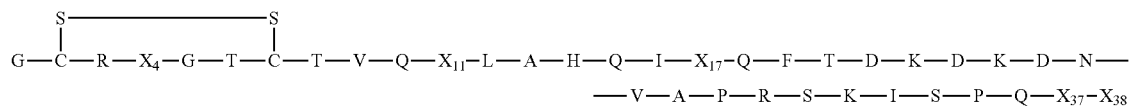

wherein
$X_{11}$ is selected from R;
$X_{17}$ is selected as Y, W, or H;
$X_4$ is selected from F, W, M, I, or C;
$X_{37}$ is selected from G, Y, S, W, T, Q, P, M, I, H, F, E, A, R, C, or K;
$X_{38}$ is selected from Hyp, Y, W, M, or F;
or a derivative thereof with at least 50% homology to $hAM_{15-52}$, preferably at least 60% homology to $hAM_{15-52}$, such as at least 70% homology to $hAM_{15-52}$, more preferably at least 80% homology to $hAM_{15-52}$, even more preferably at least 85% homology to $hAM_{15-52}$, such as at least 90% homology to $hAM_{15-52}$, most preferably at least 95% homology to $hAM_{15-52}$, wherein $X_{11}$ is selected from R; $X_{17}$ is selected as Y, W, or H; $X_4$ is selected from F, W, M, I, or C; $X_{37}$ is selected from G, Y, S, W, T, Q, P, M, I, H, F, E, A, R, C, or K; $X_{38}$ is selected from Hyp, Y, W, M, or F.

In yet a more preferred embodiment, the invention relates to an $hAM_{15-52}$ analogue or a pharmaceutically acceptable salt thereof comprising the amino acid sequence of formula (I):

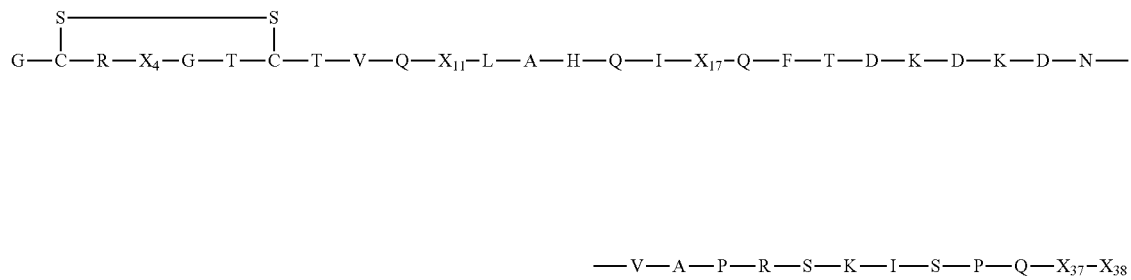

(I) (SEQ ID NO: 402)

wherein
$X_{11}$ is selected from R;
$X_{17}$ is selected as Y, W, or H;
$X_4$ is selected from F, Y, W, T, M, I, A, or C;
$X_{37}$ is selected from G, Y, W, P, H, or F;
$X_{38}$ is selected from Hyp, Y, W, M, or F;
or a derivative thereof with at least 50% homology to $hAM_{15-52}$, preferably at least 60% homology to $hAM_{15-52}$, such as at least 70% homology to $hAM_{15-52}$, more preferably at least 80% homology to $hAM_{15-52}$, even more preferably at least 85% homology to $hAM_{15-52}$, such as at least 90% homology to $hAM_{15-52}$, most preferably at least 95% homology to $hAM_{15-52}$, wherein $X_{11}$ is selected from R; $X_{17}$ is selected as Y, W, or H; $X_4$ is selected from F, Y, W, T, M, I, A, or C; $X_{37}$ is selected from G, Y, W, P, H, or F; $X_{38}$ is selected from Hyp, Y, W, M, or F.

In yet an even more preferred embodiment, the invention relates to an $hAM_{15-52}$ analogue or a pharmaceutically acceptable salt thereof comprising the amino acid sequence of formula (I):

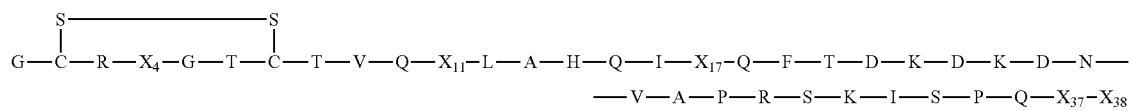

(I) (SEQ ID NO: 403)

wherein
$X_{11}$ is selected from R;
$X_{17}$ is selected as Y, W, or H;
$X_4$ is selected from F, W, M, I, or C;
$X_{37}$ is selected from G, Y, W, P, H, or F;
$X_{38}$ is selected from Hyp, Y, W, M, or F;
or a derivative thereof with at least 50% homology to $hAM_{15-52}$, preferably at least 60% homology to $hAM_{15-52}$, such as at least 70% homology to $hAM_{15-52}$, more preferably at least 80% homology to $hAM_{15-52}$, even more preferably at least 85% homology to $hAM_{15-52}$, such as at least 90% homology to $hAM_{15-52}$, most preferably at least 95% homology to $hAM_{15-52}$, wherein $X_{11}$ is selected from R; $X_{17}$ is selected as Y, W or H; $X_4$ is selected from F, W, M, I, or C; $X_{37}$ is selected from G, Y, W, P, H, or F; $X_{38}$ is selected from Hyp, Y, W, M, or F.

In yet a more preferred embodiment, the invention relates to an $hAM_{15-52}$ analogue comprising the amino acid sequence of formula (I):

(I) (SEQ ID NO: 411)

$$\begin{array}{c} S\text{———————}S \\ | \qquad\qquad\qquad | \\ G-C-R-F-G-T-C-T-V-Q-X_{11}-L-A-H-Q-I-Y-Q-F-T-D-K-D-K-D-N- \\ -V-A-P-R-S-K-I-S-P-Q-G\text{-Hyp} \end{array}$$

wherein, $X_{11}$ is selected from R, W, or Cit
or a derivative thereof with at least 50% homology to $hAM_{15-52}$, least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, most preferably at least 90% homology to $hAM_{15-52}$ to $hAM_{15-52}$, such as at least 95% homology to $hAM_{15-52}$, wherein, $X_{11}$ is selected from R, W, or Cit.

In a most preferred embodiment, the invention relates to an $hAM_{15-52}$ analogue of SEQ ID NO: 3-392 or a derivative thereof with at least 90% homology to any one of SEQ ID NO: 3-392, preferably at least 95% homology any one of SEQ ID NO: 3-392, more preferably at least 96% homology any one of SEQ ID NO: 3-392 most preferably at least 97% homology any one of SEQ ID NO: 3-392 with the proviso that a derivative thereof has R, W, or Cit in position $X_{11}$, preferably R in position $X_{11}$.

In yet a most preferred embodiment, the invention relates to an $hAM_{15-52}$ analogue of SEQ ID NO: 3-392 or a derivative thereof with at least 90% homology to any one of SEQ ID NO: 3-392, preferably at least 95% homology to any one of SEQ ID NO: 3-392, more preferably at least 96% homology any one of SEQ ID NO: 3-392, most preferably at least 97% homology any one of SEQ ID NO: 3-278, with the proviso that a derivative thereof has the same amino acid in position $X_{11}$, as the respective SEQ ID NO: 3-392 from it is derived.

Aspect 2: Selective $hAM_{15-52}$ Analogues with Improved Amylin Potency

Number of Positions Needed to Abolish or Reduce AM1R Potency in $hAM_{15-52}$.

The inventors found that hAM1R potency could be abolished or reduced in $hAM_{15-52}$ by changing at least one amino acid in any of the positions $X_4$, $X_{37}$ or $X_{38}$ since all of them were critical for hAM1R potency.

Decreasing hAM1R Potency with Amino Acids in Position $X_4$, $X_{37}$ or $X_{38}$.

$X_4$: The inventors found that the amino acids Y, W, T, M, I, A or C in position $X_4$ were capable of decreasing the hAM1R potency. Thus, in an embodiment, $X_4$ is selected from Y, W, T, M, I, A or C. Furthermore, the amino acids W, M, I or C in position $X_4$ were most effective at improving hAMY3R potency (see example 5, table 6). Thus, in a highly preferred embodiment of the invention, $X_4$ is selected as W, M, I or C. Since the inventors found that a single position chosen among $X_4$, $X_{37}$ or $X_{38}$ was enough to abolish or reduce AM1R potency it follows that in some embodiments $X_4$ is F (i.e. the native amino acid present in $hAM_{15-52}$ (SEQ ID NO: 1) in said position) and the AM1R potency is abolished or reduced using position $X_{37}$ and/or $X_{38}$. Thus, in any of the above embodiments for $X_4$, F may be included and the AM1R potency abolished or reduced using position $X_7$ and/or $X_{38}$.

$X_{37}$: Likewise, the inventors found that the amino acids Y, S, W, T, Q, P, M, I, H, F, E, A, R, C in position $X_{37}$ were capable of decreasing the hAM1R potency. Thus, in an embodiment, $X_{37}$ is selected from Y, S, W, T, Q, P, M, I, H, F, E, A, R, C. Furthermore, the amino acids Y, W, P, H or F in position $X_{37}$ were most effective at improving hAMY3R potency (see example 5, table 6). Thus, in a highly preferred embodiment of the invention, $X_{37}$ is selected as Y, W, P, H or F. Since the inventors found that a single position chosen among $X_4$, $X_{37}$ or $X_{38}$ was enough to abolish or reduce AM1R potency it follows that in some embodiments $X_{37}$ is G (i.e. the native amino present in $hAM_{15-52}$ (SEQ ID NO: 1) in said position), and the AM1R potency is abolished or reduced using position $X_4$ and/or $X_{38}$. Thus, in any of the above embodiments for $X_{37}$, G may be included and the AM1R potency abolished or reduced using position $X_4$ and/or $X_{38}$.

$X_{38}$: Likewise, the inventors found that the amino acids Hyp, W, T, Q, P, M, I, H, F, E, A, R, or K in position $X_{38}$ were capable of decreasing the hAM1R potency. Thus, in an embodiment, $X_{38}$ is selected from Hyp, W, T, Q, P, M, I, H, F, E, A, R, or K. Furthermore, the amino acids Hyp, W, M or F were most effective at improving hAMY3R potency (see example 5, table 6). Thus, in a highly preferred embodiment of the invention, $X_{38}$ is selected as Hyp, W, M or F. In the most preferred embodiment of the invention, $X_{38}$ is selected as Hyp. Since the inventors found that a single position chosen among $X_4$, $X_{37}$ or $X_{38}$ was enough to abolish or reduce AM1R potency it follows that in some embodiments $X_{38}$ is Y (i.e. the native amino present in $hAM_{15-52}$ (SEQ ID NO: 1) in said position), and the AM1R potency is abolished or reduced using position $X_4$ and/or $X_{37}$. Thus, in any of the above embodiments for $X_{38}$, Y may be included and the AM1R potency abolished or reduced using position $X_4$ and/or $X_{37}$.

A simple illustration of aspect 2 of the invention can be seen by comparing the alignment of $hAM_{15-52}$ (SEQ ID NO: 1) and SEQ ID NO: 169 shown below.

SEQ ID NO: 1
G C R F G T C T V Q K L A H Q I Y Q F T D K D K D N
V A P R S K I S P Q G Y

SEQ ID NO: 169
G C R F G T C T V Q R L A H Q I Y Q F T D K D K D N
V A P R S K I S P Q G Hyp

SEQ ID NO: 1
hAMY3R EC$_{50}$ 1.274 nM and hAM1R EC$_{50}$ 1.113 nM

SEQ ID NO: 169
hAMY3R EC$_{50}$ 0.063 nM and hAM1R EC$_{50}$ 2981.0 nM

As can be seen, the R in position $X_{11}$ has improved the potency on AMY3R approximately 20-fold, and the Hyp in position $X_{38}$ has decreased the potency on AM1R approximately 2500-fold. Therefore, only two substitutions have converted hAM$_{15-52}$ into an amylin agonist with same pharmacological profile as hAMY$_{1-37}$. At the same time, SEQ ID NO: 169 has maintained the physical stability (ThT signal: 2.700%) of hAM$_{15-52}$ (ThT signal: 2.600%) compared to hAMY$_{1-37}$ (ThT signal: 100.0%) (see example 2, Table 3).

Thus, in a second aspect, the invention relates to a way to more or less completely abolish hAM1R potency of the hAM$_{15-52}$ fragment by one or more substitutions in position $X_4$, $X_{37}$ and/or $X_{38}$ and at the same time improve or maintain sufficient AMY3R potency. These hAM$_{15-52}$ analogues will therefore be highly potent and selective hAMY3R analogues. At the same time these hAM$_{15-52}$ analogues maintain the physical stability of hAM$_{15-52}$ due to the sequence homology (identity) with hAM$_{15-52}$. As shown in example 2, Table 3, the good physical stability of hAM$_{15-52}$ may be maintained or even improved in the peptides (due to at least 50% homology to hAM$_{15-52}$), while providing new hAMY3R agonists that are as potent and selective as natural human amylin. In other words, the second aspect of the present invention has created a functional human amylin analogue disguised in an adrenomedullin backbone.

Increasing hAMY3R Potency with Amino Acids in Position $X_{17}$.

The inventors further found that the hAMY3R potency could be maintained when $X_{17}$ as Y, T, Q, M, I, F, A, R, or K, or even further improved when $X_{17}$ was W or H. Thus, in an embodiment, $X_{17}$ is selected as Y, W, T, Q, M, I, H, F, A, R, or K. In a preferred embodiment, $X_{17}$ is selected as W, or H.

Thus, in a second aspect, the invention relates to hAM$_{15-52}$ analogues comprising 38 amino acids ($X_1$-$X_{38}$) or a pharmaceutically acceptable salt thereof, wherein the amino acid in position $X_{11}$ is selected from R, W or Cit and wherein the hAM$_{15-52}$ analogue has at least 50% homology to hAM$_{15-52}$, such as at least 55% homology to hAM$_{15-52}$, such as at least 60% homology to hAM$_{15-52}$, such as at least 65% homology to hAM$_{15-52}$, preferably at least 70% homology to hAM$_{15-52}$, such as at least 75% homology to hAM$_{15-52}$, more preferably at least 80% homology to hAM$_{15-52}$, such as at least 85% homology to hAM$_{15-52}$, most preferably at least 90% homology to hAM$_{15-52}$, such as at least 95% homology to hAM$_{15-52}$ (SEQ ID NO: 1) and further wherein $X_4$ is selected as F, Y, W, T, M, I, A or C; $X_{37}$ is selected as G, Y, S, W, T, Q, P, M, I, H, F, E, A, R, C or K; $X_{38}$ is selected as Hyp, Y, W, T, Q, P, M, I, H, F, E, A, R, or K, with the proviso that at least one of the positions $X_4$, $X_{37}$ or $X_{38}$ is not the amino acid present in hAM$_{15-52}$ (SEQ ID NO: 1) in said position, more preferably, at least two of the positions $X_4$, $X_{37}$ or $X_{38}$ is not the amino acid present in hAM$_{15-52}$ (SEQ ID NO: 1) in said position. In the second aspect, the hAM$_{15-52}$ analogues have an hAMY3R-EC$_{50}$≤250 pM and an hAM1R-EC$_{50}$≥25 nM.

In an embodiment, $X_4$ is selected as F, W, M, I or C; $X_{37}$ is selected as G, Y, S, W, T, Q, P, M, I, H, F, E, A, R, C, or K; $X_{38}$ is selected as Hyp, Y, W, T, Q, P, M, I, H, F, E, A, R, or K, with the proviso that at least one of the positions $X_4$, $X_{37}$, or $X_{38}$ is not the amino acid present in hAM$_{15-52}$ (SEQ ID NO: 1) in said position, more preferably, at least two of the positions $X_4$, $X_{37}$, or $X_{38}$ are not the amino acid present in hAM$_{15-52}$ (SEQ ID NO: 1) in said position.

In an embodiment, $X_4$ is selected as F, Y, W, T, M, I, A or C; $X_{37}$ is selected as G, Y, W, P, H or F; $X_{38}$ is selected as Hyp, Y, W, T, Q, P, M, I, H, F, E, A, R, or K, with the proviso that at least one of the positions $X_4$, $X_{37}$ or $X_{38}$ is not the amino acid present in hAM$_{15-52}$ (SEQ ID NO: 1) in said position, more preferably, at least two of the positions $X_4$, $X_{37}$ or $X_{38}$ are not the amino acid present in hAM$_{15-52}$ (SEQ ID NO: 1) in said position.

In an embodiment, $X_4$ is selected as F, Y, W, T, M, I, A or C; $X_{37}$ is selected as G, Y, S, W, T, Q, P, M, I, H, F, E, A, R, C or K; $X_{38}$ is selected as Hyp, Y, W, M or F, with the proviso that at least one of the positions $X_4$, $X_{37}$ or $X_{38}$ is not the amino acid present in hAM$_{15-52}$ (SEQ ID NO: 1) in said position, more preferably, at least two of the positions $X_4$, $X_{37}$, or $X_{38}$ is not the amino acid present in hAM$_{15-52}$ (SEQ ID NO: 1) in said position.

In an embodiment, $X_4$ is selected as F, W, M, I, or C; $X_{37}$ is selected as G, Y, W, P, H, or F; $X_{38}$ is selected as Hyp, Y, W, M or F, with the proviso that at least one of the positions $X_4$, $X_{37}$ or $X_{38}$ is not the amino acid present in hAM$_{15-52}$ (SEQ ID NO: 1) in said position, more preferably, at least two of the positions $X_4$, $X_{37}$, or $X_{38}$ are not the amino acid present in hAM$_{15-52}$ (SEQ ID NO: 1) in said position.

In a preferred embodiment, the invention relates to an hAM$_{15-52}$ analogue or a pharmaceutically acceptable salt thereof comprising the amino acid sequence of formula (I):

(I) (SEQ ID NO: 394)

$$\begin{array}{c} \overset{S\text{———————}S}{|\phantom{xxxxxxxxxxxx}|} \\ G\text{—}C\text{—}R\text{—}X_4\text{—}G\text{—}T\text{—}C\text{—}T\text{—}V\text{—}Q\text{—}X_{11}\text{—}L\text{—}A\text{—}H\text{—}Q\text{—}I\text{—}X_{17}\text{—}Q\text{—}F\text{—}T\text{—}D\text{—}K\text{—}D\text{—}K\text{—}D\text{—}N\text{—} \\ \text{—}V\text{—}A\text{—}P\text{—}R\text{—}S\text{—}K\text{—}I\text{—}S\text{—}P\text{—}Q\text{—}X_{37}\text{-}X_{38} \end{array}$$

wherein
$X_{11}$ is selected from R, W, or Cit;
$X_{17}$ is selected as Y, W, T, Q, M, I, H, F, A, R, K;
$X_4$ is selected from F, Y, W, T, M, I, A, or C;
$X_{37}$ is selected from G, Y, S, W, T, Q, P, M, I, H, F, E, A, R, C, or K;
$X_{38}$ is selected from Hyp, Y, W, T, Q, P, M, I, H, F, E, A, R, or K;
and further wherein at least one of the positions $X_4$, $X_{37}$ or $X_{38}$ is not the amino acid present in hAM$_{15-52}$ (SEQ ID NO: 1) in said position;

or a derivative thereof with at least 50% homology to hAM$_{15-52}$, such as at least 55% homology to hAM$_{15-52}$, such as at least 60% homology to hAM$_{15-52}$, such as at least 65% homology to hAM$_{15-52}$, preferably at least 70% homology to hAM$_{15-52}$, such as at least 75% homology to hAM$_{15-52}$, more preferably at least 80% homology, even more preferably at least 85% homology, such as at least 90% homology, most preferably at least 95% homology, wherein X$_{11}$ is selected from R, W, or Cit; X$_{17}$ is selected as Y, W, T, Q, M, I, H, F, A, R, K; X$_4$ is selected from F, Y, W, T, M, I, A or C; X$_{37}$ is selected from G, Y, S, W, T, Q, P, M, I, H, F, E, A, R, C or K; X$_{38}$ is selected from Hyp, Y, W, T, Q, P, M, I, H, F, E, A, R, or K; and further wherein at least one of the positions X$_4$, X$_{37}$ or X$_{38}$ is not the amino acid present in hAM$_{15-52}$ (SEQ ID NO: 1) in said position.

In yet a more preferred embodiment, the invention relates to an hAM$_{15-52}$ analogue or a pharmaceutically acceptable salt thereof comprising the amino acid sequence of formula (I):

(I) (SEQ ID NO: 404)

$$\begin{array}{c} \text{S}\overline{\phantom{XXXXXXXX}}\text{S} \\ | \qquad\qquad | \\ \text{G—C—R—X}_4\text{—G—T—C—T—V—Q—X}_{11}\text{—L—A—H—Q—I—X}_{17}\text{—Q—F—T—D—K—D—K—D—N—} \\ \text{—V—A—P—R—S—K—I—S—P—Q—X}_{37}\text{-X}_{38} \end{array}$$

wherein
X$_{11}$ is selected from R, W, or Cit;
X$_{17}$ is selected as Y, W, T, Q, M, I, H, F, A, R or K;
X$_4$ is selected from F, W, M, I or C;
X$_{37}$ is selected from G, Y, S, W, T, Q, P, M, I, H, F, E, A, R, C or K;
X$_{38}$ is selected from Hyp, Y, W, T, Q, P, M, I, H, F, E, A, R, or K;
and further wherein at least one of the positions X$_4$, X$_{37}$ or X$_{38}$ is not the amino acid present in hAM$_{15-52}$ (SEQ ID NO: 1) in said position;
or a derivative thereof with at least 50% homology to hAM$_{15-52}$, such as at least 55% homology to hAM$_{15-52}$, such as at least 60% homology to hAM$_{15-52}$, such as at least 65% homology to hAM$_{15-52}$, preferably at least 70% homology to hAM$_{15-52}$, such as at least 75% homology to hAM$_{15-52}$, more preferably at least 80% homology, such as at least 85% homology, more preferably at least 90% homology, most preferably at least 95% homology, wherein X$_{11}$ is selected from R, W or Cit; X$_{17}$ is selected as Y, W, T, Q, M, I, H, F, A, R or K; X$_4$ is selected from F, W, M, I or C; X$_{37}$ is selected from G, Y, S, W, T, Q, P, M, I, H, F, E, A, R, C or K; X$_{38}$ is selected from Hyp, Y, W, T, Q, P, M, I, H, F, E, A, R, or K; and further wherein at least one of the positions X$_4$, X$_{37}$ or X$_{38}$ is not the amino acid present in hAM$_{15-52}$ (SEQ ID NO: 1) in said position.

In another more preferred embodiment, the invention relates to an hAM$_{15-52}$ analogue or a pharmaceutically acceptable salt thereof comprising the amino acid sequence of formula (I):

(I) (SEQ ID NO: 405)

$$\begin{array}{c} \text{S}\overline{\phantom{XXXXXXXX}}\text{S} \\ | \qquad\qquad | \\ \text{G—C—R—X}_4\text{—G—T—C—T—V—Q—X}_{11}\text{—L—A—H—Q—I—X}_{17}\text{—Q—F—T—D—K—D—K—D—N—} \\ \text{—V—A—P—R—S—K—I—S—P—Q—X}_{37}\text{-X}_{38} \end{array}$$

wherein
$X_{11}$ is selected from R, W, or Cit;
$X_{17}$ is selected as Y, W, T, Q, M, I, H, F, A, R, or K;
$X_4$ is selected from F, Y, W, T, M, I, A, or C;
$X_{37}$ is selected from G, Y, W, P, H, or F;
$X_{38}$ is selected from Hyp, Y, W, T, Q, P, M, I, H, F, E, A, R, or K;
and further wherein at least one of the positions $X_4$, $X_{37}$ or $X_{38}$ is not the amino acid present in $hAM_{15-52}$ (SEQ ID NO: 1) in said position;
or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology, more preferably at least 90% homology, most preferably at least 95% homology, wherein $X_{11}$ is selected from R, W, or Cit; $X_{17}$ is selected as Y, W, T, Q, M, I, H, F, A, R, or K; $X_4$ is selected from F, Y, W, T, M, I, A, or C; $X_{37}$ is selected from G, Y, W, P, H, or F; $X_{38}$ is selected from Hyp, Y, W, T, Q, P, M, I, H, F, E, A, R, or K; and further wherein at least one of the positions $X_4$, $X_{37}$, or $X_{38}$ is not the amino acid present in $hAM_{15-52}$ (SEQ ID NO: 1) in said position.

In yet a more preferred embodiment, the invention relates to an $hAM_{15-52}$ analogue or a pharmaceutically acceptable salt thereof comprising the amino acid sequence of formula (I):

(I) (SEQ ID NO: 407)

wherein
$X_{11}$ is selected from R, W, or Cit;
$X_{17}$ is selected as Y, W, T, Q, M, I, H, F, A, R, or K;
$X_4$ is selected from F, W, M, I, or C;
$X_{37}$ is selected from G, Y, W, P, H, or F;
$X_{38}$ is selected from Hyp, Y, W, T, Q, P, M, I, H, F, E, A, R, or K;
and further wherein at least one of the positions $X_4$, $X_{37}$ or $X_{38}$ is not the amino acid present in $hAM_{15-52}$ (SEQ ID NO: 1) in said position;
or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology, more preferably at least 90% homology, most preferably at least 95% homology, wherein $X_{11}$ is selected from R, W, or Cit; $X_{17}$ is selected as Y, W, T, Q, M, I, H, F, A, R, or K; $X_4$ is selected from F, Y, W, T, M, I, A, or C; $X_{37}$ is selected from G, Y, W, P, H, or F; $X_{38}$ is selected from Hyp, Y, W, T, Q, P, M, I, H, F, E, A, R, or K; and further wherein at least one of the positions $X_4$, $X_{37}$, or $X_{38}$ is not the amino acid present in $hAM_{15-52}$ (SEQ ID NO: 1) in said position.

In yet a more preferred embodiment, the invention relates to an $hAM_{15-52}$ analogue or a pharmaceutically acceptable salt thereof comprising the amino acid sequence of formula (I):

(I) (SEQ ID NO: 406)

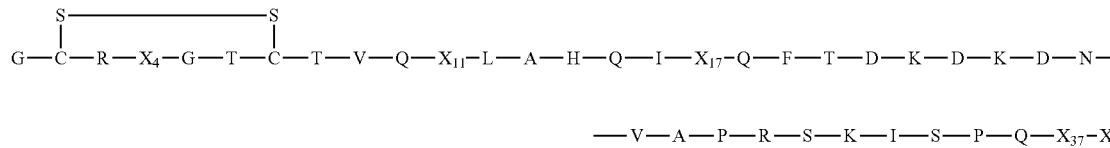

wherein
$X_{11}$ is selected from R, W, or Cit;
$X_{17}$ is selected as Y, W, T, Q, M, I, H, F, A, R, or K;
$X_4$ is selected from F, Y, W, T, M, I, A, or C;
$X_{37}$ is selected from G, Y, S, W, T, Q, P, M, I, H, F, E, A, R, C, or K;
$X_{38}$ is selected from Hyp, Y, W, M, or F;
and further wherein at least one of the positions $X_4$, $X_{37}$ or $X_{38}$ is not the amino acid present in $hAM_{15-52}$ (SEQ ID NO: 1) in said position;
or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, more preferably at least 90% homology to $hAM_{15-52}$, most preferably at least 95% homology to $hAM_{15-52}$, wherein $X_{11}$ is selected from R, W, or Cit; $X_{17}$ is selected as Y, W, T, Q, M, I, H, F, A, R, or K; $X_4$ is selected from F, W, M, I, or C; $X_{37}$ is selected from G, Y, W, P, H, or F; $X_{38}$ is selected from Hyp, Y, W, T, Q, P, M, I, H, F, E, A, R, or K; and further wherein at least one of the positions $X_4$, $X_{37}$ or $X_{38}$ is not the amino acid present in $hAM_{15-52}$ (SEQ ID NO: 1) in said position.

In a preferred embodiment of the invention relates to an $hAM_{15-52}$ analogue or a pharmaceutically acceptable salt thereof comprising the amino acid sequence of formula (I):

(I) (SEQ ID NO: 408)

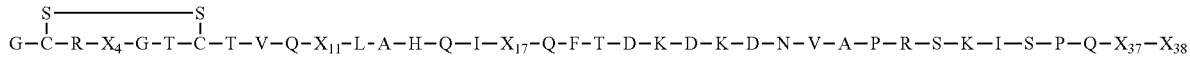

wherein
$X_{11}$ is selected from R, W, or Cit;
$X_{17}$ is selected as Y, W, T, Q, M, I, H, F, A, R, or K;
$X_4$ is selected from F, W, M, I, or C;
$X_{37}$ is selected from G, Y, S, W, T, Q, P, M, I, H, F, E, A, R, C, or K;
$X_{38}$ is selected from Hyp, Y, W, M, or F;
and further wherein at least one of the positions $X_4$, $X_{37}$ or $X_{38}$ is not the amino acid present in $hAM_{15-52}$ (SEQ ID NO: 1) in said position;
or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, more preferably at least 90% homology to $hAM_{15-52}$, most preferably at least 95% homology to $hAM_{15-52}$, wherein $X_{11}$ is selected from R, W, or Cit; $X_{17}$ is selected as Y, W, T, Q, M, I, H, F, A, R, or K; $X_4$ is selected from F, W, M, I, or C; $X_{37}$ is selected from G, Y, S, W, T, Q, P, M, I, H, F, E, A, R, C, or K; $X_{38}$ is selected from Hyp, Y, W, M, or F; and further wherein at least one of the positions $X_4$, $X_{37}$ or $X_{38}$ is not the amino acid present in $hAM_{15-52}$ (SEQ ID NO: 1) in said position.

In a preferred embodiment, the invention relates to an $hAM_{15-52}$ analogue or a pharmaceutically acceptable salt thereof comprising the amino acid sequence of formula (I):

(I) (SEQ ID NO: 409)

wherein
$X_{11}$ is selected from R, W, or Cit;
$X_{17}$ is selected as Y, W, T, Q, M, I, H, F, A, R, or K;
$X_4$ is selected from F, Y, W, T, M, I, A, or C;
$X_{37}$ is selected from G, Y, W, P, H, or F;
$X_{38}$ is selected from Hyp, Y, W, M, or F;
and further wherein at least one of the positions $X_4$, $X_{37}$ or $X_{38}$ is not the amino acid present in $hAM_{15-52}$ (SEQ ID NO: 1) in said position;
or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology to $hAM_{15-52}$, more preferably at least 90% homology to $hAM_{15-52}$, most preferably at least 95% homology to $hAM_{15-52}$, wherein $X_{11}$ is selected from R, W, or Cit; $X_{17}$ is selected as Y, W, T, Q, M, I, H, F, A, R, or K; $X_4$ is selected from F, W, M, I, or C; $X_{37}$ is selected from G, Y, W, P, H, or F; $X_{38}$ is selected from Hyp, Y, W, M, or F; and further wherein at least one of the positions $X_4$, $X_{37}$ or $X_{38}$ is not the amino acid present in $hAM_{15-52}$ (SEQ ID NO: 1) in said position.

In a more preferred embodiment, the invention relates to an $hAM_{15-52}$ analogue or a pharmaceutically acceptable salt thereof comprising the amino acid sequence of formula (I):

(I) (SEQ ID NO: 410)

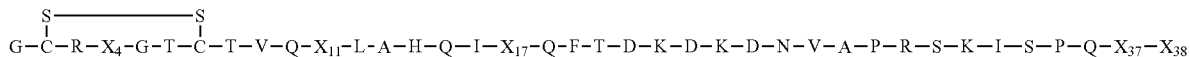

wherein
$X_{11}$ is selected from R, W, or Cit;
$X_{17}$ is selected as Y, W, T, Q, M, I, H, F, A, R, or K;
$X_4$ is selected from F, W, M, I, or C;
$X_{37}$ is selected from G, Y, W, P, H, or F;
$X_{38}$ is selected from Hyp, Y, W, M, or F;
and further wherein at least one of the positions $X_4$, $X_{37}$ or $X_{38}$ is not the amino acid present in $hAM_{15-52}$ (SEQ ID NO: 1) in said position;
or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 85% homology In any of the above-mentioned embodiments, $X_{11}$ is most preferably R, and/or $X_{17}$ is most preferably Y, W, or H. Furthermore, in any of the above-mentioned embodiments, most preferably at least two of the positions $X_4$, $X_{37}$ or $X_{38}$ are not the amino acid present in $hAM_{15-52}$ (SEQ ID NO: 1) in said position.

In a more highly preferred embodiment, the invention relates to an $hAM_{15-52}$ analogue with the sequence SEQ ID NOs: 3-360 or a derivative thereof with at least 50% homology to $hAM_{15-52}$, such as at least 55% homology to $hAM_{15-52}$, such as at least 60% homology to $hAM_{15-52}$, such as at least 65% homology to $hAM_{15-52}$, preferably at least 70% homology to $hAM_{15-52}$, such as at least 75% homology to $hAM_{15-52}$, more preferably at least 80% homology to $hAM_{15-52}$, such as at least 90% homology to $hAM_{15-52}$ (SEQ ID NO: 1), wherein, in the derivative, $X_{11}$ is selected from R, W, or Cit; $X_{17}$ is selected as Y, W, T, Q, M, I, H, F, A, R, or K; $X_4$ is selected from F, Y, W, T, M, I, A, or C; $X_{37}$ is selected from G, Y, S, W, T, Q, P, Mv, I, H, F, E, A, R, C, or K; $X_{38}$ is selected from Hyp, Y, W, T, Q, P, M, I, H, F, E, A, R, or K; and further wherein at least one of the positions $X_4$, $X_{37}$ or $X_{38}$ is not the amino acid present in $hAM_{15-52}$ (SEQ ID NO: 1) in said position.

In yet a more highly preferred embodiment, the invention relates to an $hAM_{15-52}$ analogue with the sequence SEQ ID NOs: 3-360 or a derivative thereof with at least 90% homology (identity) to any one of SEQ ID NO: 3-360, preferably at least 95% homology to any one of SEQ ID NO: 3-360, most preferably at least 97% homology to anyone of SEQ ID NOs: 3-360, with the proviso that in the derivative, $X_{11}$ is selected from R, W, or Cit; $X_{17}$ is selected as Y, W, T, Q, M, I, H, F, A, R, or K; $X_4$ is selected from F, Y, W, T, M, I, A or C; $X_{37}$ is selected from G, Y, S, W, T, Q, P, M, I, H, F, E, A, R, C, or K; $X_{38}$ is selected from Hyp, Y, W, T, Q, P, M, I, H, F, E, A, R, or K; and further wherein at least one of the positions $X_4$, $X_{37}$ or $X_{38}$ is not the amino acid present in $hAM_{15-52}$ (SEQ ID NO: 1) in said position.

In any of the above-mentioned embodiments, $X_4$ is preferably selected as F, W, M, I, or C; $X_{11}$ is preferably selected as R; $X_{37}$ is preferably selected as G, Y, W, P, H, or F; $X_{38}$ is preferably selected as Hyp, Y, W, M, or F; $X_{17}$ is preferably selected as W or H. Furthermore, in any of the above-mentioned embodiments, most preferably at least two of the positions $X_4$, $X_{37}$ or $X_{38}$ is not the amino acid present in $hAM_{15-52}$ (SEQ ID NO: 1) in said position.

In the most preferred embodiment, the invention relates to an $hAM_{15-52}$ analogue with the sequence SEQ ID NOs: 3-360 or a derivative thereof with at least 90% homology (identity) to anyone of SEQ ID NOs: 3-360, preferably at least 95% homology to anyone of SEQ ID NOs: 3-360, most preferably at least 97% homology to anyone of SEQ ID NOs: 3-360, with the proviso that a derivative thereof has the same amino acids in positions $X_4$, $X_{11}$, $X_{37}$, and $X_{38}$, preferably the same amino acids in position $X_4$, $X_{11}$, $X_{17}$, $X_{37}$, and $X_{38}$, as the respective $hAM_{15-52}$ analogue of SEQ ID NO: 3-360 from which it is derived.

Medical Use

In a third aspect, the invention relates to $hAM_{15-52}$ analogues according to the first and/or second aspect for use as a medicament. More particularly, the third aspect of the invention relates to $hAM_{15-52}$ analogues according to the first and/or second aspect for use in treating, preventing or ameliorating a variety of diseases, disorders or conditions, such as but not limited to excess food intake, excess body weight, obesity, Binge eating disorder, Prader-Willi syndrome, dyslipidemia, metabolic diseases/disorders, diabetes I or II, impaired glucose tolerance, insulin resistance syndrome and/or NASH. A preferred embodiment relates to one or more $hAM_{15-52}$ analogue(s) for use in the treatment of obesity, diabetes, NASH or combinations thereof.

Pharmaceutical Positions

In a fourth aspect, the invention relates to pharmaceutical compositions comprising one or more of the $hAM_{15-52}$ analogues according to the first and/or second aspect and their medical use(s) in treating, preventing, or ameliorating a variety of diseases, disorders or conditions according to the third aspect. The pharmaceutical compositions may comprise a pharmaceutically acceptable carrier (vehicle) and/or one or more excipient(s) in accordance with conventional techniques in the art, such as those disclosed in 'Remington: Essentials of Pharmaceutics', Ed. by Linda A. Felton, Pharmaceutical press 2012.

Suitable formulations include but are not limited to tablets, pills, capsules, emulsions, suspensions, sustained release, or solutions. It should be appreciated that different routes of administration may be used depending on the choice of formulation and chemical and/or metabolic stability of the polypeptides. Such administration routes may include but are not limited to oral administration, parenteral administration (intravenous (IV), subcutaneous (SC), intradermal (ID) and intramuscular (IM)), or inhalation. In a preferred embodiment of the invention, the administration route is parental administration. In an even more preferred embodiment, the administration route is subcutaneous.

Method of Treatment

In a fifth aspect, the invention relates to a method of treating a human or animal subject with one or more $hAM_{15-52}$ analogue(s) according to the first and/or second aspect, wherein the human or animal subject is diagnosed with or suffering from one or more of the diseases, disorders according to the third aspect. The method involves administering one or more compounds according to a first and/or second aspect in an effective therapeutic amount to treat diseases, disorders or conditions mentioned in the third aspect. In some instances, a human or animal subject may benefit more from an $hAM_{15-52}$ analogue having potency on both hAMY3R/hAM1R, e.g. when the patient is in high risk of cardiovascular disease and cardioprotective effects are desired. Thus, in an embodiment, the human or animal subject is treated with one or more $hAM_{15-52}$ analogue(s) having mixed hAMY3R/hAM1R potency, such as those exemplified in SEQ ID: 361-392. Likewise, in some instances a human or animal subject may benefit most from a selective hAMY3R $hAM_{15-52}$ analogue. Thus, in an embodiment, the human or animal subject is treated with one or more selective hAMY3R $hAM_{15-52}$ analogue(s), such as those exemplified in SEQ ID: 3-360.

EXAMPLES

General Protocols for Synthesis of the Hybrid Polypeptides

The peptides were synthesized using a SyroII fully automated parallel peptide synthesizer (MultiSynTech GmbH, Germany), equipped with heating block, on Tentagel S RAM with a loading of 0.23-0.25 mmol/g (Rapp polymer GmbH, Germany). $N^α$-Fmoc deprotection was performed in two stages by treating the resin with 40% piperidine/DMF (0.2 M HOBt (1-hydroxybenzotriazole)) for 3 min at 45° C. followed by 20% piperidine/DMF (0.1 M HOBt) for 7-12 min at 75° C. Except Asp, Cys and His residues which were Na-Fmoc deprotections at room temperature; i.e. 40% piperidine/DMF (0.2 M HOBt) for 3 min followed by 20% piperidine/DMF (0.1 M HOBt) for 15 min. The coupling chemistry was DIC (N,N'-diisopropyl-carbodiimide)/Oxyma (ethyl cyano(hydroxyimino)acetate) in DMF using amino acid solutions of 0.5 M in DMF and a molar excess of 6-fold. Standard Fmoc protected amino acids were used. Coupling conditions was single or double couplings for 15 min at 75° C. Except His and Cys residues, which were double coupled for 15 min at 50° C. The Fmoc-amino acids were dissolved at 0.5 M in DMF containing 0.5 M Oxyma, except His which was dissolved in NMP. The resin was washed 4× with NMP after Na-Fmoc deprotection and 3× after couplings.

The disulfide bridge was formed on the resin by using Trityl (Trt) as the protecting group for cysteine and treating with 1% iodine in 75% HFIP (Hexafluoroisopropanol) in DCM for 1 min. The resin was washed 3× with 75% HFIP in DCM followed by 4× DCM.

After synthesis, the resin was washed with DCM and dried, and the polypeptide was cleaved from the resin by a 35 min treatment with TFA (trifluoroacetic acid)/TES (triethylsilane)/water (95/2.5/2.5) at 42° C., followed by precipitation with 4 volumes of cold diethyl ether, further washing with diethyl ether and left to dry.

The peptides were characterized by LC-MS (Waters, Denmark) and quantified by LC-CAD (ThermoFisher scientific, Denmark). Finally, the peptides were freeze dried to give a white powder using a Telstar benchtop freeze drier.

General Protocols for cAMP Assays for Measuring In Vitro Receptor Activation hAMY3-R:

Cells stably overexpressing the hAMY3 receptor were obtained from Ogeda (now Astellas Pharma), sub-cloned and a monoclonal cell-line with an appropriate assay-window was expanded, aliquoted and frozen.

An aliquot was thawed and plated in DPBS with 0.05% casein and 0.5 mM IBMX as 2000 cells/well in a 384-well format. The cells were then immediately stimulated for 30 min at room temperature with graded doses of test compound using human amylin (Bachem, cat no. H-7905) as a positive control. cAMP accumulation was measured using a Cisbio assay for Gs coupled receptors (cat. no. 62AM4PEC), where the assay reagents were added as per the manufacturer's instructions and time-resolved fluorescence energy transfer recorded after one hour.

hAM1-R:

Cells stably overexpressing the hAM1 receptor were obtained from Ogeda (now Astellas Pharma), sub-cloned and a monoclonal cell-line with an appropriate assay-window was expanded, aliquoted and frozen. An aliquot was thawed and plated in DPBS with 0.05% casein and 0.5 mM IBMX as 8000 cells/well in a 384-well format. The cells were then immediately stimulated for 30 min at room temperature with graded doses of test compound using human adrenomedullin 1-52 (Bachem, cat no. H-2932) as a positive control. cAMP accumulation was measured using a Cisbio assay for Gs coupled receptors (cat. no. 62AM4PEC), where the assay reagents were added as per the manufacturer's instructions and time-resolved fluorescence energy transfer recorded after one hour.

General Protocols for Determination of Physical Stability of Peptide Analogues

Peptides were dissolved in buffers (50 mM sodium acetate at pH 4 or 50 mM sodium phosphate at pH 7) and incubated for one hour. The samples were then divided into two replicates of 80 µl in a black 384 well plate (µ-clear, Greiner Bio-One) and mixed with Thioflavin T (ThT) to a final concentration of 4 µM. The plate was sealed and placed in a plate reader (CLARIOstar, BMG) where the temperature was set at 40° C. during the course of the experiment. The samples were further stressed by shaking the plate at 700 rpm (linear) for five minutes before every measurement. The fluorescence was measured every 10 min for four days by exciting the ThT at 450 nm and measuring the emission at 480 nm. For each peptide, the ThT signal over time was smoothened using Local Polynomial Regression fitting (LOESS) as implemented in the statistical programming environment R. For the smoothened data, the maximum ThT signal was normalized in percent between the maximum ThT signal for hAMY and the buffer background. Thus, high values indicate fibrillation properties similar to hAMY while low values indicate no fibrillation.

General Protocols for Acute Food Intake Study

The effect on cumulative food intake was measured in in male Sprague Dawley rats (6 weeks of age, Taconic, Denmark) following a single dose using a fully automated food intake monitoring system (HM-2; MBRose ApS, Faaborg, Denmark), allowing for advanced synchronous real-time monitoring of food intake behaviour of individual animals. The animals were housed in groups of 4 in a light-, temperature-, and humidity-controlled room (a 12/12 LD cycle, lights on at 02:00 AM; 22±2° C.; 50% relative humidity). The mice had ad libitum access to regular chow diet (Altromin 1324, Brogaarden A/S, Lynge, Denmark) and domestic quality tap water. Mice arrived at day 7, and a minimum of 5 days of habituation to the system was allowed prior to beginning of the study. During these days, the animals were handled daily to accustom them to the experimental paradigm. On the day of dosing, the animals were randomized into groups according to body weight. Animals were fasted for four hours prior to dosing. Animals were dosed SC 30 or 180 min prior to lights out, and food intake data were collected automatically for a total of 48 h post-dosing with automatic food recordings every 5 min.

General Protocols for Chronic Diet-Induced Obesity (DIO) Study

Sprague-Dawley rats (Taconic, Denmark) arrived at the age of 5 weeks. After one week of acclimation, they were evenly grouped based on their baseline body weight and offered ad libitum access a two-choice diet consisting of chow pellet (Altromin #1324, Brogaarden, Lynge, Denmark) and a high palatable high sugar/fat diet (1:1:1 mixture of Nutella (Ferrero, Alba, Italy), peanut butter (PCD, Rotterdam, Netherlands) and powdered standard chow (Altromin #1324, Brogaarden, Lynge, Denmark); 29.3% fat, 33.2% carbohydrate, and 18% protein) for up to 36 weeks. The rats were pair-housed throughout the study under controlled environmental conditions (12-hour light/dark cycle, lights off at 15:00; 22±1° C.; 50±10% relative humidity). Body weight, food and water intake were monitored daily during the entire period of the study. One day before the experiment, the rats were randomized according to body weight into experimental groups (n=9-10), which received compound or vehicle SC. QD (once daily) for 28 days.

Example 1

$EC_{50}$ values at hAMY3R and hAM1R were measured according to the general protocol above. Percent homology (identity) for the $hAM_{15-52}$ analogues were calculated in comparison to $hAM_{15-52}$. The results are summarized in Table 2 below.

TABLE 2

Table 2 shows that hAM$_{15-52}$ analogues (SEQ ID NO: 3-392) with improved hAMY3R potency compared to hAM$_{15-52}$ may be obtained by changing the amino acid K present in hAM$_{15-52}$ in position X$_{11}$ into R, W or Cit. Table 2 further shows that highly selective (hAMY3R-EC$_{50}$ ≤ 250 pM and an hAM1R-EC$_{50}$ ≥ 25 nM) hAMY3R hAM$_{15-52}$ analogues (SEQ ID NO: 3-360) may be obtained by abolishing or reducing the hAM1R potency using the positions X$_4$, X$_{37}$ and/or X$_{38}$. All lipidations at position 1 were performed at the N-terminal and the lipidation in the other positions were performed at an epsilon N in Lys.

| ID | hAMY3R EC$_{50}$ (nM) | hAM1R EC$_{50}$ (nM) | identity (% ADM)* | Lipidation | Lipidation position |
|---|---|---|---|---|---|
| 1 | 1.274 | 1.113 | 100.0 | None | NA |
| 2 | 0.01 | >5000.000 | 18.4 | None | NA |
| 3 | 0.006 | 123.548 | 73.7 | None | NA |
| 4 | 0.006 | >5000.000 | 63.2 | C20DA-yGlu | 1 |
| 5 | 0.006 | >5000.000 | 63.2 | C20DA-yGlu | 1 |
| 6 | 0.006 | >5000.000 | 63.2 | C20DA-yGlu-OEG-OEG | 36 |
| 7 | 0.006 | >5000.000 | 63.2 | None | NA |
| 8 | 0.006 | >5000.000 | 44.7 | None | NA |
| 9 | 0.006 | >5000.000 | 44.7 | None | NA |
| 10 | 0.007 | 551.970 | 68.4 | None | NA |
| 11 | 0.007 | >5000.000 | 63.2 | C20DA-yGlu | 1 |
| 12 | 0.007 | >5000.000 | 60.5 | C20DA-yGlu-OEG-OEG | 27 |
| 13 | 0.007 | >5000.000 | 63.2 | None | NA |
| 14 | 0.007 | >5000.000 | 63.2 | None | NA |
| 15 | 0.007 | >5000.000 | 50.0 | None | NA |
| 16 | 0.008 | 125.467 | 78.9 | None | NA |
| 17 | 0.008 | 294.942 | 71.1 | None | NA |
| 18 | 0.008 | 817.242 | 68.4 | None | NA |
| 19 | 0.008 | >5000.000 | 28.9 | None | NA |
| 20 | 0.008 | >5000.000 | 71.1 | None | NA |
| 21 | 0.008 | >5000.000 | 63.2 | C20DA-yGlu | 1 |
| 22 | 0.008 | >5000.000 | 63.2 | C20DA-yGlu | 1 |
| 23 | 0.008 | >5000.000 | 63.2 | None | NA |
| 24 | 0.008 | >5000.000 | 63.2 | None | NA |
| 25 | 0.008 | >5000.000 | 63.2 | None | NA |
| 26 | 0.008 | >5000.000 | 63.2 | None | NA |
| 27 | 0.008 | >5000.000 | 63.2 | None | NA |
| 28 | 0.008 | >5000.000 | 65.8 | None | NA |
| 29 | 0.008 | >5000.000 | 55.3 | None | NA |
| 30 | 0.008 | >5000.000 | 63.2 | None | NA |
| 31 | 0.008 | >5000.000 | 60.5 | None | NA |
| 32 | 0.008 | >5000.000 | 50.0 | None | NA |
| 33 | 0.008 | >5000.000 | 52.6 | None | NA |
| 34 | 0.009 | 54.627 | 73.7 | None | NA |
| 35 | 0.009 | >5000.000 | 63.2 | C20DA-yGlu | 1 |
| 36 | 0.009 | >5000.000 | 63.2 | C20DA-yGlu-OEG-OEG | 3 |
| 37 | 0.010 | >5000.000 | 63.2 | C20DA-yGlu | 1 |
| 38 | 0.010 | >5000.000 | 63.2 | C20DA-yGlu | 1 |
| 39 | 0.010 | >5000.000 | 65.8 | C20DA-yGlu | 1 |
| 40 | 0.010 | >5000.000 | 60.5 | C20DA-yGlu-OEG-OEG | 25 |
| 41 | 0.010 | >5000.000 | 60.5 | C20DA-yGlu-OEG-OEG | 26 |
| 42 | 0.010 | >5000.000 | 63.2 | None | NA |
| 43 | 0.010 | >5000.000 | 63.2 | None | NA |
| 44 | 0.010 | >5000.000 | 63.2 | None | NA |
| 45 | 0.011 | 50.470 | 86.8 | None | NA |
| 46 | 0.011 | 78.480 | 86.8 | None | NA |
| 47 | 0.011 | 500.000 | 63.2 | C20DA-yGlu | 1 |
| 48 | 0.011 | 760.539 | 63.2 | C20DA-yGlu | 1 |
| 49 | 0.011 | 2981.000 | 81.6 | None | NA |
| 50 | 0.011 | >5000.000 | 65.8 | C20DA-yGlu | 1 |
| 51 | 0.011 | >5000.000 | 63.2 | C20DA-yGlu | 1 |
| 52 | 0.011 | >5000.000 | 63.2 | None | NA |
| 53 | 0.011 | >5000.000 | 63.2 | None | NA |
| 54 | 0.012 | 46.194 | 81.6 | None | NA |
| 55 | 0.012 | 63.776 | 63.2 | C20DA-yGlu | 1 |
| 56 | 0.012 | 103.250 | 73.7 | None | NA |
| 57 | 0.012 | 590.397 | 63.2 | C20DA-yGlu | 1 |
| 58 | 0.012 | >5000.000 | 21.1 | None | NA |
| 59 | 0.012 | >5000.000 | 26.3 | None | NA |
| 60 | 0.012 | >5000.000 | 68.4 | C20DA-yGlu | 1 |
| 61 | 0.012 | >5000.000 | 63.2 | C20DA-yGlu | 1 |
| 62 | 0.012 | >5000.000 | 63.2 | C20DA-yGlu | 1 |
| 63 | 0.012 | >5000.000 | 63.2 | C20DA-yGlu | 1 |
| 64 | 0.012 | >5000.000 | 63.2 | None | NA |
| 65 | 0.012 | >5000.000 | 57.9 | None | NA |
| 66 | 0.012 | >5000.000 | 60.5 | None | NA |
| 67 | 0.013 | 116.497 | 71.1 | C20DA-yGlu | 1 |
| 68 | 0.013 | 254.722 | 68.4 | C20DA-yGlu | 1 |
| 69 | 0.013 | 680.331 | 60.5 | C20DA-yGlu | 1 |
| 70 | 0.013 | 2981.000 | 84.2 | None | NA |
| 71 | 0.013 | >5000.000 | 60.5 | C20DA-yGlu | 1 |
| 72 | 0.013 | >5000.000 | 63.2 | C20DA-yGlu | 1 |
| 73 | 0.013 | >5000.000 | 63.2 | C20DA-yGlu | 1 |
| 74 | 0.013 | >5000.000 | 63.2 | C20DA-yGlu-OEG-OEG | 14 |
| 75 | 0.013 | >5000.000 | 65.8 | None | NA |
| 76 | 0.014 | >5000.000 | 13.2 | C20DA-yGlu | 1 |
| 77 | 0.014 | >5000.000 | 65.8 | C20DA-yGlu | 1 |
| 78 | 0.014 | >5000.000 | 60.5 | C20DA-yGlu | 1 |
| 79 | 0.014 | >5000.000 | 60.5 | C20DA-yGlu | 1 |
| 80 | 0.015 | 44.303 | 15.8 | C20DA-yGlu | 1 |
| 81 | 0.015 | 138.500 | 84.2 | None | NA |
| 82 | 0.015 | 612.158 | 63.2 | C20DA-yGlu | 1 |
| 83 | 0.015 | 815.473 | 63.2 | C20DA-yGlu | 1 |
| 84 | 0.015 | 2981.000 | 81.6 | None | NA |
| 85 | 0.015 | >5000.000 | 63.2 | C20DA-yGlu | 1 |

TABLE 2-continued

Table 2 shows that hAM$_{15-52}$ analogues (SEQ ID NO: 3-392) with improved hAMY3R potency compared to hAM$_{15-52}$ may be obtained by changing the amino acid K present in hAM$_{15-52}$ in position $X_{11}$ into R, W or Cit. Table 2 further shows that highly selective (hAMY3R-EC$_{50}$ ≤ 250 pM and an hAM1R-EC$_{50}$ ≥ 25 nM) hAMY3R hAM$_{15-52}$ analogues (SEQ ID NO: 3-360) may be obtained by abolishing or reducing the hAM1R potency using the positions $X_4$, $X_{37}$ and/or $X_{38}$. All lipidations at position 1 were performed at the N-terminal and the lipidation in the other positions were performed at an epsilon N in Lys.

| ID | hAMY3R EC$_{50}$ (nM) | hAM1R EC$_{50}$ (nM) | identity (% ADM)* | Lipidation | Lipidation position |
|---|---|---|---|---|---|
| 86 | 0.015 | >5000.000 | 60.5 | C20DA-yGlu | 1 |
| 87 | 0.015 | >5000.000 | 60.5 | C20DA-yGlu | 1 |
| 88 | 0.015 | >5000.000 | 60.5 | C20DA-yGlu | 1 |
| 89 | 0.015 | >5000.000 | 60.5 | C20DA-yGlu-OEG-OEG | 20 |
| 90 | 0.016 | 58.530 | 81.6 | None | NA |
| 91 | 0.016 | 839.591 | 63.2 | C20DA-yGlu | 1 |
| 92 | 0.016 | 932.795 | 60.5 | C20DA-yGlu | 1 |
| 93 | 0.016 | >5000.000 | 28.9 | None | NA |
| 94 | 0.016 | >5000.000 | 60.5 | C20DA-yGlu | 1 |
| 95 | 0.016 | >5000.000 | 60.5 | C20DA-yGlu | 1 |
| 96 | 0.016 | >5000.000 | 60.5 | C20DA-yGlu | 1 |
| 97 | 0.016 | >5000.000 | 63.2 | C20DA-yGlu | 1 |
| 98 | 0.017 | 66.880 | 86.8 | None | NA |
| 99 | 0.017 | 364.198 | 71.1 | C20DA-yGlu | 1 |
| 100 | 0.017 | >5000.000 | 60.5 | C20DA-yGlu | 1 |
| 101 | 0.017 | >5000.000 | 63.2 | None | NA |
| 102 | 0.018 | >5000.000 | 71.1 | None | NA |
| 103 | 0.018 | >5000.000 | 63.2 | C20DA-yGlu | 1 |
| 104 | 0.018 | >5000.000 | 63.2 | C20DA-yGlu | 1 |
| 105 | 0.018 | >5000.000 | 60.5 | C20DA-yGlu | 1 |
| 106 | 0.018 | >5000.000 | 60.5 | C20DA-yGlu | 1 |
| 107 | 0.019 | 646.950 | 60.5 | C20DA-yGlu | 1 |
| 108 | 0.019 | >5000.000 | 60.5 | C20DA-yGlu | 1 |
| 109 | 0.020 | 2981.000 | 84.2 | None | NA |
| 110 | 0.020 | >5000.000 | 63.2 | C20DA-yGlu | 1 |
| 111 | 0.021 | 2981.000 | 89.5 | None | NA |
| 112 | 0.021 | >5000.000 | 60.5 | C20DA-yGlu | 1 |
| 113 | 0.022 | 2981.000 | 89.5 | None | NA |
| 114 | 0.022 | >5000.000 | 63.2 | None | NA |
| 115 | 0.023 | 129.800 | 84.2 | None | NA |
| 116 | 0.024 | 48.170 | 89.5 | None | NA |
| 117 | 0.024 | 51.555 | 78.9 | None | NA |
| 118 | 0.024 | 2981.000 | 84.2 | None | NA |
| 119 | 0.024 | >5000.000 | 65.8 | C20DA-yGlu | 1 |
| 120 | 0.025 | >5000.000 | 57.9 | C20DA-yGlu | 1 |
| 121 | 0.026 | 2981.000 | 84.2 | None | NA |
| 122 | 0.026 | >5000.000 | 60.5 | C20DA-yGlu | 1 |
| 123 | 0.027 | 31.653 | 73.7 | None | NA |
| 124 | 0.027 | 34.840 | 86.8 | None | NA |
| 125 | 0.027 | 2981.000 | 86.8 | None | NA |
| 126 | 0.027 | >5000.000 | 63.2 | C20DA-AMCHC-yGlu-OEG-OEG | 1 |
| 127 | 0.028 | 107.400 | 92.1 | None | NA |
| 128 | 0.028 | 130.300 | 34.2 | None | NA |
| 129 | 0.029 | 366.900 | 89.5 | None | NA |
| 130 | 0.030 | >5000.000 | 57.9 | C20DA-yGlu | 1 |
| 131 | 0.031 | 33.760 | 92.1 | None | NA |
| 132 | 0.031 | 2981.000 | 89.5 | None | NA |
| 133 | 0.031 | >5000.000 | 57.9 | C20DA-yGlu | 1 |
| 134 | 0.032 | 2981.000 | 86.8 | None | NA |
| 135 | 0.033 | 68.400 | 86.8 | None | NA |
| 136 | 0.033 | >5000.000 | 60.5 | C20DA-yGlu-OEG-OEG | 17 |
| 137 | 0.034 | >5000.000 | 57.9 | C20DA-yGlu | 1 |
| 138 | 0.035 | 2981.000 | 86.8 | None | NA |
| 139 | 0.035 | 2981.000 | 84.2 | None | NA |
| 140 | 0.036 | 31.400 | 92.1 | None | NA |
| 141 | 0.036 | 258.400 | 89.5 | None | NA |
| 142 | 0.036 | 2981.000 | 84.2 | None | NA |
| 143 | 0.038 | 2981.000 | 84.2 | None | NA |
| 144 | 0.038 | >5000.000 | 57.9 | C20DA-yGlu | 1 |
| 145 | 0.039 | 2981.000 | 89.5 | None | NA |
| 146 | 0.040 | 2981.000 | 92.1 | None | NA |
| 147 | 0.040 | 3108.878 | 86.8 | None | NA |
| 148 | 0.040 | >5000.000 | 26.3 | None | NA |
| 149 | 0.040 | >5000.000 | 28.9 | None | NA |
| 150 | 0.040 | >5000.000 | 89.5 | None | NA |
| 151 | 0.041 | 44.920 | 84.2 | None | NA |
| 152 | 0.041 | 212.700 | 89.5 | None | NA |
| 153 | 0.041 | >5000.000 | 60.5 | C20DA-yGlu | 1 |
| 154 | 0.042 | 2981.000 | 97.4 | None | NA |
| 155 | 0.045 | 116.500 | 92.1 | None | NA |
| 156 | 0.047 | 2981.000 | 86.8 | None | NA |
| 157 | 0.047 | 2981.000 | 86.8 | None | NA |
| 158 | 0.048 | 2981.000 | 92.1 | None | NA |
| 159 | 0.048 | >5000.000 | 63.2 | C20DA-yGlu | 1 |
| 160 | 0.050 | 2981.000 | 86.8 | None | NA |
| 161 | 0.051 | 2981.000 | 86.8 | None | NA |
| 162 | 0.051 | >5000.000 | 31.6 | None | NA |
| 163 | 0.053 | 2981.000 | 81.6 | None | NA |
| 164 | 0.054 | 106.200 | 94.7 | None | NA |
| 165 | 0.054 | 2981.000 | 86.8 | None | NA |
| 166 | 0.056 | 2981.000 | 84.2 | None | NA |
| 167 | 0.056 | 2981.000 | 92.1 | None | NA |
| 168 | 0.062 | >5000.000 | 92.1 | None | NA |
| 169 | 0.063 | 2981.000 | 94.7 | None | NA |
| 170 | 0.064 | 2981.000 | 84.2 | None | NA |
| 171 | 0.064 | >5000.000 | 86.8 | None | NA |
| 172 | 0.066 | 2981.000 | 86.8 | None | NA |
| 173 | 0.069 | >5000.000 | 86.8 | None | NA |
| 174 | 0.071 | 133.300 | 94.7 | None | NA |
| 175 | 0.074 | 2981.000 | 89.5 | None | NA |
| 176 | 0.076 | 2981.000 | 86.8 | None | NA |
| 177 | 0.077 | 2981.000 | 84.2 | None | NA |
| 178 | 0.080 | 2981.000 | 84.2 | None | NA |
| 179 | 0.082 | 2981.000 | 89.5 | None | NA |
| 180 | 0.082 | >5000.000 | 26.3 | None | NA |
| 181 | 0.082 | >5000.000 | 63.2 | None | NA |
| 182 | 0.085 | 100.100 | 94.7 | None | NA |

TABLE 2-continued

Table 2 shows that hAM$_{15-52}$ analogues (SEQ ID NO: 3-392) with improved hAMY3R potency compared to hAM$_{15-52}$ may be obtained by changing the amino acid K present in hAM$_{15-52}$ in position $X_{11}$ into R, W or Cit. Table 2 further shows that highly selective (hAMY3R-EC$_{50}$ ≤ 250 pM and an hAM1R-EC$_{50}$ ≥ 25 nM) hAMY3R hAM$_{15-52}$ analogues (SEQ ID NO: 3-360) may be obtained by abolishing or reducing the hAM1R potency using the positions $X_4$, $X_{37}$ and/or $X_{38}$. All lipidations at position 1 were performed at the N-terminal and the lipidation in the other positions were performed at an epsilon N in Lys.

| ID | hAMY3R EC$_{50}$ (nM) | hAM1R EC$_{50}$ (nM) | identity (% ADM)* | Lipidation | Lipidation position |
|---|---|---|---|---|---|
| 183 | 0.088 | 2981.000 | 89.5 | None | NA |
| 184 | 0.090 | 4495.564 | 86.8 | None | NA |
| 185 | 0.090 | >5000.000 | 86.8 | None | NA |
| 186 | 0.091 | >5000.000 | 86.8 | None | NA |
| 187 | 0.093 | 2981.000 | 86.8 | None | NA |
| 188 | 0.094 | 47.640 | 86.8 | None | NA |
| 189 | 0.096 | 2981.000 | 89.5 | None | NA |
| 190 | 0.097 | 2981.000 | 89.5 | None | NA |
| 191 | 0.098 | 2981.000 | 89.5 | None | NA |
| 192 | 0.098 | >5000.000 | 86.8 | None | NA |
| 193 | 0.099 | >5000.000 | 84.2 | None | NA |
| 194 | 0.112 | 3526.547 | 86.8 | None | NA |
| 195 | 0.112 | >5000.000 | 60.5 | None | NA |
| 196 | 0.114 | >5000.000 | 84.2 | None | NA |
| 197 | 0.120 | 2981.000 | 86.8 | None | NA |
| 198 | 0.122 | 3962.089 | 86.8 | None | NA |
| 199 | 0.124 | 2981.000 | 89.5 | None | NA |
| 200 | 0.126 | 38.156 | 81.6 | C20DA-yGlu | 1 |
| 201 | 0.126 | 4881.061 | 86.8 | None | NA |
| 202 | 0.126 | >5000.000 | 86.8 | None | NA |
| 203 | 0.127 | >5000.000 | 86.8 | None | NA |
| 204 | 0.129 | 2981.000 | 86.8 | None | NA |
| 205 | 0.130 | 3228.702 | 89.5 | None | NA |
| 206 | 0.130 | >5000.000 | 86.8 | None | NA |
| 207 | 0.131 | >5000.000 | 28.9 | None | NA |
| 208 | 0.133 | 242.450 | 73.7 | C20DA-yGlu | 1 |
| 209 | 0.136 | 1020.000 | 89.5 | None | NA |
| 210 | 0.137 | >5000.000 | 63.2 | None | NA |
| 211 | 0.151 | 2756.647 | 86.8 | None | NA |
| 212 | 0.153 | >5000.000 | 89.5 | None | NA |
| 213 | 0.153 | >5000.000 | 84.2 | None | NA |
| 214 | 0.157 | 2981.000 | 86.8 | None | NA |
| 215 | 0.161 | >5000.000 | 86.8 | None | NA |
| 216 | 0.164 | 2981.000 | 86.8 | None | NA |
| 217 | 0.167 | >5000.000 | 89.5 | None | NA |
| 218 | 0.169 | >5000.000 | 86.8 | None | NA |
| 219 | 0.171 | 4246.488 | 86.8 | None | NA |
| 220 | 0.182 | >5000.000 | 86.8 | None | NA |
| 221 | 0.184 | >5000.000 | 63.2 | C20DA-AMCHC-gGlu-OEG-OEG-K(C20DA-AMCHC-gGlu-OEG-OEG) | 1 |
| 222 | 0.184 | >5000.000 | 86.8 | None | NA |
| 223 | 0.186 | 47.652 | 78.9 | C20DA-yGlu | 1 |
| 224 | 0.186 | 2981.000 | 86.8 | None | NA |
| 225 | 0.186 | >5000.000 | 65.8 | C20DA-yGlu | 1 |
| 226 | 0.186 | >5000.000 | 86.8 | None | NA |
| 227 | 0.187 | 4570.819 | 84.2 | None | NA |
| 228 | 0.205 | >5000.000 | 86.8 | None | NA |
| 229 | 0.207 | 2981.000 | 89.5 | None | NA |
| 230 | 0.208 | >5000.000 | 89.5 | None | NA |
| 231 | 0.209 | >5000.000 | 65.8 | C20DA-yGlu | 1 |
| 232 | 0.213 | >5000.000 | 86.8 | None | NA |
| 233 | 0.220 | >5000.000 | 63.2 | (C20DA-OEG-yGlu-OEG)$_2$-K- | 1 |
| 234 | 0.227 | >5000.000 | 71.1 | None | NA |
| 235 | 0.233 | 1416.600 | 86.8 | None | NA |
| 236 | 0.234 | 2239.417 | 86.8 | None | NA |
| 237 | 0.235 | 4245.930 | 86.8 | None | NA |
| 238 | 0.235 | >5000.000 | 86.8 | None | NA |
| 239 | 0.236 | >5000.000 | 86.8 | None | NA |
| 240 | 0.240 | >5000.000 | 89.5 | None | NA |
| 241 | 0.242 | 2291.534 | 86.8 | None | NA |
| 242 | 0.248 | >5000.000 | 86.8 | None | NA |
| 243 | 0.018 | 3336.098 | 63.2 | None | NA |
| 244 | 0.006 | >5000.000 | 44.7 | None | NA |
| 245 | 0.017 | >5000.000 | 44.7 | None | NA |
| 246 | 0.010 | >5000.000 | 63.2 | None | NA |
| 247 | 0.004 | >5000.000 | 50.0 | None | NA |
| 248 | 0.027 | 3587.646 | 71.1 | None | NA |
| 249 | 0.006 | >5000.000 | 63.2 | None | NA |
| 250 | 0.011 | >5000.000 | 63.2 | None | NA |
| 251 | 0.006 | >5000.000 | 63.2 | None | NA |
| 252 | 0.006 | >5000.000 | 65.8 | None | NA |
| 253 | 0.004 | >5000.000 | 60.5 | None | NA |
| 254 | 0.006 | >5000.000 | 63.2 | None | NA |
| 255 | 0.007 | >5000.000 | 65.8 | None | NA |
| 256 | 0.007 | >5000.000 | 50.0 | None | NA |
| 257 | 0.016 | 2037.788 | 73.7 | None | NA |
| 258 | 0.010 | >5000.000 | 63.2 | None | NA |
| 259 | 0.013 | 4324.040 | 86.8 | None | NA |
| 260 | 0.011 | 4163.023 | 86.8 | None | NA |
| 261 | 0.018 | >5000.000 | 81.6 | None | NA |
| 262 | 0.014 | >5000.000 | 63.2 | None | NA |
| 263 | 0.005 | 1283.849 | 81.6 | None | NA |
| 264 | 0.006 | 3469.936 | 73.7 | None | NA |
| 265 | 0.030 | >5000.000 | 63.2 | None | NA |
| 266 | 0.053 | >5000.000 | 60.5 | None | NA |
| 267 | 0.007 | 2490.994 | 84.2 | None | NA |
| 268 | 0.014 | >5000.000 | 65.8 | None | NA |
| 269 | 0.005 | >5000.000 | 81.6 | None | NA |
| 270 | 0.003 | 1877.713 | 81.6 | None | NA |
| 271 | 0.010 | 96.618 | 86.8 | None | NA |
| 272 | 0.009 | >5000.000 | 71.1 | None | NA |
| 273 | 0.021 | >5000.000 | 84.2 | None | NA |
| 274 | 0.019 | 877.430 | 89.5 | None | NA |
| 275 | 0.020 | >5000.000 | 89.5 | None | NA |
| 276 | 0.056 | >5000.000 | 63.2 | None | NA |
| 277 | 0.058 | >5000.000 | 84.2 | None | NA |
| 278 | 0.011 | 154.831 | 89.5 | None | NA |
| 279 | 0.013 | 241.240 | 78.9 | None | NA |
| 280 | 0.024 | >5000.000 | 84.2 | None | NA |
| 281 | 0.034 | >5000.000 | 84.2 | None | NA |
| 282 | 0.143 | 3880.504 | 73.7 | None | NA |
| 283 | 0.035 | >5000.000 | 86.8 | None | NA |
| 284 | 0.028 | 590.750 | 92.1 | None | NA |
| 285 | 0.157 | >5000.000 | 89.5 | None | NA |
| 286 | 0.025 | 138.873 | 92.1 | None | NA |
| 287 | 0.055 | >5000.000 | 89.5 | None | NA |
| 288 | 0.030 | >5000.000 | 86.8 | None | NA |
| 289 | 0.005 | 3502.991 | 86.8 | None | NA |
| 290 | 0.047 | >5000.000 | 84.2 | None | NA |
| 291 | 0.064 | >5000.000 | 89.5 | None | NA |
| 292 | 0.070 | >5000.000 | 84.2 | None | NA |
| 293 | 0.063 | >5000.000 | 89.5 | None | NA |
| 294 | 0.045 | >5000.000 | 92.1 | None | NA |
| 295 | 0.194 | >5000.000 | 86.8 | None | NA |
| 296 | 0.392 | >5000.000 | 89.5 | None | NA |
| 297 | 0.026 | >5000.000 | 84.2 | None | NA |
| 298 | 0.057 | >5000.000 | 86.8 | None | NA |
| 299 | 0.110 | >5000.000 | 86.8 | None | NA |
| 300 | 0.076 | >5000.000 | 92.1 | None | NA |

TABLE 2-continued

Table 2 shows that hAM$_{15-52}$ analogues (SEQ ID NO: 3-392) with improved hAMY3R potency compared to hAM$_{15-52}$ may be obtained by changing the amino acid K present in hAM$_{15-52}$ in position $X_{11}$ into R, W or Cit. Table 2 further shows that highly selective (hAMY3R-EC$_{50}$ ≤ 250 pM and an hAM1R-EC$_{50}$ ≥ 25 nM) hAMY3R hAM$_{15-52}$ analogues (SEQ ID NO: 3-360) may be obtained by abolishing or reducing the hAM1R potency using the positions $X_4$, $X_{37}$ and/or $X_{38}$. All lipidations at position 1 were performed at the N-terminal and the lipidation in the other positions were performed at an epsilon N in Lys.

| ID | hAMY3R EC$_{50}$ (nM) | hAM1R EC$_{50}$ (nM) | identity (% ADM)* | Lipidation | Lipidation position |
|---|---|---|---|---|---|
| 301 | 0.138 | >5000.000 | 86.8 | None | NA |
| 302 | 0.071 | 4332.084 | 81.6 | None | NA |
| 303 | 0.103 | >5000.000 | 86.8 | None | NA |
| 304 | 0.139 | >5000.000 | 84.2 | None | NA |
| 305 | 0.085 | >5000.000 | 92.1 | None | NA |
| 306 | 0.003 | >5000.000 | 44.7 | None | NA |
| 307 | 0.010 | >5000.000 | 44.7 | None | NA |
| 308 | 0.014 | >5000.000 | 63.2 | None | NA |
| 309 | 0.025 | >5000.000 | 63.2 | None | NA |
| 310 | 0.003 | >5000.000 | 50.0 | None | NA |
| 311 | 0.060 | >5000.000 | 78.9 | None | NA |
| 312 | 0.012 | >5000.000 | 71.1 | None | NA |
| 313 | 0.004 | >5000.000 | 63.2 | None | NA |
| 314 | 0.008 | >5000.000 | 63.2 | None | NA |
| 315 | 0.012 | >5000.000 | 63.2 | None | NA |
| 316 | 0.012 | >5000.000 | 65.8 | None | NA |
| 317 | 0.004 | >5000.000 | 60.5 | None | NA |
| 318 | 0.009 | >5000.000 | 63.2 | None | NA |
| 319 | 0.018 | >5000.000 | 65.8 | None | NA |
| 320 | 0.009 | >5000.000 | 63.2 | None | NA |
| 321 | 0.317 | >5000.000 | 63.2 | None | NA |
| 322 | 0.014 | 1390.178 | 86.8 | None | NA |
| 323 | 0.014 | >5000.000 | 81.6 | None | NA |
| 324 | 0.028 | >5000.000 | 63.2 | None | NA |
| 325 | 0.025 | >5000.000 | 63.2 | None | NA |
| 326 | 0.053 | >5000.000 | 81.6 | None | NA |
| 327 | 0.090 | >5000.000 | 73.7 | None | NA |
| 328 | 0.010 | >5000.000 | 63.2 | None | NA |
| 329 | 0.032 | >5000.000 | 63.2 | None | NA |
| 330 | 0.008 | >5000.000 | 65.8 | None | NA |
| 331 | 0.006 | 3566.754 | 84.2 | None | NA |
| 332 | 0.007 | >5000.000 | 81.6 | None | NA |
| 333 | 0.236 | 107.471 | 63.2 | None | NA |
| 334 | 0.013 | >5000.000 | 71.1 | None | NA |
| 335 | 0.015 | >5000.000 | 84.2 | None | NA |
| 336 | 0.029 | 738.478 | 89.5 | None | NA |
| 337 | 0.019 | 1583.677 | 89.5 | None | NA |
| 338 | 0.089 | >5000.000 | 63.2 | None | NA |
| 339 | 0.047 | >5000.000 | 84.2 | None | NA |
| 340 | 0.022 | 671.058 | 89.5 | None | NA |
| 341 | 0.029 | >5000.000 | 84.2 | None | NA |
| 342 | 0.054 | >5000.000 | 84.2 | None | NA |
| 343 | 0.017 | 117.363 | 86.8 | None | NA |
| 344 | 0.121 | >5000.000 | 89.5 | None | NA |
| 345 | 0.051 | 113.116 | 92.1 | None | NA |
| 346 | 0.085 | >5000.000 | 86.8 | None | NA |
| 347 | 0.068 | >5000.000 | 84.2 | None | NA |
| 348 | 0.041 | >5000.000 | 84.2 | None | NA |
| 349 | 0.046 | >5000.000 | 84.2 | None | NA |
| 350 | 0.044 | 1180.470 | 92.1 | None | NA |
| 351 | 0.943 | >5000.000 | 86.8 | None | NA |
| 352 | 0.040 | 1116.41 | 84.2 | None | NA |
| 353 | 0.027 | 2918.91 | 89.5 | None | NA |
| 354 | 0.091 | >5000.000 | 86.8 | None | NA |
| 355 | 0.140 | >5000.000 | 86.8 | None | NA |
| 356 | 0.079 | >5000.000 | 86.8 | None | NA |
| 357 | 0.115 | >5000.000 | 86.8 | None | NA |
| 358 | 0.071 | >5000.000 | 81.6 | None | NA |
| 359 | 0.145 | >5000.000 | 86.8 | None | NA |
| 360 | 0.165 | >5000.000 | 842 | None | NA |
| 361 | 0.006 | 0.913 | 76.3 | None | NA |
| 362 | 0.007 | 18.150 | 86.8 | None | NA |
| 363 | 0.010 | 1.771 | 71.1 | None | NA |
| 364 | 0.010 | 13.585 | 84.2 | None | NA |
| 365 | 0.012 | 1.211 | 86.8 | None | NA |
| 366 | 0.013 | 12.090 | 89.5 | None | NA |
| 367 | 0.014 | 0.563 | 89.5 | None | NA |
| 368 | 0.015 | 0.997 | 89.5 | None | NA |
| 369 | 0.017 | 2.477 | 84.2 | None | NA |
| 370 | 0.017 | 10.304 | 73.7 | C20DA-yGlu | 1 |
| 371 | 0.019 | 3.029 | 92.1 | None | NA |
| 372 | 0.020 | 3.941 | 84.2 | C20DA-yGlu | 1 |
| 373 | 0.020 | 7.712 | 86.8 | None | NA |
| 374 | 0.021 | 12.000 | 89.5 | None | NA |
| 375 | 0.022 | 0.403 | 92.1 | None | NA |
| 376 | 0.022 | 12.022 | 81.6 | None | NA |
| 377 | 0.024 | 0.243 | 81.6 | None | NA |
| 378 | 0.027 | 0.893 | 76.3 | C20DA-yGlu | 1 |
| 379 | 0.029 | 0.458 | 89.5 | None | NA |
| 380 | 0.031 | 0.162 | 86.8 | C20DA-yGlu | 1 |
| 381 | 0.032 | 7.608 | 86.8 | None | NA |
| 382 | 0.034 | 5.124 | 92.1 | None | NA |
| 383 | 0.034 | 5.935 | 92.1 | None | NA |
| 384 | 0.036 | 1.090 | 92.1 | None | NA |
| 385 | 0.036 | 7.003 | 89.5 | None | NA |
| 386 | 0.039 | 7.354 | 78.9 | C20DA-yGlu | 1 |
| 387 | 0.040 | 0.992 | 94.7 | None | NA |
| 388 | 0.043 | 4.006 | 84.2 | C20DA-yGlu | 1 |
| 389 | 0.045 | 1.039 | 71.1 | C20DA-yGlu | 1 |
| 390 | 0.048 | 0.889 | 86.8 | C20DA-yGlu | 1 |
| 391 | 0.068 | 0.665 | 92.1 | None | NA |
| 392 | 0.113 | 5.034 | 84.2 | C20DA-yGlu | 1 |

AMCHC refers to trans-4-(aminomethyl)cyclohexanecarboxylic acid.
OEG refers to 8-amino-3,6-dioxaoctanoic acid or 8Ado.

Example 2

Fibrillation was determined according to the general protocol for determination of physical stability of peptide analogues. The data for selected hAM$_{15-52}$ analogues are summarized in Table 3 below.

TABLE 3

Table 3 shows that the hAM$_{15-52}$ analogues according to the invention maintain the good fibrillation properties from hAM$_{15-52}$. Most of the fibrillation data are comparable to and some even better than hAM$_{15-52}$ (SEQ ID NO: 1) at pH 7 (ThT signal of 2.6%). All of the fibrillation data are far superior compared to the reference hAMY$_{1-37}$ (SEQ ID NO: 2) (ThT signal on 100%).

| ID | Max ThT signal (%) | identity (% ADM)* |
|---|---|---|
| 1 | 2.600 | 100.0 |
| 2 | 100 | 18.4 |
| 7 | 2.800 | 63.2 |
| 13 | 5.000 | 63.2 |
| 14 | 3.100 | 63.2 |
| 20 | 9.100 | 71.1 |

TABLE 3-continued

Table 3 shows that the hAM$_{15-52}$ analogues according to the invention maintain the good fibrillation properties from hAM$_{15-52}$. Most of the fibrillation data are comparable to and some even better than hAM$_{15-52}$ (SEQ ID NO: 1) at pH 7 (ThT signal of 2.6%). All of the fibrillation data are far superior compared to the reference hAMY$_{1-37}$ (SEQ ID NO: 2) (ThT signal on 100%).

| ID | Max ThT signal (%) | identity (% ADM)* |
|---|---|---|
| 23 | 4.200 | 63.2 |
| 24 | 6.800 | 63.2 |
| 25 | 33.400 | 63.2 |
| 26 | 0.000 | 63.2 |
| 27 | 21.80 | 63.2 |
| 28 | 8.200 | 65.8 |
| 29 | 9.300 | 55.3 |
| 32 | 5.300 | 50.0 |
| 42 | 6.300 | 63.2 |
| 43 | 1.200 | 63.2 |
| 45 | 3.000 | 86.8 |
| 46 | 5.800 | 86.8 |
| 49 | 3.200 | 81.6 |
| 52 | 7.600 | 63.2 |
| 64 | 2.700 | 63.2 |
| 65 | 1.000 | 57.9 |
| 70 | 8.800 | 84.2 |
| 81 | 4.000 | 84.2 |
| 84 | 14.200 | 81.6 |
| 90 | 2.000 | 81.6 |
| 98 | 12.600 | 86.8 |
| 109 | 9.300 | 84.2 |
| 113 | 14.700 | 89.5 |
| 114 | 2.200 | 63.2 |
| 115 | 2.500 | 84.2 |
| 116 | 11.700 | 89.5 |
| 118 | 7.400 | 84.2 |
| 121 | 1.800 | 84.2 |
| 124 | 4.800 | 86.8 |
| 125 | 7.200 | 86.8 |
| 129 | 1.400 | 89.5 |
| 131 | 6.800 | 92.1 |
| 132 | 5.200 | 89.5 |
| 134 | 17.400 | 86.8 |
| 135 | 3.300 | 86.8 |
| 138 | 6.800 | 86.8 |
| 139 | 4.800 | 84.2 |
| 140 | 3.100 | 92.1 |
| 141 | 3.200 | 89.5 |
| 143 | 2.200 | 84.2 |
| 145 | 2.000 | 89.5 |
| 146 | 3.600 | 92.1 |
| 147 | 5.100 | 89.2 |
| 150 | 18.200 | 91.9 |
| 152 | 1.900 | 89.5 |
| 156 | 15.300 | 86.8 |
| 158 | 6.300 | 92.1 |
| 160 | 21.500 | 86.8 |
| 161 | 14.300 | 86.8 |
| 163 | 2.000 | 81.6 |
| 164 | 24.300 | 94.7 |
| 165 | 4.800 | 86.8 |
| 166 | 2.000 | 84.2 |
| 167 | 6.600 | 92.1 |
| 168 | 12.500 | 94.6 |
| 169 | 2.700 | 94.7 |
| 170 | 1.800 | 84.2 |
| 171 | 5.000 | 89.2 |
| 172 | 13.900 | 86.8 |
| 173 | 4.400 | 89.2 |
| 175 | 3.200 | 89.5 |
| 176 | 6.800 | 86.8 |
| 181 | 8.800 | 63.2 |
| 182 | 15.600 | 94.7 |
| 184 | 0.800 | 89.2 |
| 185 | 2.800 | 89.2 |
| 186 | 0.600 | 89.2 |
| 187 | 1.600 | 86.8 |
| 189 | 6.000 | 89.5 |
| 190 | 12.900 | 89.5 |
| 191 | 6.300 | 89.5 |
| 192 | 4.100 | 89.2 |
| 193 | 2.700 | 86.5 |
| 194 | 6.000 | 89.2 |
| 195 | 6.100 | 60.5 |
| 196 | 0.500 | 86.5 |
| 197 | 5.600 | 86.8 |
| 198 | 4.200 | 89.2 |
| 199 | 8.900 | 89.5 |
| 201 | 1.000 | 89.2 |
| 202 | 12.600 | 89.2 |
| 203 | 1.200 | 89.2 |
| 204 | 2.200 | 86.8 |
| 205 | 7.800 | 91.9 |
| 206 | 1.500 | 89.2 |
| 210 | 1.400 | 63.2 |
| 211 | 5.200 | 89.2 |
| 212 | 1.900 | 91.9 |
| 213 | 6.500 | 86.5 |
| 214 | 2.700 | 86.8 |
| 215 | 0.600 | 89.2 |
| 217 | 13.800 | 91.9 |
| 218 | 4.500 | 89.2 |
| 219 | 0.700 | 89.2 |
| 220 | 1.100 | 89.2 |
| 222 | 11.700 | 89.2 |
| 224 | 2.000 | 86.8 |
| 226 | 27.000 | 89.2 |
| 227 | 8.500 | 86.5 |
| 228 | 19.600 | 89.2 |
| 230 | 0.600 | 91.9 |
| 232 | 1.200 | 89.2 |
| 235 | 0.800 | 89.2 |
| 236 | 0.600 | 89.2 |
| 237 | 0.300 | 89.2 |
| 238 | 0.600 | 89.2 |
| 239 | 0.200 | 89.2 |
| 240 | 3.700 | 91.9 |
| 241 | 0.900 | 89.2 |
| 242 | 0.800 | 89.2 |
| 243 | 8.550 | 63.2 |
| 244 | 4.100 | 44.7 |
| 245 | 3.350 | 44.7 |
| 246 | 4.200 | 63.2 |
| 247 | 1.350 | 50.0 |
| 248 | 13.600 | 71.1 |
| 249 | 15.600 | 63.2 |
| 250 | 6.400 | 63.2 |
| 251 | 10.600 | 63.2 |
| 252 | 27.550 | 63.2 |
| 253 | 9.600 | 60.5 |
| 254 | 12.050 | 63.2 |
| 255 | 25.000 | 65.8 |
| 256 | 18.650 | 50.0 |
| 257 | 20.950 | 73.7 |
| 258 | 32.700 | 63.2 |
| 259 | 13.450 | 86.8 |
| 260 | 34.100 | 86.8 |
| 261 | 22.650 | 81.6 |
| 262 | 9.550 | 63.2 |
| 263 | 1.050 | 81.6 |
| 264 | 1.350 | 73.7 |
| 265 | 26.550 | 63.2 |
| 266 | 20.900 | 60.5 |
| 267 | 30.900 | 84.2 |
| 268 | 8.850 | 65.8 |
| 269 | 34.500 | 81.6 |
| 270 | 25.450 | 81.6 |
| 271 | 10.850 | 86.8 |
| 272 | 16.750 | 71.1 |
| 273 | 29.000 | 84.2 |
| 274 | 26.800 | 89.5 |

TABLE 3-continued

Table 3 shows that the hAM$_{15-52}$ analogues according to the invention maintain the good fibrillation properties from hAM$_{15-52}$. Most of the fibrillation data are comparable to and some even better than hAM$_{15-52}$ (SEQ ID NO: 1) at pH 7 (ThT signal of 2.6%). All of the fibrillation data are far superior compared to the reference hAMY$_{1-37}$ (SEQ ID NO: 2) (ThT signal on 100%).

| ID | Max ThT signal (%) | identity (% ADM)* |
|---|---|---|
| 275 | 19.850 | 89.5 |
| 276 | 8.950 | 63.2 |
| 277 | 21.600 | 84.2 |
| 278 | 13.350 | 89.5 |
| 279 | 13.450 | 78.9 |
| 280 | 26.450 | 84.2 |
| 281 | 22.650 | 84.2 |
| 282 | 4.700 | 73.7 |
| 283 | 17.100 | 86.8 |
| 284 | 21.300 | 92.1 |
| 285 | 31.200 | 89.5 |
| 286 | 2.900 | 92.1 |
| 287 | 10.650 | 89.5 |
| 288 | 17.450 | 86.8 |
| 289 | 21.150 | 86.8 |
| 290 | 17.300 | 84.2 |
| 291 | 19.200 | 89.5 |
| 292 | 19.700 | 84.2 |
| 293 | 24.200 | 89.5 |
| 294 | 16.850 | 92.1 |
| 295 | 19.450 | 86.8 |
| 296 | 26.050 | 89.5 |
| 297 | 27.500 | 84.2 |
| 298 | 31.250 | 86.8 |
| 299 | 26.550 | 86.8 |
| 300 | 17.850 | 92.1 |
| 301 | 16.950 | 86.8 |
| 302 | 24.250 | 81.6 |
| 303 | 18.150 | 86.8 |
| 304 | 22.350 | 84.2 |
| 305 | 24.600 | 92.1 |
| 306 | 3.000 | 44.7 |
| 307 | 11.200 | 44.7 |
| 308 | 14.500 | 63.2 |
| 309 | 4.250 | 63.2 |
| 310 | 3.500 | 50.0 |
| 311 | 6.450 | 78.9 |
| 312 | 17.000 | 71.1 |
| 313 | 15.050 | 63.2 |
| 314 | 11.900 | 63.2 |
| 315 | 17.150 | 86.8 |
| 316 | 20.450 | 89.5 |
| 317 | 5.550 | 86.8 |
| 318 | 14.900 | 89.5 |
| 319 | 3.900 | 92.1 |
| 320 | 11.100 | 89.5 |
| 321 | 21.700 | 94.7 |
| 322 | 18.400 | 92.1 |
| 323 | 27.500 | 81.6 |
| 324 | 11.850 | 63.2 |
| 325 | 10.100 | 63.2 |
| 326 | 2.350 | 81.6 |
| 327 | 3.600 | 73.7 |
| 328 | 33.250 | 63.2 |
| 329 | 6.350 | 63.2 |
| 330 | 14.600 | 65.8 |
| 331 | 21.150 | 84.2 |
| 332 | 2.100 | 81.6 |
| 333 | 25.700 | 63.2 |
| 334 | 10.150 | 71.1 |
| 335 | 1.600 | 84.2 |
| 336 | 18.700 | 89.5 |
| 337 | 16.800 | 89.5 |
| 338 | 2.950 | 63.2 |
| 339 | 20.050 | 84.2 |
| 340 | 1.700 | 89.5 |
| 341 | 20.500 | 84.2 |
| 342 | 19.800 | 84.2 |
| 343 | 24.850 | 86.8 |
| 344 | 13.350 | 89.5 |
| 345 | 3.250 | 92.1 |
| 346 | 1.200 | 86.8 |
| 347 | 15.500 | 84.2 |
| 348 | 2.750 | 84.2 |
| 349 | 15.250 | 84.2 |
| 350 | 15.700 | 92.1 |
| 351 | 7.200 | 86.8 |
| 352 | 25.800 | 84.2 |
| 353 | 30.300 | 89.5 |
| 354 | 17.400 | 86.8 |
| 355 | 25.350 | 86.8 |
| 356 | 1.250 | 86.8 |
| 357 | 19.750 | 86.8 |
| 358 | 24.350 | 81.6 |
| 359 | 20.350 | 86.8 |
| 360 | 26.350 | 84.2 |
| 362 | 8.900 | 86.8 |
| 366 | 3.300 | 89.5 |
| 373 | 18.000 | 86.8 |
| 374 | 4.800 | 89.5 |
| 383 | 9.600 | 92.1 |
| 385 | 8.800 | 89.5 |
| 387 | 14.300 | 94.7 |
| 391 | 3.700 | 92.1 |

Example 3

The effect of selected hAM$_{15-52}$ analogues on acute food intake in lean rats were determined. The results are summarized in Table 4 below.

TABLE 4

Table 4 shows that hAM$_{15-52}$ analogues have potent anorectic effects for up to 48 hours following a single SC injection in lean healthy rats (n = 7-8), thereby providing proof-of-principle.

| ID | Dose | Average cumulative food intake (g) | % to vehicle | Significance level to Veh |
|---|---|---|---|---|
| NA | Vehicle | 44.4 | 100 | NA |
| 4 | 10 nmol/kg | 26.3 | 59.23 | *** |
| 4 | 30 nmol/kg | 13.7 | 30.86 | *** |
| 46 | 10 nmol/kg | 23.3 | 52.48 | *** |
| 46 | 30 nmol/kg | 10.7 | 24.10 | *** |
| 60 | 10 nmol/kg | 30.9 | 69.59 | *** |
| 60 | 30 nmol/kg | 20.3 | 45.72 | *** |
| NA | Vehicle | 40.7 | 100 | NA |
| 78 | 10 nmol/kg | 13.7 | 33.66 | *** |
| 69 | 10 nmol/kg | 7.13 | 17.52 | *** |
| 70 | 10 nmol/kg | 24.9 | 61.18 | *** |
| 85 | 10 nmol/kg | 18.6 | 45.70 | *** |
| 124 | 10 nmol/kg | 24.2 | 59.46 | *** |
| 93 | 10 nmol/kg | 19.1 | 46.93 | *** |

TABLE 4-continued

Table 4 shows that hAM$_{15\text{-}52}$ analogues have potent anorectic effects for up to 48 hours following a single SC injection in lean healthy rats (n = 7-8), thereby providing proof-of-principle.

| ID | Dose | Average cumulative food intake (g) | % to vehicle | Significance level to Veh |
|---|---|---|---|---|
| NA | Vehicle | 41.9 | 100 | NA |
| 36 | 10 nmol/kg | 23.3 | 55.61 | *** |
| 6 | 10 nmol/kg | 27.5 | 65.63 | *** |

Dunnett's test one-factor linear model***: P < 0.001 compared to Vehicle (three independent runs were conducted).

Example 4

The Effect of chronic treatment of selected hAM$_{15\text{-}52}$ analogues according to the invention in diet-induced obese (DIO) rats were determined. The results are summarized in Table 5 below.

TABLE 5

Table 5 shows that daily SC injections of SEQ ID NO: 46 or 78 cause a significant reduction in body weight in diet-induced obese rats (n = 10) following a 28-day treatment period, thereby providing proof-of-concept.

| ID | Dose | Average body weight day 28 (gram) | % to vehicle | Significance level to Veh |
|---|---|---|---|---|
| NA | Vehicle | 716 | 100 | NA |
| 46 | 1 nmol/kg | 674 | 94.13 | *** |
| 46 | 3 nmol/kg | 620 | 86.59 | *** |
| 46 | 10 nmol/kg | 618 | 86.31 | *** |

TABLE 5-continued

Table 5 shows that daily SC injections of SEQ ID NO: 46 or 78 cause a significant reduction in body weight in diet-induced obese rats (n = 10) following a 28-day treatment period, thereby providing proof-of-concept.

| ID | Dose | Average body weight day 28 (gram) | % to vehicle | Significance level to Veh |
|---|---|---|---|---|
| NA | Vehicle | 776 | 100 | NA |
| 78 | 10 nmol/kg | 687 | 88.53 | *** |

Dunnett's test one-factor linear model***: P < 0.001 compared to Vehicle (two independent runs were conducted).

Example 5

Deeper investigation of representative amino acids in the position $X_4$, $X_{11}$, $X_{17}$, $X_{37}$ and $X_{38}$ and the corresponding change in potency. The results are summarized in Table 6 below.

TABLE 6

Table 6 shows whether the amino acid change causes increase (I) in hAMY3R potency, unchanged potency (U), or decreased potency (D) compared to the reference (R) amino acid.

| Amino acid | Position 4 | Position 11 | Position 17 | Position 37 | Position 38 |
|---|---|---|---|---|---|
| Y | U | D | R | I | I |
| W | I | U | I | I | I |
| T | R | D | U | R | U |
| Q | D | D | U | U | U |
| P | D | D | D | I | U |
| M | I | D | U | U | I |
| I | I | D | U | U | U |
| H | D | D | I | I | U |
| F | I | D | U | I | I |
| E | D | D | D | U | U |
| A | U | D | U | U | U |
| R | D | R | U | U | U |
| C | I | D | D | U | N/A |
| K | D | D | U | U | U |
| Hyp | N/A | N/A | N/A | N/A | R |
| Cit | N/A | U | N/A | N/A | N/A |

N/A Not available.

TABLE 7

SEQUENCE LISTING

| ID | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 | G | C | R | F | G | T | C | T | V | Q | K | L | A | H | Q | I | Y | Q | F | T |
| 2 | K | C | N | T | A | T | C | A | T | Q | R | L | A | N | F | L | V | H | S | S |
| 3 | K | C | N | F | A | T | C | T | V | Q | R | L | A | H | Q | I | Y | Q | F | T |
| 4 | K | C | N | T | A | T | C | T | V | D | R | L | A | H | Q | I | Y | Q | F | T |
| 5 | K | C | N | T | A | T | C | T | V | Q | R | L | A | D | Q | I | Y | Q | F | T |
| 6 | K | C | N | T | A | T | C | T | V | Q | R | L | A | E | Q | I | Y | Q | F | T |
| 7 | K | C | N | T | A | T | C | T | V | Q | R | L | A | A | Q | I | Y | Q | F | T |
| 8 | K | C | N | T | S | T | C | T | V | A | R | L | A | D | Q | I | T | Q | F | S |
| 9 | R | C | N | A | S | T | C | T | V | N | R | L | A | D | Q | I | T | Q | F | S |
| 10 | K | C | N | F | A | T | C | T | V | Q | R | L | A | H | Q | I | Y | Q | F | T |
| 11 | K | C | N | T | A | T | C | T | V | Q | R | L | A | H | Q | I | N | Q | F | T |
| 12 | K | C | N | T | A | T | C | T | V | Q | R | L | A | E | Q | I | Y | Q | F | T |
| 13 | K | C | N | T | A | T | C | T | V | Q | R | L | A | H | A | I | Y | Q | F | T |
| 14 | K | C | N | T | A | T | C | T | V | Q | R | L | A | H | Q | I | A | Q | F | T |
| 15 | K | C | N | T | S | T | C | T | V | A | R | L | A | D | Q | I | T | Q | F | S |
| 16 | G | C | R | F | G | T | C | T | V | Q | R | L | A | N | F | L | Y | Q | F | T |
| 17 | K | C | N | F | A | T | C | T | V | Q | R | L | A | H | Q | I | Y | Q | F | T |
| 18 | K | C | N | F | A | T | C | T | V | Q | R | L | A | H | Q | I | Y | Q | F | T |
| 19 | K | C | N | T | A | T | C | A | T | Q | R | L | A | N | F | L | V | H | S | S |
| 20 | K | C | N | T | A | T | C | T | V | Q | R | L | A | H | Q | I | Y | Q | F | T |
| 21 | K | C | N | T | A | T | C | T | V | Q | R | L | A | N | Q | I | Y | Q | F | T |
| 22 | K | C | N | T | A | T | C | T | V | Q | R | L | A | H | Q | I | T | Q | F | T |

TABLE 7-continued

SEQUENCE LISTING

| | | | | | | | | | | | | | | | | | | | |
|---|---|---|---|---|---|---|---|---|---|---|---|---|---|---|---|---|---|---|---|
| 23 | K | C | N | T | A | T | C | T | V | Q | R | L | A | H | Q | I | Y | Q | F | A |
| 24 | K | C | N | T | A | T | C | T | V | Q | R | L | A | H | Q | I | Y | Q | F | T |
| 25 | K | C | N | T | A | T | C | T | V | Q | R | L | A | H | Q | I | Y | Q | F | T |
| 26 | K | C | N | T | A | T | C | T | V | Q | R | L | A | H | Q | I | Y | Q | F | T |
| 27 | K | C | N | T | A | T | C | T | V | Q | R | L | A | H | Q | I | Y | Q | F | T |
| 28 | K | C | N | T | A | T | C | T | V | Q | R | L | A | H | Q | I | Y | Q | F | T |
| 29 | K | C | N | T | A | T | C | T | V | Q | R | L | A | H | Q | I | Y | Q | Q | F |
| 30 | K | C | N | T | A | T | C | T | V | Q | R | L | A | H | Q | I | Y | Q | F | T |
| 31 | K | C | N | T | A | T | C | T | V | Q | R | L | A | H | Q | I | Y | Q | F | T |
| 32 | R | C | Q | T | S | T | C | T | V | A | R | L | A | E | Q | I | A | Q | Y | T |
| 33 | R | C | Q | A | S | T | C | T | V | A | Cit | L | A | E | Q | I | A | Q | Y | T |
| 34 | K | C | N | T | A | T | C | T | V | Q | R | L | A | H | Q | I | Y | Q | F | T |
| 35 | K | C | N | T | A | T | C | T | V | Q | R | L | A | H | Q | I | Q | Q | F | T |
| 36 | K | C | K | T | A | T | C | T | V | Q | R | L | A | E | Q | I | Y | Q | F | T |
| 37 | K | C | N | T | A | T | C | T | V | A | R | L | A | H | Q | I | Y | Q | F | T |
| 38 | K | C | N | T | A | T | C | T | V | N | R | L | A | H | Q | I | Y | Q | F | T |
| 39 | R | C | N | T | A | T | C | T | V | Q | R | L | A | H | Q | I | Y | Q | F | T |
| 40 | K | C | N | T | A | T | C | T | V | Q | R | L | A | E | Q | I | Y | Q | F | T |
| 41 | K | C | N | T | A | T | C | T | V | Q | R | L | A | E | Q | I | Y | Q | F | T |
| 42 | K | C | N | T | A | T | C | T | V | Q | R | L | A | H | Q | I | Y | A | F | T |
| 43 | K | C | N | T | A | T | C | T | V | Q | R | L | A | H | Q | I | Y | Q | F | T |
| 44 | K | C | N | T | A | T | C | T | V | Q | R | L | A | E | Q | I | Y | Q | F | T |
| 45 | G | C | R | F | G | T | C | T | V | Q | R | L | A | H | Q | I | Y | Q | F | T |
| 46 | G | C | R | F | G | T | C | T | V | Q | R | L | A | H | Q | I | Y | Q | F | T |
| 47 | K | C | N | T | A | T | C | T | V | Q | R | L | A | Y | Q | I | Y | Q | F | T |
| 48 | K | C | N | T | A | T | C | T | V | Q | R | L | A | H | Q | I | Y | Q | Y | T |
| 49 | G | C | R | T | G | T | C | T | V | Q | R | L | A | H | Q | I | Y | Q | F | T |
| 50 | K | C | N | T | S | T | C | T | V | Q | R | L | A | H | Q | I | Y | Q | F | T |
| 51 | K | C | N | T | A | T | C | T | V | Q | R | L | A | E | Q | I | Y | Q | F | T |
| 52 | K | C | N | T | A | T | C | T | V | Q | R | L | A | H | Q | I | Y | Q | F | T |
| 53 | K | C | N | T | A | T | C | T | V | Q | R | L | A | H | Q | I | Y | Q | F | T |
| 54 | G | C | R | F | G | T | C | T | V | Q | R | L | A | H | F | L | Y | Q | F | T |
| 55 | K | C | N | T | A | T | C | T | V | E | R | L | A | H | Q | I | Y | Q | F | T |
| 56 | G | C | R | F | G | T | C | T | V | Q | R | L | A | H | F | L | Y | Q | F | T |
| 57 | K | C | N | T | A | T | C | T | V | Q | R | L | A | H | Q | I | Y | Q | F | S |
| 58 | K | C | N | T | A | T | C | A | T | Q | R | L | A | N | F | L | V | H | S | S |
| 59 | K | C | N | T | A | T | C | A | T | Q | R | L | A | N | F | L | V | H | S | S |
| 60 | K | C | N | T | A | T | C | T | V | Q | R | L | A | H | Q | I | Y | Q | F | T |
| 61 | K | C | N | T | A | T | C | T | V | Q | R | L | A | H | Q | I | A | Q | F | T |
| 62 | K | C | N | T | S | T | C | T | V | Q | R | L | A | H | Q | I | A | Q | F | T |
| 63 | K | C | N | T | A | T | C | T | V | Q | R | L | A | E | Q | I | Y | Q | F | T |
| 64 | K | C | N | T | A | T | C | T | V | Q | R | L | A | H | Q | I | Y | Q | F | T |
| 65 | K | C | N | T | A | T | C | T | V | Q | R | L | A | H | Q | I | Y | — | Q | F |
| 66 | K | C | N | T | A | T | C | T | V | Q | R | L | A | E | Q | I | Y | Q | F | T |
| 67 | K | C | N | F | A | T | C | T | V | Q | R | L | A | H | Q | I | Y | Q | F | T |
| 68 | K | C | N | F | A | T | C | T | V | Q | R | L | A | H | Q | I | Y | Q | F | T |
| 69 | K | C | N | T | A | T | C | T | V | Q | R | L | A | H | Q | I | A | Q | F | T |
| 70 | G | C | N | F | G | T | C | T | V | Q | R | L | A | H | Q | I | Y | Q | F | T |
| 71 | K | C | N | T | A | T | C | T | V | Q | R | L | A | H | Q | I | A | Q | Y | T |
| 72 | K | C | Q | T | A | T | C | T | V | Q | R | L | A | E | Q | I | Y | Q | F | T |
| 73 | K | C | N | T | A | T | C | T | V | Q | R | L | A | E | Q | I | Y | Q | F | T |
| 74 | K | C | N | T | A | T | C | T | V | Q | R | L | A | K | Q | I | Y | Q | F | T |
| 75 | K | C | N | T | A | T | C | T | V | Q | R | L | A | H | Q | I | Y | Q | F | T |
| 76 | R | C | G | T | A | T | C | A | T | E | R | L | A | AAD | F | L | Q | R | S | — |
| 77 | K | C | N | T | A | T | C | T | V | Q | R | L | A | H | Q | I | Y | O | F | T |
| 78 | K | C | N | T | A | T | C | T | V | Q | R | L | A | E | Q | I | A | Q | F | T |
| 79 | K | C | N | T | A | T | C | T | V | Q | R | L | A | H | Q | I | A | Q | F | S |
| 80 | R | C | Q | T | A | T | C | A | T | E | R | L | A | H | F | L | Q | R | S | — |
| 81 | G | C | R | F | G | T | C | T | V | Q | R | L | A | H | Q | I | Y | Q | F | T |
| 82 | K | C | N | T | A | T | C | T | V | Q | R | L | A | H | Q | I | Y | Q | F | T |
| 83 | K | C | N | T | A | T | C | T | V | Q | R | L | A | H | Q | I | Y | Q | F | A |
| 84 | G | C | R | T | G | T | C | T | V | Q | R | L | A | H | Q | I | Y | Q | F | T |
| 85 | K | C | N | T | A | T | C | T | V | Q | R | L | A | H | Q | I | V | Q | F | T |
| 86 | K | C | N | T | A | T | C | T | V | A | R | L | A | H | Q | I | N | Q | F | T |
| 87 | K | C | N | T | A | T | C | T | V | Q | R | L | A | H | Q | I | A | Q | F | T |
| 88 | K | C | N | T | S | T | C | T | V | Q | R | L | A | H | Q | I | A | Q | F | T |
| 89 | K | C | N | T | A | T | C | T | V | Q | R | L | A | E | Q | I | Y | Q | F | K |
| 90 | G | C | R | F | G | T | C | T | V | Q | R | L | A | H | Q | I | Y | Q | F | T |
| 91 | K | C | N | T | A | T | C | T | V | Q | R | L | A | H | Q | I | Y | Q | F | T |
| 92 | K | C | N | T | A | T | C | T | V | Q | R | L | A | H | Q | I | A | Q | F | T |
| 93 | K | C | N | T | A | T | C | A | T | Q | R | L | A | N | F | L | V | H | S | S |
| 94 | K | C | N | T | A | T | C | T | V | Q | R | L | A | H | Q | I | A | Q | F | Y |
| 95 | K | C | N | T | A | T | C | T | V | Q | R | L | A | H | Q | I | A | Q | F | T |
| 96 | K | C | N | T | A | T | C | T | V | Q | R | L | A | E | Q | I | Y | Q | F | T |
| 97 | K | C | A | T | A | T | C | T | V | Q | R | L | A | E | Q | I | Y | Q | F | T |
| 98 | G | C | R | F | G | T | C | T | V | Q | R | L | A | H | Q | I | Y | Q | F | T |
| 99 | K | C | N | T | A | T | C | T | V | Q | R | L | A | H | Q | I | Y | Q | F | T |
| 100 | K | C | N | T | A | T | C | T | V | Q | R | L | A | E | Q | I | Y | Q | F | T |

TABLE 7-continued

SEQUENCE LISTING

| | | | | | | | | | | | | | | | | | | |
|---|---|---|---|---|---|---|---|---|---|---|---|---|---|---|---|---|---|---|
| 101 | K | C | N | A | A | T | C | T | V | Q | R | L | A | E | Q | I | Y | Q | F | T |
| 102 | K | C | N | T | A | T | C | T | V | Q | R | L | A | H | Q | I | Y | Q | F | T |
| 103 | K | C | N | T | A | T | C | T | V | V | R | L | A | H | Q | I | Y | Q | F | T |
| 104 | K | C | N | T | A | T | C | T | V | Q | R | L | A | H | Q | I | Y | Q | F | Y |
| 105 | K | C | N | T | A | T | C | T | V | Q | R | L | A | H | Q | I | A | Q | F | A |
| 106 | K | C | N | T | A | T | C | T | V | Q | R | L | A | E | Q | I | Y | Q | F | T |
| 107 | K | C | N | T | A | T | C | T | V | A | R | L | A | H | Q | I | A | Q | F | T |
| 108 | K | C | N | T | A | T | C | T | V | Q | R | L | A | E | Q | I | Y | Q | F | T |
| 109 | G | C | R | T | G | T | C | T | V | Q | R | L | A | H | Q | I | Y | Q | F | T |
| 110 | K | C | N | T | A | T | C | T | V | Q | R | L | A | H | Q | I | E | Q | F | T |
| 111 | G | C | R | F | G | T | C | T | V | Q | R | L | A | H | Q | I | Y | Q | F | T |
| 112 | K | C | N | T | A | T | C | T | V | D | R | L | A | H | Q | I | A | Q | F | T |
| 113 | G | C | R | F | G | T | C | T | V | Q | R | L | A | H | Q | I | Y | Q | F | T |
| 114 | K | C | N | T | A | T | C | T | V | Q | R | L | A | H | Q | I | Y | Q | A | T |
| 115 | G | C | R | T | G | T | C | T | V | Q | R | L | A | H | Q | I | Y | Q | F | T |
| 116 | G | C | R | F | G | T | C | T | V | Q | R | L | A | H | Q | I | Y | Q | F | T |
| 117 | G | C | R | F | G | T | C | T | V | Q | R | L | A | H | F | L | Y | Q | F | T |
| 118 | G | C | R | T | G | T | C | T | V | Q | R | L | A | H | Q | I | Y | Q | F | T |
| 119 | K | C | N | T | Aib | T | C | T | V | Q | R | L | A | H | Q | I | Y | Q | F | T |
| 120 | K | C | N | T | A | T | C | T | V | Q | R | L | A | H | Q | I | A | Q | F | T |
| 121 | G | C | R | T | G | T | C | T | V | Q | R | L | A | H | Q | I | Y | Q | F | T |
| 122 | K | C | N | T | A | T | C | T | V | Q | R | L | A | E | Q | I | Y | Q | F | T |
| 123 | G | C | R | F | G | T | C | T | V | Q | R | L | A | H | F | L | Y | Q | F | T |
| 124 | G | C | R | F | G | T | C | T | V | Q | R | L | A | H | Q | I | Y | Q | F | T |
| 125 | G | C | R | F | G | T | C | T | V | Q | R | L | A | H | Q | I | Y | Q | F | T |
| 126 | K | C | N | T | A | T | C | T | V | Q | R | L | A | E | Q | I | Y | Q | F | T |
| 127 | G | C | R | F | G | T | C | T | V | Q | R | L | A | H | Q | I | Y | Q | F | T |
| 128 | K | C | N | T | A | T | C | A | T | Q | R | L | A | N | F | L | V | H | S | S |
| 129 | G | C | R | T | G | T | C | T | V | Q | R | L | A | H | Q | I | Y | Q | F | T |
| 130 | K | C | N | T | A | T | C | T | V | D | R | L | A | H | Q | I | A | Q | F | T |
| 131 | G | C | R | F | G | T | C | T | V | Q | R | L | A | H | Q | I | Y | O | F | T |
| 132 | G | C | R | F | G | T | C | T | V | Q | R | L | A | H | Q | I | Y | Q | F | T |
| 133 | K | C | N | T | A | T | C | T | V | A | R | L | A | E | Q | I | Y | Q | F | T |
| 134 | G | C | R | F | G | T | C | T | V | Q | R | L | A | H | Q | I | Y | Q | F | T |
| 135 | G | C | R | F | G | T | C | T | V | Q | R | L | A | H | Q | I | Y | Q | F | T |
| 136 | K | C | N | T | A | T | C | T | V | Q | R | L | A | E | Q | I | K | Q | F | T |
| 137 | K | C | N | T | A | T | C | T | V | A | R | L | A | H | Q | I | N | Q | F | T |
| 138 | G | C | R | T | G | T | C | T | V | Q | R | L | A | H | Q | I | Y | Q | F | T |
| 139 | G | C | R | T | G | T | C | T | V | Q | R | L | A | H | Q | I | Y | Q | F | T |
| 140 | G | C | R | F | G | T | C | T | V | Q | R | L | A | H | Q | I | Y | Q | F | T |
| 141 | G | C | R | F | G | T | C | T | V | Q | R | L | A | H | Q | I | Y | Q | F | T |
| 142 | G | C | R | T | G | T | C | T | V | Q | R | L | A | H | Q | I | Y | Q | F | T |
| 143 | G | C | R | T | G | T | C | T | V | Q | R | L | A | H | Q | I | Y | Q | F | T |
| 144 | K | C | N | T | A | T | C | T | V | Q | R | L | A | E | Q | I | A | Q | F | T |
| 145 | G | C | R | F | G | T | C | T | V | Q | R | L | A | H | Q | I | Y | Q | F | T |
| 146 | G | C | R | F | G | T | C | T | V | Q | R | L | A | H | Q | I | Y | Q | F | T |
| 147 | G | C | R | I | G | T | C | T | V | Q | R | L | A | H | Q | I | Y | Q | F | T |
| 148 | K | C | N | T | A | T | C | A | T | Q | R | L | A | N | F | L | V | H | S | S |
| 149 | K | C | N | T | A | T | C | A | T | Q | R | L | A | N | F | L | V | H | S | S |
| 150 | G | C | R | W | G | T | C | T | V | Q | R | L | A | H | Q | I | Y | Q | F | T |
| 151 | G | C | R | T | G | T | C | T | V | Q | R | L | A | H | Q | I | Y | Q | F | T |
| 152 | G | C | R | F | G | T | C | T | V | Q | R | L | A | H | Q | I | Y | Q | F | T |
| 153 | K | C | N | T | A | T | C | T | V | Q | Cit | L | A | E | Q | I | A | Q | F | T |
| 154 | G | C | R | F | G | T | C | T | V | Q | R | L | A | H | Q | I | Y | Q | F | T |
| 155 | G | C | R | F | G | T | C | T | V | Q | R | L | A | H | Q | I | Y | Q | F | T |
| 156 | G | C | R | T | G | T | C | T | V | Q | R | L | A | H | Q | I | Y | Q | F | T |
| 157 | G | C | R | T | G | T | C | T | V | Q | R | L | A | H | Q | I | Y | Q | F | T |
| 158 | G | C | R | F | G | T | C | T | V | Q | R | L | A | H | Q | I | Y | Q | F | T |
| 159 | K | C | N | T | A | T | C | T | V | I | R | L | A | H | Q | I | Y | Q | F | T |
| 160 | G | C | R | T | G | T | C | T | V | Q | R | L | A | H | Q | I | Y | Q | I | T |
| 161 | G | C | R | T | G | T | C | T | V | Q | R | L | A | H | Q | I | Y | Q | F | T |
| 162 | K | C | N | T | A | T | C | A | T | Q | R | L | A | N | F | L | V | H | S | S |
| 163 | G | C | R | T | G | T | C | T | V | Q | R | L | A | H | Q | I | Y | Q | F | T |
| 164 | G | C | R | F | G | T | C | T | V | Q | R | L | A | H | Q | I | Y | Q | F | T |
| 165 | G | C | R | T | G | T | C | T | V | Q | R | L | A | H | Q | I | Y | Q | F | T |
| 166 | G | C | R | T | G | T | C | T | V | Q | R | L | A | H | Q | I | Y | Q | F | T |
| 167 | G | C | R | F | G | T | C | T | V | Q | R | L | A | H | Q | I | Y | Q | F | T |
| 168 | G | C | R | F | G | T | C | T | V | Q | R | L | A | H | Q | I | Y | Q | F | T |
| 169 | G | C | R | F | G | T | C | T | V | Q | R | L | A | H | Q | I | Y | Q | F | T |
| 170 | G | C | R | T | G | T | C | T | V | Q | R | L | A | H | Q | I | Y | Q | F | T |
| 171 | G | C | R | W | G | T | C | T | V | Q | R | L | A | H | Q | I | Y | Q | F | T |
| 172 | G | C | R | T | G | T | C | T | V | Q | R | L | A | H | Q | I | Y | Q | F | T |
| 173 | G | C | R | M | G | T | C | T | V | Q | R | L | A | H | Q | I | Y | Q | F | T |
| 174 | G | C | R | F | G | T | C | T | V | Q | R | L | A | H | Q | I | Y | Q | F | T |
| 175 | G | C | R | F | G | T | C | T | V | Q | R | L | A | H | Q | I | Y | Q | F | T |
| 176 | G | C | R | T | G | T | C | T | V | Q | R | L | A | H | Q | I | Y | Q | F | T |
| 177 | G | C | R | T | G | T | C | T | V | Q | R | L | A | H | Q | I | Y | Q | F | T |
| 178 | G | C | R | T | G | T | C | T | V | Q | R | L | A | H | Q | I | Y | Q | F | T |

TABLE 7-continued

SEQUENCE LISTING

| | | | | | | | | | | | | | | | | | | |
|---|---|---|---|---|---|---|---|---|---|---|---|---|---|---|---|---|---|---|
| 179 | G | C | R | T | G | T | C | T | V | Q | R | L | A | H | Q | I | Y | Q | F | T |
| 180 | K | C | N | T | A | T | C | A | T | Q | R | L | A | N | F | L | V | H | S | S |
| 181 | K | C | N | T | A | T | C | T | V | Q | R | L | A | H | Q | I | Y | — | F | T |
| 182 | G | C | R | F | G | T | C | T | V | Q | R | L | A | H | Q | I | Y | Q | F | T |
| 183 | G | C | R | T | G | T | C | T | V | Q | R | L | A | H | Q | I | Y | Q | F | T |
| 184 | G | C | R | T | G | T | C | T | V | Q | R | L | A | H | Q | I | Y | Q | F | T |
| 185 | G | C | R | T | G | T | C | T | V | Q | R | L | A | H | Q | I | Y | Q | F | T |
| 186 | G | C | R | T | G | T | C | T | V | Q | R | L | A | H | Q | I | Y | Q | F | T |
| 187 | G | C | R | T | G | T | C | T | V | Q | R | L | A | H | Q | I | Y | Q | F | T |
| 188 | G | C | R | T | G | T | C | T | V | Q | R | L | A | H | Q | I | Y | Q | F | T |
| 189 | G | C | R | T | G | T | C | T | V | Q | R | L | A | H | Q | I | Y | Q | F | T |
| 190 | G | C | R | T | G | T | C | T | V | Q | R | L | A | H | Q | I | Y | Q | F | T |
| 191 | G | C | R | T | G | T | C | T | V | Q | R | L | A | H | Q | I | Y | Q | F | T |
| 192 | G | C | R | M | G | T | C | T | V | Q | R | L | A | H | Q | I | Y | Q | F | T |
| 193 | G | C | R | T | G | T | C | T | V | Q | R | L | A | H | Q | I | H | Q | F | T |
| 194 | K | C | R | M | G | T | C | T | V | Q | R | L | A | H | Q | I | Y | Q | F | T |
| 195 | K | C | N | T | A | T | C | T | V | Q | R | L | A | H | Q | I | Y | — | Q | T |
| 196 | G | C | R | T | G | T | C | T | V | Q | R | L | A | H | Q | I | A | Q | F | T |
| 197 | G | C | R | T | G | T | C | T | V | Q | R | L | A | H | Q | I | Y | Q | F | T |
| 198 | G | C | R | I | G | T | C | T | V | Q | R | L | A | H | Q | I | Y | Q | F | T |
| 199 | G | C | R | T | G | T | C | T | V | Q | R | L | A | H | Q | I | Y | Q | F | T |
| 200 | G | C | R | F | G | T | C | T | V | Q | R | L | A | H | F | L | Y | Q | F | T |
| 201 | G | C | R | T | G | T | C | T | V | Q | R | L | A | H | Q | I | Y | Q | F | T |
| 202 | G | C | R | W | G | T | C | T | V | Q | R | L | A | H | Q | I | Y | Q | F | T |
| 203 | G | C | R | T | G | T | C | T | V | Q | R | L | A | H | Q | I | Y | Q | F | T |
| 204 | G | C | R | T | G | T | C | T | V | Q | R | L | A | H | Q | I | Y | Q | F | T |
| 205 | K | C | R | F | G | T | C | T | V | Q | R | L | A | H | Q | I | Y | Q | F | T |
| 206 | G | C | R | T | G | T | C | T | V | Q | R | L | A | H | Q | I | Y | Q | F | T |
| 207 | K | C | N | T | A | T | C | A | T | Q | R | L | A | N | F | L | V | H | S | S |
| 208 | G | C | R | F | G | T | C | T | V | Q | R | L | A | H | F | L | Y | Q | F | T |
| 209 | G | C | R | T | G | T | C | T | V | Q | R | L | A | H | Q | I | Y | Q | F | T |
| 210 | K | C | N | T | A | T | C | T | V | Q | R | L | A | H | Q | A | Y | Q | F | T |
| 211 | G | C | R | T | G | T | C | T | V | Q | R | L | A | H | Q | I | Y | Q | F | T |
| 212 | G | C | R | F | G | T | C | T | V | Q | R | L | A | H | Q | I | Y | Q | F | T |
| 213 | G | C | R | T | G | T | C | T | V | Q | R | L | A | H | Q | I | W | O | F | T |
| 214 | G | C | R | T | G | T | C | T | V | Q | R | L | A | H | Q | I | Y | Q | F | T |
| 215 | G | C | R | T | G | T | C | T | V | Q | R | L | A | H | Q | I | Y | Q | F | T |
| 216 | G | C | R | T | G | T | C | T | V | Q | R | L | A | H | Q | I | Y | Q | F | T |
| 217 | G | C | R | F | G | T | C | T | V | Q | R | L | A | H | Q | L | Y | Q | F | T |
| 218 | G | C | R | T | G | T | C | T | V | Q | R | L | A | H | Q | I | Y | Q | F | T |
| 219 | G | C | R | T | G | T | C | T | V | Q | R | L | A | H | Q | I | Y | Q | F | T |
| 220 | G | C | R | T | G | T | C | T | V | Q | R | L | A | H | Q | I | Y | Q | F | T |
| 221 | K | C | N | T | A | T | C | T | V | Q | R | L | A | E | Q | I | Y | Q | F | T |
| 222 | G | C | R | M | G | T | C | T | V | Q | R | L | A | H | Q | I | Y | Q | F | T |
| 223 | G | C | R | F | G | T | C | T | V | Q | R | L | A | H | F | L | Y | Q | F | T |
| 224 | G | C | R | T | G | T | C | T | V | O | R | L | A | H | Q | I | Y | Q | F | T |
| 225 | K | C | Z | T | L | T | C | T | V | Q | R | L | A | H | Q | I | Y | Q | F | T |
| 226 | G | C | R | T | G | T | C | T | V | Q | R | L | A | H | Q | I | Y | Q | F | T |
| 227 | G | C | R | T | G | T | C | T | V | Q | R | L | A | H | Q | I | H | Q | F | T |
| 228 | G | C | R | T | G | T | C | T | V | Q | R | L | A | H | Q | I | H | Q | F | T |
| 229 | G | C | R | F | G | T | C | T | V | Q | R | L | A | H | Q | I | Y | Q | F | T |
| 230 | G | C | R | T | G | T | C | T | V | Q | R | L | A | H | Q | I | Y | Q | F | T |
| 231 | K | C | N | T | Y | T | C | T | V | Q | R | L | A | H | Q | I | Y | Q | F | T |
| 232 | G | C | R | T | G | T | C | T | V | Q | R | L | A | H | Q | I | Y | Q | F | T |
| 233 | K | C | N | T | A | T | C | T | V | Q | R | L | A | E | Q | I | Y | Q | F | T |
| 234 | K | C | N | T | A | T | C | A | T | Q | R | L | A | N | F | L | V | Q | F | T |
| 235 | G | C | R | T | G | T | C | T | V | Q | R | L | A | H | Q | I | Y | Q | F | T |
| 236 | G | C | R | T | G | T | C | T | V | Q | R | L | A | H | Q | I | Y | Q | F | T |
| 237 | G | C | R | T | G | T | C | T | V | Q | R | L | A | H | Q | I | Y | Q | F | T |
| 238 | G | C | R | T | G | T | C | T | V | Q | R | L | A | H | Q | I | Y | Q | F | T |
| 239 | G | C | R | T | G | T | C | T | V | Q | R | L | A | H | Q | I | Y | Q | F | T |
| 240 | G | C | R | F | G | T | C | T | V | Q | R | L | A | H | Q | I | Y | Q | F | T |
| 241 | G | C | R | T | G | T | C | T | V | O | R | L | A | H | Q | I | Y | Q | F | T |
| 242 | G | C | R | T | G | T | C | T | V | Q | R | L | A | H | Q | I | Y | Q | F | T |
| 243 | K | C | N | T | A | T | C | T | V | Q | Cit | L | A | A | Q | I | Y | Q | F | T |
| 244 | K | C | N | T | S | T | C | T | V | A | Cit | L | A | D | Q | I | T | Q | F | S |
| 245 | R | C | N | A | S | T | C | T | V | N | Cit | L | A | D | Q | I | T | Q | F | S |
| 246 | K | C | N | T | A | T | C | T | V | Q | Cit | L | A | H | Q | I | A | Q | F | T |
| 247 | K | C | N | T | S | T | C | T | V | A | Cit | L | A | D | Q | I | T | Q | F | S |
| 248 | K | C | N | T | A | T | C | T | V | Q | Cit | L | A | H | Q | I | Y | Q | F | T |
| 249 | K | C | N | T | A | T | C | T | V | Q | Cit | L | A | H | Q | I | Y | Q | F | A |
| 250 | K | C | N | T | A | T | C | T | V | Q | Cit | L | A | H | Q | I | Y | Q | F | T |
| 251 | K | C | N | T | A | T | C | T | V | Q | Cit | L | A | H | Q | I | Y | Q | F | T |
| 252 | K | C | N | T | A | T | C | T | V | Q | Cit | L | A | H | Q | I | Y | Q | F | T |
| 253 | K | C | N | T | A | T | C | T | V | Q | Cit | L | A | H | Q | I | Y | Q | F | — |
| 254 | K | C | N | T | A | T | C | T | V | Q | Cit | L | A | H | Q | I | Y | Q | F | T |
| 255 | K | C | N | T | A | T | C | T | V | Q | Cit | L | A | H | Q | I | Y | Q | F | T |
| 256 | R | C | Q | T | S | T | C | T | V | A | Cit | L | A | E | Q | I | A | Q | Y | T |

TABLE 7-continued

SEQUENCE LISTING

| | | | | | | | | | | | | | | | | | | |
|---|---|---|---|---|---|---|---|---|---|---|---|---|---|---|---|---|---|---|
| 257 | K | C | N | T | A | T | C | T | V | Q | Cit | L | A | H | Q | I | Y | Q | F | T |
| 258 | K | C | N | T | A | T | C | T | V | Q | Cit | L | A | H | Q | I | Y | Q | F | T |
| 259 | G | C | R | F | G | T | C | T | V | Q | Cit | L | A | H | Q | I | Y | Q | F | T |
| 260 | G | C | R | F | G | T | C | T | V | Q | Cit | L | A | H | Q | I | Y | Q | F | T |
| 261 | G | C | R | T | G | T | C | T | V | Q | Cit | L | A | H | Q | I | Y | Q | F | T |
| 262 | K | C | N | T | A | T | C | T | V | O | Cit | L | A | H | Q | I | Y | Q | F | T |
| 263 | G | C | R | F | G | T | C | T | V | Q | Cit | L | A | H | F | L | Y | Q | F | T |
| 264 | G | C | R | F | G | T | C | T | V | Q | Cit | L | A | H | F | L | Y | Q | F | T |
| 265 | K | C | N | T | A | T | C | T | V | Q | Cit | L | A | H | Q | I | Y | Q | F | — |
| 266 | K | C | N | T | A | T | C | T | V | Q | Cit | L | A | E | Q | I | Y | Q | F | T |
| 267 | G | C | R | F | G | T | C | T | V | Q | Cit | L | A | H | Q | I | Y | Q | F | T |
| 268 | K | C | N | T | A | T | C | T | V | Q | Cit | L | A | H | Q | I | Y | Q | F | T |
| 269 | G | C | R | T | G | T | C | T | V | Q | Cit | L | A | H | Q | I | Y | Q | F | T |
| 270 | G | C | R | F | G | T | C | T | V | Q | Cit | L | A | H | Q | I | Y | Q | F | T |
| 271 | G | C | R | F | G | T | C | T | V | Q | Cit | L | A | H | Q | I | Y | Q | F | T |
| 272 | K | C | N | T | A | T | C | T | V | Q | Cit | L | A | H | Q | I | Y | Q | F | T |
| 273 | G | C | R | T | G | T | C | T | V | Q | Cit | L | A | H | Q | I | Y | Q | F | T |
| 274 | G | C | R | F | G | T | C | T | V | Q | Cit | L | A | H | Q | I | Y | Q | F | T |
| 275 | G | C | R | F | G | T | C | T | V | Q | Cit | L | A | H | Q | I | Y | Q | F | T |
| 276 | K | C | N | T | A | T | C | T | V | Q | Cit | L | A | H | Q | I | Y | Q | A | T |
| 277 | G | C | R | T | G | T | C | T | V | Q | Cit | L | A | H | Q | I | Y | Q | F | T |
| 278 | G | C | R | F | G | T | C | T | V | Q | Cit | L | A | H | Q | I | Y | Q | F | T |
| 279 | G | C | R | F | G | T | C | T | V | Q | Cit | L | A | H | F | L | Y | Q | F | T |
| 280 | G | C | R | T | G | T | C | T | V | Q | Cit | L | A | H | Q | I | Y | Q | F | T |
| 281 | G | C | R | T | G | T | C | T | V | Q | Cit | L | A | H | Q | I | Y | Q | F | T |
| 282 | G | C | R | F | G | T | C | T | V | Q | Cit | L | A | H | F | L | Y | Q | F | T |
| 283 | G | C | R | F | G | T | C | T | V | Q | Cit | L | A | H | Q | I | Y | Q | F | T |
| 284 | G | C | R | F | G | T | C | T | V | Q | Cit | L | A | H | Q | I | Y | Q | F | T |
| 285 | G | C | R | T | G | T | C | T | V | Q | Cit | L | A | H | Q | I | Y | Q | F | T |
| 286 | G | C | R | F | G | T | C | T | V | Q | Cit | L | A | H | Q | I | Y | Q | F | T |
| 287 | G | C | R | F | G | T | C | T | V | Q | Cit | L | A | H | Q | I | Y | Q | F | T |
| 288 | G | C | R | F | G | T | C | T | V | Q | Cit | L | A | H | Q | I | Y | Q | F | T |
| 289 | G | C | R | F | G | T | C | T | V | Q | Cit | L | A | H | Q | I | Y | Q | F | T |
| 290 | G | C | R | T | G | T | C | T | V | Q | Cit | L | A | H | Q | I | Y | Q | F | T |
| 291 | G | C | R | F | G | T | C | T | V | Q | Cit | L | A | H | Q | I | Y | Q | F | T |
| 292 | G | C | R | T | G | T | C | T | V | Q | Cit | L | A | H | Q | I | Y | Q | F | T |
| 293 | G | C | R | F | G | T | C | T | V | Q | Cit | L | A | H | Q | I | Y | Q | F | T |
| 294 | G | C | R | F | G | T | C | T | V | Q | Cit | L | A | H | Q | I | Y | Q | F | T |
| 295 | G | C | R | I | G | T | C | T | V | Q | Cit | L | A | H | Q | I | Y | Q | F | T |
| 296 | G | C | R | W | G | T | C | T | V | Q | Cit | L | A | H | Q | I | Y | Q | F | T |
| 297 | G | C | R | T | G | T | C | T | V | Q | Cit | L | A | H | Q | I | Y | Q | F | T |
| 298 | G | C | R | T | G | T | C | T | V | Q | Cit | L | A | H | Q | I | Y | Q | F | T |
| 299 | G | C | R | T | G | T | C | T | V | Q | Cit | L | A | H | Q | I | Y | Q | F | T |
| 300 | G | C | R | F | G | T | C | T | V | Q | Cit | L | A | H | Q | I | Y | Q | F | T |
| 301 | G | C | R | T | G | T | C | T | V | Q | Cit | L | A | H | Q | I | Y | Q | F | T |
| 302 | G | C | R | T | G | T | C | T | V | Q | Cit | L | A | H | Q | I | Y | Q | F | T |
| 303 | G | C | R | T | G | T | C | T | V | Q | Cit | L | A | H | Q | I | Y | Q | F | T |
| 304 | G | C | R | T | G | T | C | T | V | Q | Cit | L | A | H | Q | I | Y | Q | F | T |
| 305 | G | C | R | F | G | T | C | T | V | Q | Cit | L | A | H | Q | I | Y | Q | F | T |
| 306 | K | C | N | T | S | T | C | T | V | A | W | L | A | D | Q | I | T | Q | F | S |
| 307 | R | C | N | A | S | T | C | T | V | N | W | L | A | D | Q | I | T | Q | F | S |
| 308 | K | C | N | T | A | T | C | T | V | Q | W | L | A | H | A | I | Y | Q | F | T |
| 309 | K | C | N | T | A | T | C | T | V | Q | W | L | A | H | Q | I | A | Q | F | T |
| 310 | K | C | N | T | S | T | C | T | V | A | W | L | A | D | Q | I | T | Q | F | S |
| 311 | G | C | R | F | G | T | C | T | V | Q | W | L | A | N | F | L | Y | Q | F | T |
| 312 | K | C | N | T | A | T | C | T | V | Q | W | L | A | H | Q | I | Y | Q | F | T |
| 313 | K | C | N | T | A | T | C | T | V | Q | W | L | A | H | Q | I | Y | Q | F | A |
| 314 | K | C | N | T | A | T | C | T | V | Q | W | L | A | H | Q | I | Y | Q | F | T |
| 315 | K | C | N | T | A | T | C | T | V | Q | W | L | A | H | Q | I | Y | Q | F | T |
| 316 | K | C | N | T | A | T | C | T | V | Q | W | L | A | H | Q | I | Y | Q | F | T |
| 317 | K | C | N | T | A | T | C | T | V | Q | W | L | A | H | Q | I | Y | Q | F | — |
| 318 | K | C | N | T | A | T | C | T | V | Q | W | L | A | H | Q | I | Y | Q | F | T |
| 319 | K | C | N | T | A | T | C | T | V | Q | W | L | A | H | Q | I | Y | Q | F | T |
| 320 | K | C | N | T | A | T | C | T | V | Q | W | L | A | H | Q | I | Y | Q | F | T |
| 321 | K | C | N | T | A | T | C | T | V | Q | W | L | A | E | Q | I | Y | Q | F | T |
| 322 | G | C | R | F | G | T | C | T | V | Q | W | L | A | H | Q | I | Y | Q | F | T |
| 323 | G | C | R | T | G | T | C | T | V | Q | W | L | A | H | Q | I | Y | Q | F | T |
| 324 | K | C | N | T | A | T | C | T | V | Q | W | L | A | H | Q | I | Y | Q | F | T |
| 325 | K | C | N | T | A | T | C | T | V | Q | W | L | A | H | Q | I | Y | Q | F | T |
| 326 | G | C | R | F | G | T | C | T | V | Q | W | L | A | H | F | L | Y | Q | F | T |
| 327 | G | C | R | F | G | T | C | T | V | Q | W | L | A | H | F | L | Y | Q | F | T |
| 328 | K | C | N | T | A | T | C | T | V | Q | W | L | A | H | Q | I | Y | Q | F | T |
| 329 | K | C | N | T | A | T | C | T | V | Q | W | L | A | H | Q | I | Y | Q | F | — |
| 330 | K | C | N | T | A | T | C | T | V | Q | W | L | A | H | Q | I | Y | Q | F | T |
| 331 | G | C | R | F | G | T | C | T | V | Q | W | L | A | H | Q | I | Y | Q | F | T |
| 332 | G | C | R | T | G | T | C | T | V | Q | W | L | A | H | Q | I | Y | Q | F | T |
| 333 | K | C | N | A | A | T | C | T | V | Q | W | L | A | E | Q | I | Y | Q | F | T |
| 334 | K | C | N | T | A | T | C | T | V | Q | W | L | A | H | Q | I | Y | Q | F | T |

TABLE 7-continued

SEQUENCE LISTING

| | | | | | | | | | | | | | | | | | | | |
|---|---|---|---|---|---|---|---|---|---|---|---|---|---|---|---|---|---|---|---|
| 335 | G | C | R | T | G | T | C | T | V | Q | W | L | A | H | Q | I | Y | Q | F | T |
| 336 | G | C | R | F | G | T | C | T | V | Q | W | L | A | H | Q | I | Y | Q | F | T |
| 337 | G | C | R | F | G | T | C | T | V | Q | W | L | A | H | Q | I | Y | Q | F | T |
| 338 | K | C | N | T | A | T | C | T | V | Q | W | L | A | H | Q | I | Y | Q | A | T |
| 339 | G | C | R | T | G | T | C | T | V | Q | W | L | A | H | Q | I | Y | Q | F | T |
| 340 | G | C | R | F | G | T | C | T | V | Q | W | L | A | H | Q | I | Y | Q | F | T |
| 341 | G | C | R | T | G | T | C | T | V | Q | W | L | A | H | Q | I | Y | Q | F | T |
| 342 | G | C | R | T | G | T | C | T | V | Q | W | L | A | H | Q | I | Y | Q | F | T |
| 343 | G | C | R | F | G | T | C | T | V | Q | W | L | A | H | Q | I | Y | Q | F | T |
| 344 | G | C | R | T | G | T | C | T | V | Q | W | L | A | H | Q | I | Y | Q | F | T |
| 345 | G | C | R | F | G | T | C | T | V | Q | W | L | A | H | Q | I | Y | Q | F | T |
| 346 | G | C | R | T | G | T | C | T | V | Q | W | L | A | H | Q | I | Y | Q | F | T |
| 347 | G | C | R | T | G | T | C | T | V | Q | W | L | A | H | Q | I | Y | Q | F | T |
| 348 | G | C | R | T | G | T | C | T | V | Q | W | L | A | H | Q | I | Y | Q | F | T |
| 349 | G | C | R | T | G | T | C | T | V | Q | W | L | A | H | Q | I | Y | Q | F | T |
| 350 | G | C | R | F | G | T | C | T | V | Q | W | L | A | H | Q | I | Y | Q | F | T |
| 351 | G | C | R | I | G | T | C | T | V | Q | W | L | A | H | Q | I | Y | Q | F | T |
| 352 | G | C | R | T | G | T | C | T | V | Q | W | L | A | H | Q | I | Y | Q | F | T |
| 353 | G | C | R | F | G | T | C | T | V | Q | W | L | A | H | Q | I | Y | Q | F | T |
| 354 | G | C | R | T | G | T | C | T | V | Q | W | L | A | H | Q | I | Y | Q | F | T |
| 355 | G | C | R | T | G | T | C | T | V | Q | W | L | A | H | Q | I | Y | Q | F | T |
| 356 | G | C | R | T | G | T | C | T | V | Q | W | L | A | H | Q | I | Y | Q | F | T |
| 357 | G | C | R | T | G | T | C | T | V | Q | W | L | A | H | Q | I | Y | Q | F | T |
| 358 | G | C | R | T | G | T | C | T | V | Q | W | L | A | H | Q | I | Y | Q | F | T |
| 359 | G | C | R | T | G | T | C | T | V | Q | W | L | A | H | Q | I | Y | Q | F | T |
| 360 | G | C | R | T | G | T | C | T | V | Q | W | L | A | H | Q | I | Y | Q | F | T |
| 361 | K | C | N | F | A | T | C | T | V | Q | R | L | A | H | Q | I | Y | Q | F | T |
| 362 | G | C | R | F | G | T | C | T | V | Q | R | L | A | H | Q | I | Y | Q | F | T |
| 363 | K | C | N | F | A | T | C | A | T | Q | R | L | A | N | F | L | V | Q | F | T |
| 364 | G | C | R | F | G | T | C | T | V | Q | R | L | A | H | F | L | Y | Q | F | T |
| 365 | G | C | R | F | G | T | C | T | V | Q | R | L | A | H | F | L | Y | Q | F | T |
| 366 | G | C | R | F | G | T | C | T | V | Q | R | L | A | H | Q | I | Y | Q | F | T |
| 367 | G | C | R | F | G | T | C | T | V | Q | R | L | A | H | Q | I | Y | Q | F | T |
| 368 | G | C | R | F | G | T | C | T | V | Q | R | L | A | H | Q | I | Y | Q | F | T |
| 369 | G | C | R | F | G | T | C | T | V | Q | R | L | A | H | F | L | Y | Q | F | T |
| 370 | K | C | N | F | A | T | C | T | V | Q | R | L | A | H | Q | I | Y | Q | F | T |
| 371 | G | C | R | F | G | T | C | T | V | Q | R | L | A | H | Q | I | Y | Q | F | T |
| 372 | G | C | R | F | G | T | C | T | V | Q | R | L | A | N | Q | I | Y | Q | F | T |
| 373 | G | C | R | F | G | T | C | T | V | Q | R | L | A | H | Q | I | Y | Q | F | T |
| 374 | G | C | R | F | G | T | C | T | V | Q | R | L | A | H | Q | I | Y | Q | F | T |
| 375 | G | C | R | F | G | T | C | T | V | Q | R | L | A | H | Q | I | Y | Q | F | T |
| 376 | G | C | R | F | G | T | C | T | V | Q | R | L | A | H | F | L | Y | Q | F | T |
| 377 | G | C | R | F | A | T | C | T | V | Q | R | L | A | H | F | L | Y | Q | F | T |
| 378 | K | C | N | F | A | T | C | T | V | Q | R | L | A | H | Q | I | Y | Q | F | T |
| 379 | G | C | R | F | G | T | C | T | V | Q | R | L | A | H | Q | I | Y | Q | F | T |
| 380 | G | C | R | F | A | T | C | T | V | Q | R | L | A | H | Q | I | Y | Q | F | T |
| 381 | G | C | R | F | G | T | C | T | V | Q | R | L | A | H | Q | I | Y | Q | F | T |
| 382 | G | C | R | F | G | T | C | T | V | Q | R | L | A | H | Q | I | Y | Q | F | T |
| 383 | G | C | R | F | G | T | C | T | V | Q | R | L | A | H | Q | I | Y | Q | F | T |
| 384 | G | C | R | F | G | T | C | T | V | Q | R | L | A | H | Q | I | Y | Q | F | T |
| 385 | G | C | R | F | G | T | C | T | V | Q | R | L | A | H | Q | I | Y | Q | F | T |
| 386 | G | C | R | F | G | T | C | T | V | Q | R | L | A | N | F | L | Y | Q | F | T |
| 387 | G | C | R | F | G | T | C | T | V | Q | R | L | A | H | Q | I | Y | Q | F | T |
| 388 | G | C | R | F | G | T | C | T | V | Q | R | L | A | H | F | L | Y | Q | F | T |
| 389 | K | C | N | F | A | T | C | A | T | Q | R | L | A | N | F | L | V | Q | F | T |
| 390 | G | C | R | F | G | T | C | T | V | Q | R | L | A | H | F | L | Y | Q | F | T |
| 391 | G | C | R | F | G | T | C | T | V | Q | R | L | A | H | Q | I | Y | Q | F | T |
| 392 | G | C | R | F | G | T | C | T | V | Q | R | L | A | H | F | L | Y | Q | F | T |

| ID | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|
| 1 | D | K | D | K | D | N | V | A | P | R | S | K | I | S | P | Q | G | Y |
| 2 | N | N | F | — | G | A | I | L | S | S | T | N | V | G | S | N | T | Y |
| 3 | D | K | D | K | D | N | V | A | P | R | T | K | V | G | S | N | G | Hyp |
| 4 | D | K | D | K | D | N | V | A | P | P | T | N | V | G | S | N | G | Hyp |
| 5 | D | K | D | K | D | N | V | A | P | P | T | N | V | G | S | N | G | Hyp |
| 6 | D | K | D | K | D | N | V | A | P | P | T | N | V | G | S | K | G | Hyp |
| 7 | D | K | D | K | D | N | V | A | P | P | T | N | V | G | S | N | G | Hyp |
| 8 | N | K | D | K | A | Q | V | S | P | P | T | E | V | G | P | N | S | Hyp |
| 9 | N | K | D | K | A | Q | V | S | P | P | T | E | V | G | P | N | S | Hyp |
| 10 | D | K | D | K | D | N | V | A | P | P | T | E | V | G | S | N | G | Hyp |
| 11 | D | K | D | K | D | N | V | A | P | P | T | N | V | G | S | N | G | Hyp |
| 12 | D | K | D | K | D | N | K | A | P | P | T | N | V | G | S | N | G | Hyp |
| 13 | D | K | D | K | D | N | V | A | P | P | T | N | V | G | S | N | G | Hyp |
| 14 | D | K | D | K | D | N | V | A | P | P | T | N | V | G | S | N | G | Hyp |
| 15 | D | K | D | K | A | N | V | S | P | P | T | E | V | G | P | N | S | Hyp |
| 16 | D | K | D | K | D | N | V | A | P | R | T | N | V | G | P | Q | G | Y |
| 17 | D | K | D | K | D | N | V | A | P | R | T | E | V | G | S | N | G | Hyp |

TABLE 7-continued

SEQUENCE LISTING

| | | | | | | | | | | | | | | | | |
|---|---|---|---|---|---|---|---|---|---|---|---|---|---|---|---|---|
| 18 | D | K | D | K | D | N | V | A | P | P | T | E | V | G | S | N | G | P |
| 19 | N | N | F | G | A | — | I | L | P | R | T | K | V | G | S | N | G | Y |
| 20 | D | K | D | K | D | N | V | A | R | T | K | V | G | S | N | G | Hyp |
| 21 | D | K | D | K | D | N | V | A | P | P | T | N | V | G | S | N | G | Hyp |
| 22 | D | K | D | K | D | N | V | A | P | P | T | N | V | G | S | N | G | Hyp |
| 23 | D | K | D | K | D | N | V | A | P | P | T | N | V | G | S | N | G | Hyp |
| 24 | A | K | D | K | D | N | V | A | P | P | T | N | V | G | S | N | G | Hyp |
| 25 | D | K | D | A | D | N | V | A | P | P | T | N | V | G | S | N | G | Hyp |
| 26 | D | K | D | K | A | N | V | A | P | P | T | N | V | G | S | N | G | Hyp |
| 27 | D | K | D | K | D | N | A | A | P | P | T | N | V | G | S | N | G | Hyp |
| 28 | D | K | D | K | D | N | V | A | P | A | T | N | V | G | S | N | G | Hyp |
| 29 | T | K | D | K | D | N | V | A | P | P | T | N | V | G | S | N | G | Hyp |
| 30 | D | K | D | K | D | N | V | — | P | P | T | N | V | G | S | N | G | Hyp |
| 31 | D | K | D | K | D | N | V | — | A | P | T | N | V | G | S | N | G | Hyp |
| 32 | D | K | D | K | D | Q | V | A | P | P | T | N | V | G | S | N | S | Hyp |
| 33 | D | K | D | K | D | Q | V | A | P | P | T | E | V | G | P | N | S | Hyp |
| 34 | D | K | D | K | D | N | V | A | P | R | T | K | V | G | S | N | G | Y |
| 35 | D | K | D | K | D | N | V | A | P | P | T | N | V | G | S | N | G | Hyp |
| 36 | D | K | D | K | D | N | V | A | P | P | T | N | V | G | S | N | G | Hyp |
| 37 | D | K | D | K | D | N | V | A | P | P | T | N | V | G | S | N | G | Hyp |
| 38 | D | K | D | K | D | N | V | A | P | P | T | N | V | G | S | N | G | Hyp |
| 39 | D | K | D | K | D | N | V | A | P | P | T | N | V | G | S | N | G | Hyp |
| 40 | D | K | D | K | K | N | V | A | P | P | T | N | V | G | S | N | G | Hyp |
| 41 | D | K | D | K | D | K | V | A | P | P | T | N | V | G | S | N | G | Hyp |
| 42 | D | K | D | K | D | N | V | A | P | P | T | N | V | G | S | N | G | Hyp |
| 43 | D | K | A | K | D | N | V | A | P | P | T | N | V | G | S | N | G | Hyp |
| 44 | D | K | D | K | D | N | V | A | P | P | Y | N | E | G | S | N | G | Hyp |
| 45 | D | K | D | K | D | N | V | A | P | R | T | K | V | G | P | Q | G | Hyp |
| 46 | D | K | D | K | D | N | V | A | P | R | T | N | I | G | P | Q | G | Hyp |
| 47 | D | K | D | K | D | N | V | A | P | P | T | N | V | G | S | N | G | Hyp |
| 48 | D | K | D | K | D | N | V | A | P | P | T | N | V | G | S | N | G | Hyp |
| 49 | D | K | D | K | D | N | V | A | P | R | T | N | V | G | P | Q | G | Hyp |
| 50 | D | K | D | K | D | N | V | A | P | P | T | N | V | G | S | N | G | Hyp |
| 51 | D | K | D | K | D | N | V | A | P | P | T | N | V | G | S | N | G | Hyp |
| 52 | D | K | D | K | D | A | V | A | P | P | T | N | V | G | S | N | G | Hyp |
| 53 | D | K | D | K | D | N | V | A | A | P | T | N | V | G | S | N | G | Hyp |
| 54 | D | K | D | K | D | N | V | A | P | R | T | N | V | G | P | Q | G | Y |
| 55 | D | K | D | K | D | N | V | A | P | P | T | N | V | G | S | N | G | Hyp |
| 56 | D | K | D | K | D | N | V | A | P | R | T | N | V | G | S | N | T | Y |
| 57 | D | K | D | K | D | N | V | A | P | P | T | N | V | G | S | N | G | Hyp |
| 58 | N | N | F | G | A | — | I | L | S | S | T | K | V | G | S | N | T | Y |
| 59 | N | N | F | G | A | — | I | L | P | S | T | K | V | G | S | N | G | Y |
| 60 | D | K | D | K | D | N | V | A | P | P | T | K | V | G | S | N | G | Hyp |
| 61 | D | K | D | K | D | N | V | A | P | P | T | N | V | G | S | N | G | Hyp |
| 62 | D | K | D | K | D | N | V | A | P | P | T | N | V | G | S | N | G | Hyp |
| 63 | D | K | D | K | D | N | V | A | P | P | T | A | V | G | S | N | G | Hyp |
| 64 | D | A | D | K | D | N | V | A | P | P | T | N | V | G | S | N | G | Hyp |
| 65 | D | K | D | K | D | N | V | A | P | P | T | N | V | G | S | N | G | Hyp |
| 66 | D | K | D | K | D | N | V | S | P | P | T | N | V | G | S | N | G | Hyp |
| 67 | D | K | D | K | D | N | V | A | P | R | T | E | V | G | S | N | G | Hyp |
| 68 | D | K | D | K | D | N | V | A | P | P | T | E | V | G | S | N | G | Hyp |
| 69 | D | K | D | K | D | N | V | A | P | P | T | N | V | G | S | N | S | Hyp |
| 70 | D | K | D | K | D | N | V | A | P | R | T | N | V | G | P | Q | G | Hyp |
| 71 | D | K | D | K | D | N | V | A | P | P | T | N | V | G | S | N | G | Hyp |
| 72 | D | K | D | K | D | N | V | A | P | P | T | N | V | G | S | N | G | Hyp |
| 73 | D | K | D | K | D | N | V | A | P | P | T | Q | V | G | S | N | G | Hyp |
| 74 | D | K | D | K | D | N | V | A | P | P | T | N | V | G | S | N | G | Hyp |
| 75 | D | K | D | K | D | N | V | A | P | P | T | N | V | G | S | N | G | Hyp |
| 76 | — | S | F | (NMe)G | A | — | (NMe)I | L | S | S | T | E | V | G | S | N | T | Hyp |
| 77 | D | K | D | K | D | N | V | A | P | P | T | N | V | G | S | N | G | Hyp |
| 78 | D | K | D | K | D | N | V | A | P | P | T | N | V | G | S | N | G | Hyp |
| 79 | D | K | D | K | D | N | V | A | P | P | T | N | V | G | S | N | G | Hyp |
| 80 | — | S | F | (NMe)G | A | — | (NMe)I | L | S | S | T | E | V | G | S | N | T | Hyp |
| 81 | D | K | D | K | D | N | V | A | P | R | T | N | I | G | P | N | G | Hyp |
| 82 | N | K | D | K | D | N | V | A | P | P | T | N | V | G | S | N | G | Hyp |
| 83 | D | K | D | K | D | N | V | A | P | P | T | N | V | G | S | N | G | Hyp |
| 84 | D | K | D | K | D | N | V | A | P | R | T | N | V | G | P | N | G | Y |
| 85 | D | K | D | K | D | N | V | A | P | P | T | N | V | G | S | N | G | Hyp |
| 86 | D | K | D | K | D | N | V | A | P | P | T | N | V | G | S | N | G | Hyp |
| 87 | D | K | N | K | D | N | V | A | P | P | T | N | V | G | S | N | G | Hyp |
| 88 | D | K | D | K | D | P | V | A | P | P | T | N | V | G | S | N | G | Hyp |
| 89 | D | K | D | K | D | N | V | A | P | R | T | N | V | G | P | N | G | Y |
| 90 | D | K | D | K | D | N | V | A | P | R | T | N | V | G | P | N | G | Y |
| 91 | D | K | N | K | D | N | V | A | P | P | T | N | V | G | S | N | G | Hyp |
| 92 | D | K | D | K | D | P | V | A | P | P | T | N | V | G | S | N | G | Hyp |
| 93 | N | N | F | G | A | — | I | A | P | S | T | K | V | G | S | N | G | Y |
| 94 | D | K | D | K | D | N | V | A | P | P | T | N | V | G | S | N | G | Hyp |
| 95 | N | K | D | K | D | N | V | A | P | P | T | N | V | G | S | N | G | Hyp |

TABLE 7-continued

SEQUENCE LISTING

| 96 | D | K | D | K | D | N | V | A | P | P | T | N | V | G | S | N | T | Hyp |
|---|---|---|---|---|---|---|---|---|---|---|---|---|---|---|---|---|---|---|
| 97 | D | K | D | K | D | N | V | A | P | P | T | N | V | G | S | N | G | Hyp |
| 98 | D | K | D | K | D | N | V | A | P | R | T | N | V | S | P | N | G | Y |
| 99 | D | K | D | K | D | N | V | A | P | R | T | K | V | G | S | N | G | Hyp |
| 100 | D | K | D | K | D | Q | V | A | P | P | T | N | V | G | S | N | G | Hyp |
| 101 | D | K | D | K | D | N | V | A | P | P | T | N | V | G | S | N | G | Hyp |
| 102 | D | K | D | K | D | N | V | A | P | R | T | E | V | G | S | N | G | Y |
| 103 | D | K | D | K | D | N | V | A | P | P | T | N | V | G | S | N | G | Hyp |
| 104 | D | K | D | K | D | N | V | A | P | P | T | N | V | G | S | N | G | Hyp |
| 105 | D | K | D | K | D | N | V | A | P | P | T | N | V | G | S | N | G | Hyp |
| 106 | A | K | D | K | D | N | V | A | P | P | T | N | V | G | S | N | G | Hyp |
| 107 | D | K | D | K | D | N | V | A | P | P | T | N | V | G | S | N | G | Hyp |
| 108 | D | K | D | K | A | N | V | A | P | P | T | N | V | G | S | N | G | Hyp |
| 109 | D | K | D | K | D | N | V | A | P | R | T | N | V | G | P | Q | G | Y |
| 110 | D | K | D | K | D | N | V | A | P | P | T | N | V | G | S | N | G | Hyp |
| 111 | D | K | D | K | D | N | V | A | P | R | T | K | I | G | P | Q | G | Hyp |
| 112 | D | K | D | K | D | N | V | A | P | P | T | N | V | G | S | N | G | Hyp |
| 113 | D | K | D | K | D | N | V | A | P | R | T | K | I | S | P | N | G | Hyp |
| 114 | D | K | D | K | D | N | V | A | P | P | T | N | V | G | S | N | G | Hyp |
| 115 | D | K | D | K | D | N | V | A | P | R | T | K | I | G | P | N | G | Hyp |
| 116 | D | K | D | K | D | N | V | A | P | R | T | N | V | S | P | Q | G | Y |
| 117 | D | K | D | K | D | N | V | A | P | R | T | K | V | G | S | N | G | Y |
| 118 | D | K | D | K | D | N | V | A | P | R | T | N | I | G | P | Q | G | Hyp |
| 119 | D | K | D | K | D | N | V | A | P | P | T | N | V | G | S | N | G | Hyp |
| 120 | D | K | D | K | D | P | V | A | P | P | T | N | V | G | S | N | S | Hyp |
| 121 | D | K | D | K | D | N | V | A | P | R | S | N | V | G | P | Q | G | Hyp |
| 122 | D | K | A | K | D | N | V | A | P | P | T | N | V | G | S | N | G | Hyp |
| 123 | D | K | D | G | A | — | I | A | P | R | T | K | I | G | S | Q | G | Y |
| 124 | D | K | D | K | D | N | V | A | P | R | T | K | I | G | P | N | G | Hyp |
| 125 | D | K | D | K | D | N | V | A | P | R | T | N | V | S | P | Q | G | Y |
| 126 | D | K | D | K | D | N | V | A | P | P | T | N | V | G | S | N | G | Hyp |
| 127 | D | K | D | K | D | N | V | A | P | R | S | K | I | G | P | O | G | Hyp |
| 128 | N | N | F | G | A | — | I | A | P | S | T | K | I | G | P | N | G | Y |
| 129 | D | K | D | K | D | N | V | A | P | R | S | K | V | G | P | Q | G | Y |
| 130 | D | K | D | K | D | P | V | A | P | P | T | N | V | G | S | N | G | Hyp |
| 131 | D | K | D | K | D | N | V | A | P | R | S | N | V | S | P | Q | G | Y |
| 132 | D | K | D | K | D | N | V | A | P | R | T | K | V | S | P | Q | G | Hyp |
| 133 | D | K | D | K | D | P | V | A | P | P | T | N | V | G | S | N | G | Hyp |
| 134 | D | K | D | K | D | N | V | A | P | R | T | K | V | S | P | N | G | Hyp |
| 135 | D | K | D | K | D | N | V | A | P | R | S | N | V | G | P | Q | G | Y |
| 136 | D | K | D | K | D | N | V | A | P | P | T | N | V | G | S | N | G | Hyp |
| 137 | D | K | D | K | D | P | V | A | P | P | T | N | V | G | S | N | G | Hyp |
| 138 | D | K | D | K | D | N | V | A | P | R | S | N | V | G | P | Q | G | Y |
| 139 | D | K | D | K | D | N | V | A | P | R | S | K | V | G | P | N | G | Hyp |
| 140 | D | K | D | K | D | N | V | A | P | R | T | N | I | S | P | Q | G | Y |
| 141 | D | K | D | K | D | N | V | A | P | R | T | N | I | S | P | Q | G | Hyp |
| 142 | D | K | D | K | D | N | V | A | P | R | T | N | I | G | P | N | G | Y |
| 143 | D | K | D | K | D | N | V | A | P | R | T | K | V | G | P | Q | G | Hyp |
| 144 | D | K | D | K | D | P | V | A | P | P | T | N | V | G | S | N | G | Hyp |
| 145 | D | K | D | K | D | N | V | A | P | R | S | N | V | S | P | Q | G | Hyp |
| 146 | D | K | D | K | D | N | V | A | P | R | S | K | I | S | P | Q | G | Hyp |
| 147 | D | K | F | K | D | N | V | A | P | R | S | K | I | S | P | Q | T | Hyp |
| 148 | N | N | F | G | A | — | I | L | S | S | T | K | I | G | S | N | G | Y |
| 149 | N | N | F | G | A | — | I | L | P | S | T | K | V | G | P | N | G | Y |
| 150 | D | K | D | K | D | N | V | A | P | R | S | K | I | S | P | Q | T | Hyp |
| 151 | D | K | D | K | D | N | V | A | P | R | S | N | I | G | P | N | G | Hyp |
| 152 | D | K | D | K | D | N | V | A | P | R | S | K | V | G | P | Q | G | Hyp |
| 153 | D | K | D | K | D | N | V | A | P | P | T | N | V | G | S | N | G | Hyp |
| 154 | D | K | D | K | D | N | V | A | P | R | S | K | I | S | P | Q | G | Y |
| 155 | D | K | D | K | D | N | V | A | P | R | T | K | V | S | P | Q | G | Y |
| 156 | D | K | D | K | D | N | V | A | P | R | T | K | V | G | P | Q | G | Y |
| 157 | D | K | D | K | D | N | V | A | P | R | S | K | I | S | P | Q | G | Hyp |
| 158 | D | K | D | K | D | N | V | A | P | R | S | N | I | S | P | Q | G | Hyp |
| 159 | D | K | D | K | D | N | V | A | P | P | T | N | V | G | S | N | G | Hyp |
| 160 | D | K | D | K | D | N | V | A | P | R | T | N | I | S | P | Q | G | Y |
| 161 | D | K | D | K | D | N | V | A | P | R | T | K | I | G | P | Q | G | Hyp |
| 162 | N | N | F | G | A | — | I | L | P | S | T | K | I | G | P | N | G | Y |
| 163 | D | K | D | K | D | N | V | A | P | R | T | N | V | S | P | N | G | Hyp |
| 164 | D | K | D | K | D | N | V | A | P | R | T | K | I | S | P | Q | G | Y |
| 165 | D | K | D | K | D | N | V | A | P | R | S | N | I | G | P | Q | G | Hyp |
| 166 | D | K | D | K | D | N | V | A | P | R | S | N | V | S | P | N | G | Hyp |
| 167 | D | K | D | K | D | N | V | A | P | R | S | K | V | S | P | Q | G | Hyp |
| 168 | D | K | D | K | D | N | V | A | P | R | S | K | I | S | P | Q | T | Hyp |
| 169 | D | K | D | K | D | N | V | A | P | R | S | K | I | S | P | Q | T | Hyp |
| 170 | D | K | D | K | D | N | V | A | P | R | T | N | I | S | P | N | G | Hyp |
| 171 | D | K | F | K | D | N | V | A | P | R | S | K | I | S | P | Q | T | Hyp |
| 172 | D | K | D | K | D | N | V | A | P | R | S | N | V | S | P | N | G | Y |
| 173 | D | K | F | K | D | N | V | A | P | R | S | K | I | S | P | Q | T | Hyp |

TABLE 7-continued

SEQUENCE LISTING

| 174 | D | K | D | K | D | N | V | A | P | R | S | K | V | S | P | Q | G | Y |
|---|---|---|---|---|---|---|---|---|---|---|---|---|---|---|---|---|---|---|
| 175 | D | K | D | K | D | N | V | A | P | R | S | K | V | S | P | N | G | Hyp |
| 176 | D | K | D | K | D | N | V | A | P | R | T | N | V | S | P | Q | G | Y |
| 177 | D | K | D | K | D | N | V | A | P | R | S | N | V | G | P | N | G | Y |
| 178 | D | K | D | K | D | N | V | A | P | R | T | N | V | S | P | Q | G | Hyp |
| 179 | D | K | D | K | D | N | V | A | P | R | S | K | I | G | P | Q | G | Hyp |
| 180 | N | N | F | G | A | — | I | L | P | S | T | K | I | G | S | N | T | Y |
| 181 | D | K | D | K | D | N | V | A | P | P | T | N | V | G | S | N | G | Hyp |
| 182 | D | K | D | K | D | N | V | A | P | R | S | N | I | S | P | Q | G | Y |
| 183 | D | K | D | K | D | N | V | A | P | R | S | N | V | S | P | Q | G | Y |
| 184 | D | K | F | K | D | N | V | A | P | R | S | K | I | S | P | Q | T | W |
| 185 | D | K | F | K | D | N | V | A | P | R | S | K | I | S | P | Q | W | Hyp |
| 186 | D | K | F | K | D | N | V | A | P | R | S | K | I | S | P | Q | Y | HYP |
| 187 | D | K | D | K | D | N | V | A | P | R | S | K | V | G | P | Q | G | Hyp |
| 188 | D | K | D | K | D | N | V | A | P | R | T | N | I | S | P | N | G | Y |
| 189 | D | K | D | K | D | N | V | A | P | R | T | K | I | S | P | Q | G | Hyp |
| 190 | D | K | D | K | D | N | V | A | P | R | T | K | I | S | P | N | G | Y |
| 191 | D | K | D | K | D | N | V | A | P | R | S | N | I | G | P | Q | G | Y |
| 192 | N | K | D | K | D | N | V | A | P | R | S | K | I | S | P | Q | T | Hyp |
| 193 | D | K | F | K | D | N | V | A | P | R | S | K | I | S | P | Q | T | Hyp |
| 194 | D | K | D | K | D | N | V | A | P | R | S | K | I | S | P | Q | T | Hyp |
| 195 | D | K | D | K | D | N | V | A | P | P | T | N | V | G | S | N | G | Hyp |
| 196 | D | K | F | K | D | N | V | A | P | R | S | K | I | S | P | Q | T | Hyp |
| 197 | D | K | D | K | D | N | V | A | P | R | T | K | I | S | P | N | G | Hyp |
| 198 | N | K | D | K | D | N | V | A | P | R | S | K | I | S | P | Q | T | Hyp |
| 199 | D | K | D | K | D | N | V | A | P | R | T | N | I | S | P | Q | G | Y |
| 200 | D | K | D | K | D | N | V | A | P | R | T | N | V | G | P | Q | G | Y |
| 201 | D | K | F | K | D | N | V | A | P | R | S | K | I | S | P | Q | H | Hyp |
| 202 | D | K | D | K | D | N | V | A | P | S | S | K | I | S | P | Q | T | Hyp |
| 203 | D | K | F | K | D | N | V | A | P | R | S | K | I | S | P | Q | P | Hyp |
| 204 | D | K | D | K | D | N | V | A | P | R | S | K | V | S | P | N | G | Hyp |
| 205 | D | K | D | K | D | N | V | A | P | R | S | K | I | S | P | Q | T | Hyp |
| 206 | D | K | F | K | D | N | V | A | P | R | S | K | I | S | P | Q | K | Hyp |
| 207 | N | N | F | G | A | — | I | L | P | S | T | K | I | G | S | N | G | Y |
| 208 | D | K | D | K | D | N | V | A | P | R | T | N | V | G | S | N | T | Y |
| 209 | D | K | D | K | D | N | V | A | P | R | T | K | V | S | P | Q | G | Y |
| 210 | D | K | D | K | D | N | V | A | P | P | T | N | V | G | S | N | G | Hyp |
| 211 | D | K | F | K | D | N | V | A | P | R | S | K | I | S | P | Q | F | Hyp |
| 212 | D | K | F | K | D | N | V | A | P | R | S | K | I | S | P | Q | T | Hyp |
| 213 | D | K | F | K | D | N | V | A | P | R | S | K | I | S | P | Q | T | Hyp |
| 214 | D | K | D | K | D | N | V | A | P | R | T | N | I | S | P | Q | G | Hyp |
| 215 | D | K | F | K | D | N | V | A | P | R | S | K | I | S | P | Q | T | M |
| 216 | D | K | D | K | D | N | V | A | P | R | T | K | V | S | P | Q | G | Hyp |
| 217 | D | K | D | K | D | N | V | A | P | R | S | K | I | S | P | Q | T | Hyp |
| 218 | D | K | F | K | D | N | V | A | P | R | S | K | I | S | P | Q | A | Hyp |
| 219 | N | K | D | K | D | N | V | A | P | R | S | K | I | S | P | Q | H | Hyp |
| 220 | N | K | D | K | D | N | V | A | P | R | S | K | I | S | P | Q | W | Hyp |
| 221 | D | K | D | K | D | N | V | A | P | P | T | N | V | G | S | N | G | Hyp |
| 222 | D | K | D | K | D | N | V | A | P | S | S | K | I | S | P | Q | T | Hyp |
| 223 | D | K | D | K | D | N | V | A | P | R | T | K | V | G | S | N | G | Y |
| 224 | D | K | D | K | D | N | V | A | P | R | S | N | V | S | P | Q | G | Hyp |
| 225 | D | K | D | K | D | N | V | A | P | P | T | N | V | G | S | N | G | Hyp |
| 226 | N | K | D | K | D | N | V | A | P | R | S | K | I | S | P | Q | T | W |
| 227 | N | K | D | K | D | N | V | A | P | R | S | K | I | S | P | Q | T | Hyp |
| 228 | D | K | D | K | D | N | V | A | P | R | S | K | I | S | P | Q | T | Hyp |
| 229 | D | K | D | K | D | N | V | A | P | R | S | N | I | G | P | Q | G | Hyp |
| 230 | D | K | F | K | D | N | V | A | P | R | S | K | I | S | P | Q | T | Y |
| 231 | D | K | D | K | D | N | V | A | P | P | T | N | V | G | S | N | G | Hyp |
| 232 | N | K | D | K | D | N | V | A | P | R | S | K | I | S | P | Q | Q | Hyp |
| 233 | D | K | D | K | D | N | V | A | P | P | T | N | V | G | S | N | G | Hyp |
| 234 | D | K | D | K | D | N | V | A | P | R | S | K | I | S | P | Q | G | Y |
| 235 | D | K | F | K | D | N | V | A | P | R | S | K | I | S | P | Q | T | P |
| 236 | D | K | F | K | D | N | V | A | P | R | S | K | I | S | P | Q | M | Hyp |
| 237 | N | K | D | K | D | N | V | A | P | R | S | K | I | S | P | Q | T | M |
| 238 | N | K | D | K | D | N | V | A | P | R | S | K | I | S | P | Q | F | Hyp |
| 239 | D | K | F | K | D | N | V | A | P | R | S | K | I | S | P | Q | T | F |
| 240 | D | K | D | K | D | N | V | A | P | S | S | K | I | S | P | Q | T | Hyp |
| 241 | D | K | F | K | D | N | V | A | P | R | S | K | I | S | P | Q | T | A |
| 242 | N | K | D | K | D | N | V | A | P | R | S | K | I | S | P | Q | T | R |
| 243 | D | K | D | K | D | N | V | A | P | P | T | N | V | G | S | N | G | Hyp |
| 244 | N | K | D | K | A | Q | V | S | P | P | T | E | V | G | P | N | S | Hyp |
| 245 | N | K | D | K | A | Q | V | S | P | P | T | E | V | G | P | N | S | Hyp |
| 246 | D | K | D | K | D | N | V | A | P | P | T | N | V | G | S | N | G | Hyp |
| 247 | D | K | D | K | A | N | V | S | P | P | T | E | V | G | P | N | S | Hyp |
| 248 | D | K | D | K | D | N | V | A | P | R | T | K | V | G | S | N | G | Hyp |
| 249 | D | K | D | K | D | N | V | A | P | P | T | N | V | G | S | N | G | Hyp |
| 250 | D | K | D | A | D | N | V | A | P | P | T | N | V | G | S | N | G | Hyp |
| 251 | D | K | D | K | D | N | A | A | P | P | T | N | V | G | S | N | G | Hyp |

TABLE 7-continued

SEQUENCE LISTING

| 252 | D | K | D | K | D | N | V | A | P | A | T | N | V | G | S | N | G | Hyp |
|---|---|---|---|---|---|---|---|---|---|---|---|---|---|---|---|---|---|---|
| 253 | T | K | D | K | D | N | V | A | P | T | N | V | G | S | N | G | Hyp |  |
| 254 | D | K | D | K | D | N | V | P | P | T | — | N | V | G | S | N | G | Hyp |
| 255 | D | K | D | K | D | N | V | A | P | T | — | N | V | G | S | N | G | Hyp |
| 256 | D | K | D | K | D | Q | V | A | P | P | T | N | V | G | S | N | S | Hyp |
| 257 | D | K | D | K | D | N | V | A | P | R | T | K | V | G | S | N | G | Y |
| 258 | D | K | A | K | D | N | V | A | P | P | T | N | V | G | S | N | G | Hyp |
| 259 | D | K | D | K | D | N | V | A | P | R | T | K | V | G | P | Q | G | Hyp |
| 260 | D | K | D | K | D | N | V | A | P | R | T | N | I | G | P | Q | G | Hyp |
| 261 | D | K | D | K | D | N | V | A | P | R | T | N | V | G | P | Q | G | Hyp |
| 262 | D | K | D | K | D | N | V | A | A | P | T | N | V | G | S | N | G | Hyp |
| 263 | D | K | D | K | D | N | V | A | P | R | T | N | V | G | P | Q | G | Y |
| 264 | D | K | D | K | D | N | V | A | P | R | T | N | V | G | S | N | T | Y |
| 265 | D | K | D | K | D | N | V | A | P | P | T | N | V | G | S | N | G | Hyp |
| 266 | D | K | D | K | D | N | V | S | P | P | T | N | V | G | S | N | G | Hyp |
| 267 | D | K | D | K | D | N | V | A | P | R | T | N | V | G | P | Q | G | Hyp |
| 268 | D | K | D | K | D | N | V | A | P | P | T | N | V | G | S | N | G | Hyp |
| 269 | D | K | D | K | D | N | V | A | P | R | T | N | V | G | P | N | G | Y |
| 270 | D | K | D | K | D | N | V | A | P | R | T | N | V | G | P | N | G | Hyp |
| 271 | D | K | D | K | D | N | V | A | P | R | T | N | V | S | P | N | G | Y |
| 272 | D | K | D | K | D | N | V | A | P | R | T | E | V | G | S | N | G | Y |
| 273 | D | K | D | K | D | N | V | A | P | R | T | N | V | G | P | Q | G | Y |
| 274 | D | K | D | K | D | N | V | A | P | R | T | K | I | G | P | Q | G | Hyp |
| 275 | D | K | D | K | D | N | V | A | P | R | T | K | I | S | P | N | G | Hyp |
| 276 | D | K | D | K | D | N | V | A | P | P | T | N | V | G | S | N | G | Hyp |
| 277 | D | K | D | K | D | N | V | A | P | R | T | K | I | G | P | N | G | Hyp |
| 278 | D | K | D | K | D | N | V | A | P | R | T | N | V | S | P | Q | G | Y |
| 279 | D | K | D | K | D | N | V | A | P | R | T | K | V | G | S | Z | G | Y |
| 280 | D | K | D | K | D | N | V | A | P | R | T | N | I | G | P | Q | G | Hyp |
| 281 | D | K | D | K | D | N | V | A | P | R | S | N | V | G | P | Q | G | Hyp |
| 282 | D | K | D | G | — | A | I | A | P | R | T | K | I | G | S | O | G | Y |
| 283 | D | K | D | K | D | N | V | A | P | R | T | N | V | S | P | Q | G | Hyp |
| 284 | D | K | D | K | D | N | V | A | P | R | S | K | I | G | P | Q | G | Hyp |
| 285 | D | K | D | K | D | N | V | A | P | R | S | K | V | G | P | Q | G | Y |
| 286 | D | K | D | K | D | N | V | A | P | R | S | N | V | S | P | Q | G | Y |
| 287 | D | K | D | K | D | N | V | A | P | R | T | K | V | S | P | Q | G | Hyp |
| 288 | D | K | D | K | D | N | V | A | P | R | T | K | V | S | P | N | G | Hyp |
| 289 | D | K | D | K | D | N | V | A | P | R | S | N | V | G | P | Q | G | Hyp |
| 290 | D | K | D | K | D | N | V | A | P | R | S | K | V | G | P | N | G | Hyp |
| 291 | D | K | D | K | D | N | V | A | P | R | T | N | I | G | P | Q | G | Hyp |
| 292 | D | K | D | K | D | N | V | A | P | R | T | K | V | G | P | Q | G | Hyp |
| 293 | D | K | D | K | D | N | V | A | P | R | S | N | V | G | P | Q | G | Hyp |
| 294 | D | K | D | K | D | N | V | A | P | R | T | K | I | S | P | Q | G | Hyp |
| 295 | D | K | F | K | D | N | V | A | P | R | S | K | I | S | P | Q | T | Y |
| 296 | D | K | D | K | D | N | V | A | P | R | S | K | I | S | P | Q | T | Hyp |
| 297 | D | K | D | K | D | N | V | A | P | R | S | N | I | G | P | N | G | Hyp |
| 298 | D | K | D | K | D | N | V | A | P | R | T | K | V | G | P | Q | G | Y |
| 299 | D | K | D | K | D | N | V | A | P | R | S | K | I | G | P | N | G | Hyp |
| 300 | D | K | D | K | D | N | V | A | P | R | S | N | I | S | P | Q | G | Hyp |
| 301 | D | K | D | K | D | N | V | A | P | R | T | K | I | G | P | Q | G | Hyp |
| 302 | D | K | D | K | D | N | V | A | P | R | T | N | V | S | P | N | G | Hyp |
| 303 | D | K | D | K | D | N | V | A | P | R | S | N | I | G | P | Q | G | Hyp |
| 304 | D | K | D | K | D | N | V | A | P | R | S | N | V | S | P | N | G | Hyp |
| 305 | D | K | D | K | D | N | V | A | P | R | S | K | V | S | P | Q | G | Hyp |
| 306 | N | K | D | K | A | Q | V | S | P | P | T | E | V | G | P | N | S | Hyp |
| 307 | N | K | D | K | A | 0 | V | S | P | P | T | E | V | G | P | N | S | Hyp |
| 308 | D | K | D | K | D | N | V | A | P | P | T | N | V | G | S | N | G | Hyp |
| 309 | D | K | D | K | D | N | V | A | P | P | T | N | V | G | S | N | G | Hyp |
| 310 | D | K | D | K | A | N | V | S | P | P | T | E | V | G | P | N | S | Hyp |
| 311 | D | K | D | K | D | N | V | A | P | R | T | N | V | G | P | Q | G | Y |
| 312 | D | K | D | K | D | N | V | A | P | R | T | K | V | G | S | N | G | Hyp |
| 313 | D | K | D | K | D | N | V | A | P | P | T | N | V | G | S | N | G | Hyp |
| 314 | D | K | D | K | A | N | V | A | P | P | T | N | V | G | S | N | G | Hyp |
| 315 | D | K | D | K | D | N | A | A | P | P | T | N | V | G | S | N | G | Hyp |
| 316 | D | K | D | K | D | N | V | A | P | A | T | N | V | G | S | N | G | Hyp |
| 317 | T | K | D | K | D | N | V | A | P | P | T | N | V | G | S | N | G | Hyp |
| 318 | D | K | D | K | D | N | V | P | P | T | — | N | V | G | S | N | G | Hyp |
| 319 | D | K | D | K | D | N | V | A | P | T | — | N | V | G | S | N | G | Hyp |
| 320 | D | K | A | K | D | N | V | A | P | P | T | N | V | G | S | N | G | Hyp |
| 321 | D | K | D | K | D | N | V | A | P | P | Y | N | E | G | S | N | G | Hyp |
| 322 | D | K | D | K | D | N | V | A | P | R | T | K | V | G | P | Q | G | Hyp |
| 323 | D | K | D | K | D | N | V | A | P | R | T | N | V | G | P | Q | G | Hyp |
| 324 | D | K | D | K | D | A | V | A | P | P | T | N | V | G | S | N | G | Hyp |
| 325 | D | K | D | K | D | N | V | A | A | P | T | N | V | G | S | N | G | Hyp |
| 326 | D | K | D | K | D | N | V | A | P | R | T | N | V | G | P | Q | G | Y |
| 327 | D | K | D | K | D | N | V | A | P | R | T | N | V | G | S | N | T | Y |
| 328 | D | A | D | K | D | N | V | A | P | P | T | N | V | G | S | N | G | Hyp |
| 329 | D | K | D | K | D | N | V | A | P | P | T | N | V | G | S | N | G | Hyp |

TABLE 7-continued

SEQUENCE LISTING

| | | | | | | | | | | | | | | | | |
|---|---|---|---|---|---|---|---|---|---|---|---|---|---|---|---|---|
| 330 | D | K | D | K | D | N | V | A | P | P | T | N | V | G | S | N | G | Hyp |
| 331 | D | K | D | K | D | N | V | A | P | R | T | N | I | G | P | N | G | Hyp |
| 332 | D | K | D | K | D | N | V | A | P | R | T | N | V | G | P | N | G | Y |
| 333 | D | K | D | K | D | N | V | A | P | P | T | N | V | G | S | N | G | Hyp |
| 334 | D | K | D | K | D | N | V | A | P | R | T | E | V | G | S | N | G | Y |
| 335 | D | K | D | K | D | N | V | A | P | R | T | N | V | G | P | Q | G | Y |
| 336 | D | K | D | K | D | N | V | A | P | R | T | K | I | G | P | Q | G | Hyp |
| 337 | D | K | D | K | D | N | V | A | P | R | T | K | I | S | P | N | G | Hyp |
| 338 | D | K | D | K | D | N | V | A | P | P | T | N | V | G | S | N | G | Hyp |
| 339 | D | K | D | K | D | N | V | A | P | R | T | K | I | G | P | N | G | Hyp |
| 340 | D | K | D | K | D | N | V | A | P | R | T | N | V | S | P | Q | G | Y |
| 341 | D | K | D | K | D | N | V | A | P | R | T | N | I | G | P | Q | G | Hyp |
| 342 | D | K | D | K | D | N | V | A | P | R | S | N | V | G | P | Q | G | Hyp |
| 343 | D | K | D | K | D | N | V | A | P | R | T | K | I | G | P | N | G | Hyp |
| 344 | D | K | D | K | D | N | V | A | P | R | S | K | V | G | P | Q | G | Y |
| 345 | D | K | D | K | D | N | V | A | P | R | S | N | V | S | P | Q | G | Y |
| 346 | D | K | D | K | D | N | V | A | P | R | S | N | V | G | P | Q | G | Y |
| 347 | D | K | D | K | D | N | V | A | P | R | S | K | V | G | P | N | G | Hyp |
| 348 | D | K | D | K | D | N | V | A | P | R | T | N | I | G | P | N | G | Y |
| 349 | D | K | D | K | D | N | V | A | P | R | T | K | V | G | P | Q | G | Hyp |
| 350 | D | K | D | K | D | N | V | A | P | R | T | K | I | S | P | Q | G | Hyp |
| 351 | D | K | F | K | D | N | V | A | P | R | S | K | I | S | P | Q | T | Hyp |
| 352 | D | K | D | K | D | N | V | A | P | R | S | N | I | G | P | N | G | Hyp |
| 353 | D | K | D | K | D | N | V | A | P | R | S | K | V | G | P | Q | G | Hyp |
| 354 | D | K | D | K | D | N | V | A | P | R | T | K | V | G | P | Q | G | Y |
| 355 | D | K | D | K | D | N | V | A | P | R | S | K | I | G | P | N | G | Hyp |
| 356 | D | K | D | K | D | N | V | A | P | R | T | N | I | G | P | Q | G | Y |
| 357 | D | K | D | K | D | N | V | A | P | R | T | K | I | G | P | Q | G | Hyp |
| 358 | D | K | D | K | D | N | V | A | P | R | T | N | V | S | P | N | G | Hyp |
| 359 | D | K | D | K | D | N | V | A | P | R | S | N | I | G | P | Q | G | Hyp |
| 360 | D | K | D | K | D | N | V | A | P | R | S | N | V | S | P | N | G | Hyp |
| 361 | D | K | D | K | D | N | V | A | P | R | T | K | V | G | S | N | G | Y |
| 362 | D | K | D | K | D | N | V | A | P | R | T | N | V | G | P | Q | G | Y |
| 363 | D | K | D | K | D | N | V | A | P | R | S | K | I | G | P | Q | G | Y |
| 364 | D | K | D | K | D | N | V | A | P | R | T | N | I | G | P | Q | G | Y |
| 365 | D | K | D | K | D | N | V | A | P | R | T | K | I | G | P | Q | G | Y |
| 366 | D | K | D | K | D | N | V | A | P | R | T | N | I | S | P | N | G | Y |
| 367 | D | K | D | K | D | N | V | A | P | R | T | K | I | G | P | N | G | Y |
| 368 | D | K | D | K | D | N | V | A | P | R | T | K | V | G | P | Q | G | Y |
| 369 | D | K | D | K | D | N | V | A | P | R | T | K | V | G | P | Q | G | Y |
| 370 | D | K | D | K | D | N | V | A | P | R | T | E | V | G | S | N | G | Y |
| 371 | D | K | D | K | D | N | V | A | P | R | T | K | I | S | P | N | G | Y |
| 372 | D | K | D | K | D | N | V | A | P | R | T | N | V | G | P | Q | G | Y |
| 373 | D | K | D | K | D | N | V | A | P | R | S | N | V | G | P | N | G | Y |
| 374 | D | K | D | K | D | N | V | A | P | R | S | N | V | G | P | Q | G | Y |
| 375 | D | K | D | K | D | N | V | A | P | R | S | K | V | G | P | Q | G | Y |
| 376 | D | K | D | K | D | N | V | A | P | R | T | K | I | G | S | N | G | Y |
| 377 | D | K | D | K | D | N | V | A | P | R | T | K | V | G | P | Q | G | Y |
| 278 | D | K | D | K | D | N | V | A | P | R | T | K | V | G | S | N | G | Y |
| 379 | D | K | D | K | D | N | V | A | P | R | T | N | I | G | P | Q | G | Y |
| 380 | D | K | D | K | D | N | V | A | P | R | T | K | V | G | P | Q | G | Y |
| 381 | D | K | D | K | D | N | V | A | P | R | T | N | I | G | P | N | G | Y |
| 382 | D | K | D | K | D | N | V | A | P | R | S | N | I | G | P | Q | G | Y |
| 383 | D | K | D | K | D | N | V | A | P | R | S | N | I | S | P | N | G | Y |
| 384 | D | K | D | K | D | N | V | A | P | R | S | K | V | S | P | N | G | Y |
| 385 | D | K | D | K | D | N | V | A | P | R | T | K | V | S | P | N | G | Y |
| 386 | D | K | D | K | D | N | V | A | P | R | T | N | V | G | P | Q | G | Y |
| 387 | D | K | D | K | D | N | V | A | P | R | S | K | I | G | P | Q | G | Y |
| 388 | D | K | D | K | D | N | V | A | P | R | T | N | I | G | P | Q | G | Y |
| 389 | D | K | D | K | D | N | V | A | P | R | S | K | I | G | P | Q | G | Y |
| 390 | D | K | D | K | D | N | V | A | P | R | T | K | I | G | P | Q | G | Y |
| 391 | D | K | D | K | D | N | V | A | P | R | T | K | I | G | P | Q | G | Y |
| 392 | D | K | D | K | D | N | V | A | P | R | T | K | V | G | P | Q | G | Y |

The invention claimed is:

1. An $hAM_{15-52}$ analogue or a pharmaceutically acceptable salt thereof comprising 38 amino acids ($X_1$-$X_{38}$) with an $hAMY3R\text{-}EC_{50} \leq 250$ μM and an $hAM1R\text{-}EC_{50} \geq 25$ nM, wherein the amino acid in position $X_4$ is selected as F, Y, W, T, M, I, A, or C; $X_{37}$ is selected as G, Y, S, W, T, Q, P, M, I, H, F, E, A, R, C, or K; $X_{38}$ is selected as Hyp, Y, W, T, Q, P, M, I, H, F, E, A, R, or K; $X_{11}$ is R, W, or Cit and wherein at least one of the positions $X_4$, $X_{37}$ or $X_{38}$ is not the amino acid present in $hAM_{15-52}$ (SEQ ID NO: 1) in said position and further wherein the $hAM_{15-52}$ analogue has at least 50% identity to $hAM_{15-52}$ (SEQ ID NO: 1).

2. An $hAM_{15-52}$ analogue or a pharmaceutically acceptable salt thereof according to claim 1, wherein the $hAM_{15-52}$ analogue has at least 60% identity to $hAM_{15-52}$ (SEQ ID NO: 1).

3. An $hAM_{15-52}$ analogue according to claim 1, wherein at least two of the positions $X_4$, $X_{37}$, and $X_{38}$ is not the amino acid present in $hAM_{15-52}$ (SEQ ID NO: 1) in said position.

4. An $hAM_{15-52}$ analogue according to claim 1, wherein $X_4$ is selected as F, W, M, I, or C.

5. An $hAM_{15-52}$ analogue thereof according to claim 1, wherein $X_{37}$ is selected as G, Y, W, P, H, or F.

6. An $hAM_{15-52}$ analogue according to claim 1, wherein $X_{38}$ is selected as Hyp, Y, W, M, or F.

7. An $hAM_{15-52}$ analogue according to claim 1, wherein $X_{17}$ is selected as W, or H.

8. An $hAM_{15-52}$ analogue according to claim 1, wherein $X_{11}$ is R.

9. An $hAM_{15-52}$ analogue or a pharmaceutically acceptable salt thereof according to claim 1, wherein the $hAM_{15-52}$ analogue has at least 70% identity to $hAM_{15-52}$ (SEQ ID NO: 1).

10. An $hAM_{15-52}$ analogue or a pharmaceutically acceptable salt thereof according to claim 1, wherein the $hAM_{15-52}$ analogue has at least 80% identity to $hAM_{15-52}$ (SEQ ID NO: 1).

* * * * *

SEQUENCE LISTING

<160> NUMBER OF SEQ ID NOS: 411

<210> SEQ ID NO 1
<211> LENGTH: 38
<212> TYPE: PRT
<213> ORGANISM: Artificial Sequence
<220> FEATURE:

<223> OTHER INFORMATION: Designed polypeptide

<400> SEQUENCE: 1

Gly Cys Arg Phe Gly Thr Cys Thr Val Gln Lys Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 2
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: DISULFID
<222> LOCATION: (2)..(7)
<223> OTHER INFORMATION: Disulphide bridge

<400> SEQUENCE: 2

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 3
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 3

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Xaa
        35

<210> SEQ ID NO 4
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 4

Lys Cys Asn Thr Ala Thr Cys Thr Val Asp Arg Leu Ala His Gln Ile
1               5                   10                  15

Tyr Gln Phe Thr Asp Lys Asp Lys Asp Asn Val Ala Pro Pro Thr Asn
            20                  25                  30

```
<210> SEQ ID NO 5
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 5

Lys Cys Asn Thr Ala Thr Cys Thr Val Gln Arg Leu Ala Asp Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 6
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 6

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Lys Gly Xaa
        35

<210> SEQ ID NO 7
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 7

Lys Cys Asn Thr Ala Thr Cys Thr Val Gln Arg Leu Ala Ala Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 8
<211> LENGTH: 38
<212> TYPE: PRT
<213> ORGANISM: Artificial Sequence
<220> FEATURE:
<223> OTHER INFORMATION: Designed polypeptide
```

```
<220> FEATURE:
<221> NAME/KEY: MOD_RES
<222> LOCATION: (38)..(38)
<223> OTHER INFORMATION: 4Hyp

<400> SEQUENCE: 8

Lys Cys Asn Thr Ser Thr Cys Thr Val Ala Arg Leu Ala Asp Gln Ile
1               5                   10                  15

Thr Gln Phe Ser Asn Lys Asp Lys Ala Gln Val Ser Pro Pro Thr Glu
            20                  25                  30

Val Gly Pro Asn Ser Xaa
            35

<210> SEQ ID NO 9
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 9

Arg Cys Asn Ala Ser Thr Cys Thr Val Asn Arg Leu Ala Asp Gln Ile
1               5                   10                  15

Thr Gln Phe Ser Asn Lys Asp Lys Ala Gln Val Ser Pro Pro Thr Glu
            20                  25                  30

Val Gly Pro Asn Ser Xaa
            35

<210> SEQ ID NO 10
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 10

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Glu
            20                  25                  30

Val Gly Ser Asn Gly Xaa
            35

<210> SEQ ID NO 11
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 11

Lys Cys Asn Thr Ala Thr Cys Thr Val Gln Arg Leu Ala His Gln Ile
1               5                   10                  15
```

Asn Gln Phe Thr Asp Lys Asp Lys Asp Asn Val Ala Pro Pro Thr Asn
            20                  25                  30

Val Gly Ser Asn Gly Xaa
        35

<210> SEQ ID NO 12
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 12

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Lys Ala Pro Pro Thr Asn
            20                  25                  30

Val Gly Ser Asn Gly Xaa
        35

<210> SEQ ID NO 13
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 13

Lys Cys Asn Thr Ala Thr Cys Thr Val Gln Arg Leu Ala His Ala Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 14
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 14

Lys Cys Asn Thr Ala Thr Cys Thr Val Gln Arg Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 15
<211> LENGTH: 38
<212> TYPE: PRT

```
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 15

Lys Cys Asn Thr Ser Thr Cys Thr Val Ala Arg Leu Ala Asp Gln Ile
1               5                   10                  15

Thr Gln Phe Ser Asp Lys Asp Lys Ala Asn Val Ser Pro Pro Thr Glu
            20                  25                  30

Val Gly Pro Asn Ser Xaa
            35

<210> SEQ ID NO 16
<211> LENGTH: 38
<212> TYPE: PRT
<213> ORGANISM: Artificial Sequence
<220> FEATURE:
<223> OTHER INFORMATION: Designed polypeptide

<400> SEQUENCE: 16

Gly Cys Arg Phe Gly Thr Cys Thr Val Gln Arg Leu Ala Asn Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 17
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 17

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Glu
            20                  25                  30

Val Gly Ser Asn Gly Xaa
            35

<210> SEQ ID NO 18
<211> LENGTH: 38
<212> TYPE: PRT
<213> ORGANISM: Artificial Sequence
<220> FEATURE:
<223> OTHER INFORMATION: Designed polypeptide

<400> SEQUENCE: 18

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Glu
            20                  25                  30

Val Gly Ser Asn Gly Pro
            35
```

<210> SEQ ID NO 19
<211> LENGTH: 37
<212> TYPE: PRT
<213> ORGANISM: Artificial Sequence
<220> FEATURE:
<223> OTHER INFORMATION: Designed polypeptide

<400> SEQUENCE: 19

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Arg Thr Lys Val
            20                  25                  30

Gly Ser Asn Gly Tyr
        35

<210> SEQ ID NO 20
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 20

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Xaa
        35

<210> SEQ ID NO 21
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 21

Lys Cys Asn Thr Ala Thr Cys Thr Val Gln Arg Leu Ala Asn Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 22
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp -continued

```
<400> SEQUENCE: 22

Lys Cys Asn Thr Ala Thr Cys Thr Val Gln Arg Leu Ala His Gln Ile
1               5                   10                  15

Thr Gln Phe Thr Asp Lys Asp Lys Asp Asn Val Ala Pro Pro Thr Asn
            20                  25                  30

Val Gly Ser Asn Gly Xaa
        35

<210> SEQ ID NO 23
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 23

Lys Cys Asn Thr Ala Thr Cys Thr Val Gln Arg Leu Ala His Gln Ile
1               5                   10                  15

Tyr Gln Phe Ala Asp Lys Asp Lys Asp Asn Val Ala Pro Pro Thr Asn
            20                  25                  30

Val Gly Ser Asn Gly Xaa
        35

<210> SEQ ID NO 24
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 24

Lys Cys Asn Thr Ala Thr Cys Thr Val Gln Arg Leu Ala His Gln Ile
1               5                   10                  15

Tyr Gln Phe Thr Ala Lys Asp Lys Asp Asn Val Ala Pro Pro Thr Asn
            20                  25                  30

Val Gly Ser Asn Gly Xaa
        35

<210> SEQ ID NO 25
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 25

Lys Cys Asn Thr Ala Thr Cys Thr Val Gln Arg Leu Ala His Gln Ile
1               5                   10                  15
```

```
Tyr Gln Phe Thr Asp Lys Asp Ala Asp Asn Val Ala Pro Pro Thr Asn
            20                  25                  30

Val Gly Ser Asn Gly Xaa
        35

<210> SEQ ID NO 26
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 26

Lys Cys Asn Thr Ala Thr Cys Thr Val Gln Arg Leu Ala His Gln Ile
1               5                   10                  15

Tyr Gln Phe Thr Asp Lys Asp Lys Ala Asn Val Ala Pro Pro Thr Asn
            20                  25                  30

Val Gly Ser Asn Gly Xaa
        35

<210> SEQ ID NO 27
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 27

Lys Cys Asn Thr Ala Thr Cys Thr Val Gln Arg Leu Ala His Gln Ile
1               5                   10                  15

Tyr Gln Phe Thr Asp Lys Asp Lys Asp Asn Ala Ala Pro Pro Thr Asn
            20                  25                  30

Val Gly Ser Asn Gly Xaa
        35

<210> SEQ ID NO 28
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 28

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Ala Thr Asn
            20                  25                  30

Val Gly Ser Asn Gly Xaa
        35

<210> SEQ ID NO 29
<211> LENGTH: 37
```

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 29

Lys Cys Asn Thr Ala Thr Cys Thr Val Gln Arg Leu Ala His Gln Ile
1               5                   10                  15

Tyr Gln Phe Thr Lys Asp Lys Asp Asn Val Ala Pro Pro Thr Asn Val
            20                  25                  30

Gly Ser Asn Gly Xaa
            35

<210> SEQ ID NO 30
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 30

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Pro Pro Thr Asn Val
            20                  25                  30

Gly Ser Asn Gly Xaa
            35

<210> SEQ ID NO 31
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 31

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Thr Asn Val
            20                  25                  30

Gly Ser Asn Gly Xaa
            35

<210> SEQ ID NO 32
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

<400> SEQUENCE: 32

Arg Cys Gln Thr Ser Thr Cys Thr Val Ala Arg Leu Ala Glu Gln Ile
1               5                   10                  15

Ala Gln Tyr Thr Asp Lys Asp Lys Asp Gln Val Ala Pro Pro Thr Asn
            20                  25                  30

Val Gly Ser Asn Ser Xaa
            35

<210> SEQ ID NO 33
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 33

Arg Cys Gln Ala Ser Thr Cys Thr Val Ala Xaa Leu Ala Glu Gln Ile
1               5                   10                  15

Ala Gln Tyr Thr Asp Lys Asp Lys Asp Gln Val Ala Pro Pro Thr Glu
            20                  25                  30

Val Gly Pro Asn Ser Xaa
            35

<210> SEQ ID NO 34
<211> LENGTH: 38
<212> TYPE: PRT
<213> ORGANISM: Artificial Sequence
<220> FEATURE:
<223> OTHER INFORMATION: Designed polypeptide

<400> SEQUENCE: 34

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Tyr
            35

<210> SEQ ID NO 35
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 35

Lys Cys Asn Thr Ala Thr Cys Thr Val Gln Arg Leu Ala His Gln Ile
1               5                   10                  15

Gln Gln Phe Thr Asp Lys Asp Lys Asp Asn Val Ala Pro Pro Thr Asn
            20                  25                  30

Val Gly Ser Asn Gly Xaa
        35

<210> SEQ ID NO 36
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 36

Lys Cys Lys Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 37
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 37

Lys Cys Asn Thr Ala Thr Cys Thr Val Ala Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 38
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 38

Lys Cys Asn Thr Ala Thr Cys Thr Val Asn Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 39
<211> LENGTH: 38

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 39

Arg Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 40
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 40

Lys Cys Asn Thr Ala Thr Cys Thr Val Gln Arg Leu Ala Glu Gln Ile
1               5                   10                  15

Tyr Gln Phe Thr Asp Lys Asp Lys Lys Asn Val Ala Pro Pro Thr Asn
            20                  25                  30

Val Gly Ser Asn Gly Xaa
            35

<210> SEQ ID NO 41
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 41

Lys Cys Asn Thr Ala Thr Cys Thr Val Gln Arg Leu Ala Glu Gln Ile
1               5                   10                  15

Tyr Gln Phe Thr Asp Lys Asp Lys Asp Lys Val Ala Pro Pro Thr Asn
            20                  25                  30

Val Gly Ser Asn Gly Xaa
            35

<210> SEQ ID NO 42
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

```
<400> SEQUENCE: 42

Lys Cys Asn Thr Ala Thr Cys Thr Val Gln Arg Leu Ala His Gln Ile
1               5                   10                  15

Tyr Ala Phe Thr Asp Lys Asp Lys Asp Asn Val Ala Pro Pro Thr Asn
            20                  25                  30

Val Gly Ser Asn Gly Xaa
            35

<210> SEQ ID NO 43
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 43

Lys Cys Asn Thr Ala Thr Cys Thr Val Gln Arg Leu Ala His Gln Ile
1               5                   10                  15

Tyr Gln Phe Thr Asp Lys Ala Lys Asp Asn Val Ala Pro Pro Thr Asn
            20                  25                  30

Val Gly Ser Asn Gly Xaa
            35

<210> SEQ ID NO 44
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 44

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Tyr Asn
            20                  25                  30

Glu Gly Ser Asn Gly Xaa
            35

<210> SEQ ID NO 45
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 45

Gly Cys Arg Phe Gly Thr Cys Thr Val Gln Arg Leu Ala His Gln Ile
1               5                   10                  15
```

Tyr Gln Phe Thr Asp Lys Asp Lys Asp Asn Val Ala Pro Arg Thr Lys
            20                  25                  30

Val Gly Pro Gln Gly Xaa
        35

<210> SEQ ID NO 46
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 46

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Gln Gly Xaa
        35

<210> SEQ ID NO 47
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 47

Lys Cys Asn Thr Ala Thr Cys Thr Val Gln Arg Leu Ala Tyr Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 48
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 48

Lys Cys Asn Thr Ala Thr Cys Thr Val Gln Arg Leu Ala His Gln Ile
1               5                   10                  15

Tyr Gln Tyr Thr Asp Lys Asp Lys Asp Asn Val Ala Pro Pro Thr Asn
            20                  25                  30

Val Gly Ser Asn Gly Xaa
        35

<210> SEQ ID NO 49
<211> LENGTH: 38

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 49

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Xaa
        35

<210> SEQ ID NO 50
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 50

Lys Cys Asn Thr Ser Thr Cys Thr Val Gln Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 51
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 51

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 52
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

<400> SEQUENCE: 52

Lys Cys Asn Thr Ala Thr Cys Thr Val Gln Arg Leu Ala His Gln Ile
1               5                   10                  15

Tyr Gln Phe Thr Asp Lys Asp Lys Asp Ala Val Ala Pro Pro Thr Asn
            20                  25                  30

Val Gly Ser Asn Gly Xaa
            35

<210> SEQ ID NO 53
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 53

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Ala Pro Thr Asn
            20                  25                  30

Val Gly Ser Asn Gly Xaa
            35

<210> SEQ ID NO 54
<211> LENGTH: 38
<212> TYPE: PRT
<213> ORGANISM: Artificial Sequence
<220> FEATURE:
<223> OTHER INFORMATION: Designed polypeptide

<400> SEQUENCE: 54

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 55
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 55

Lys Cys Asn Thr Ala Thr Cys Thr Val Glu Arg Leu Ala His Gln Ile
1               5                   10                  15

Tyr Gln Phe Thr Asp Lys Asp Lys Asp Asn Val Ala Ala Pro Thr Asn
            20                  25                  30

Val Gly Ser Asn Gly Xaa
            35

<210> SEQ ID NO 56

```
<211> LENGTH: 38
<212> TYPE: PRT
<213> ORGANISM: Artificial Sequence
<220> FEATURE:
<223> OTHER INFORMATION: Designed polypeptide

<400> SEQUENCE: 56

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Asn
            20                  25                  30

Val Gly Ser Asn Thr Tyr
            35

<210> SEQ ID NO 57
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 57

Lys Cys Asn Thr Ala Thr Cys Thr Val Gln Arg Leu Ala His Gln Ile
1               5                   10                  15

Tyr Gln Phe Ser Asp Lys Asp Lys Asp Asn Val Ala Pro Pro Thr Asn
            20                  25                  30

Val Gly Ser Asn Gly Xaa
            35

<210> SEQ ID NO 58
<211> LENGTH: 37
<212> TYPE: PRT
<213> ORGANISM: Artificial Sequence
<220> FEATURE:
<223> OTHER INFORMATION: Designed polypeptide

<400> SEQUENCE: 58

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Lys Val
            20                  25                  30

Gly Ser Asn Thr Tyr
            35

<210> SEQ ID NO 59
<211> LENGTH: 37
<212> TYPE: PRT
<213> ORGANISM: Artificial Sequence
<220> FEATURE:
<223> OTHER INFORMATION: Designed polypeptide

<400> SEQUENCE: 59

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Lys Val
            20                  25                  30

Gly Ser Asn Gly Tyr
            35
```

```
<210> SEQ ID NO 60
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 60

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Lys
            20                  25                  30

Val Gly Ser Asn Gly Xaa
        35

<210> SEQ ID NO 61
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 61

Lys Cys Asn Thr Ala Thr Cys Thr Val Gln Arg Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 62
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 62

Lys Cys Asn Thr Ser Thr Cys Thr Val Gln Arg Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 63
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

<400> SEQUENCE: 63

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Ala
            20                  25                  30

Val Gly Ser Asn Gly Xaa
        35

<210> SEQ ID NO 64
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 64

Lys Cys Asn Thr Ala Thr Cys Thr Val Gln Arg Leu Ala His Gln Ile
1               5                   10                  15

Tyr Gln Phe Thr Asp Ala Asp Lys Asp Asn Val Ala Pro Pro Thr Asn
            20                  25                  30

Val Gly Ser Asn Gly Xaa
        35

<210> SEQ ID NO 65
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 65

Lys Cys Asn Thr Ala Thr Cys Thr Val Gln Arg Leu Ala His Gln Ile
1               5                   10                  15

Tyr Gln Phe Asp Lys Asp Lys Asp Asn Val Ala Pro Pro Thr Asn Val
            20                  25                  30

Gly Ser Asn Gly Xaa
        35

<210> SEQ ID NO 66
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 66

Lys Cys Asn Thr Ala Thr Cys Thr Val Gln Arg Leu Ala Glu Gln Ile
1               5                   10                  15

```
Tyr Gln Phe Thr Asp Lys Asp Lys Asp Asn Val Ser Pro Pro Thr Asn
            20                  25                  30

Val Gly Ser Asn Gly Xaa
        35

<210> SEQ ID NO 67
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 67

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Glu
            20                  25                  30

Val Gly Ser Asn Gly Xaa
        35

<210> SEQ ID NO 68
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 68

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Glu
            20                  25                  30

Val Gly Ser Asn Gly Xaa
        35

<210> SEQ ID NO 69
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 69

Lys Cys Asn Thr Ala Thr Cys Thr Val Gln Arg Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Ser Xaa
        35

<210> SEQ ID NO 70
<211> LENGTH: 38
```

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 70

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Xaa
        35

<210> SEQ ID NO 71
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 71

Lys Cys Asn Thr Ala Thr Cys Thr Val Gln Arg Leu Ala His Gln Ile
1               5                   10                  15

Ala Gln Tyr Thr Asp Lys Asp Lys Asp Asn Val Ala Pro Pro Thr Asn
            20                  25                  30

Val Gly Ser Asn Gly Xaa
        35

<210> SEQ ID NO 72
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 72

Lys Cys Gln Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 73
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

<400> SEQUENCE: 73

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Gln
            20                  25                  30

Val Gly Ser Asn Gly Xaa
            35

<210> SEQ ID NO 74
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 74

Lys Cys Asn Thr Ala Thr Cys Thr Val Gln Arg Leu Ala Lys Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 75
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 75

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 76
<211> LENGTH: 35
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES

```
<222> LOCATION: (35)..(35)
<223> OTHER INFORMATION: 4Hyp

<400> SEQUENCE: 76

Arg Cys Gly Thr Ala Thr Cys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 77
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 77

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 78
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 78

Lys Cys Asn Thr Ala Thr Cys Thr Val Gln Arg Leu Ala Glu Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 79
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 79

Lys Cys Asn Thr Ala Thr Cys Thr Val Gln Arg Leu Ala His Gln Ile
1               5                   10                  15

Ala Gln Phe Ser Asp Lys Asp Lys Asp Asn Val Ala Pro Pro Thr Asn
            20                  25                  30
```

```
Val Gly Ser Asn Gly Xaa
            35

<210> SEQ ID NO 80
<211> LENGTH: 35
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 80

Arg Cys Gln Thr Ala Thr Cys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 81
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 81

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Asn Gly Xaa
            35

<210> SEQ ID NO 82
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 82

Lys Cys Asn Thr Ala Thr Cys Thr Val Gln Arg Leu Ala His Gln Ile
1               5                   10                  15
```

Tyr Gln Phe Thr Asn Lys Asp Lys Asp Asn Val Ala Pro Pro Thr Asn
            20                  25                  30

Val Gly Ser Asn Gly Xaa
        35

<210> SEQ ID NO 83
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 83

Lys Cys Asn Thr Ala Thr Cys Thr Val Gln Arg Leu Ala His Gln Ile
1               5                   10                  15

Tyr Gln Phe Ala Asp Lys Asp Lys Asp Asn Val Ala Pro Pro Thr Asn
            20                  25                  30

Val Gly Ser Asn Gly Xaa
        35

<210> SEQ ID NO 84
<211> LENGTH: 38
<212> TYPE: PRT
<213> ORGANISM: Artificial Sequence
<220> FEATURE:
<223> OTHER INFORMATION: Designed polypeptide

<400> SEQUENCE: 84

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Asn Gly Tyr
        35

<210> SEQ ID NO 85
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 85

Lys Cys Asn Thr Ala Thr Cys Thr Val Gln Arg Leu Ala His Gln Ile
1               5                   10                  15

Val Gln Phe Thr Asp Lys Asp Lys Asp Asn Val Ala Pro Pro Thr Asn
            20                  25                  30

Val Gly Ser Asn Gly Xaa
        35

<210> SEQ ID NO 86
<211> LENGTH: 38
<212> TYPE: PRT
<213> ORGANISM: Artificial Sequence
<220> FEATURE:
<223> OTHER INFORMATION: Designed polypeptide

```
<220> FEATURE:
<221> NAME/KEY: MOD_RES
<222> LOCATION: (38)..(38)
<223> OTHER INFORMATION: 4Hyp

<400> SEQUENCE: 86

Lys Cys Asn Thr Ala Thr Cys Thr Val Ala Arg Leu Ala His Gln Ile
1               5                   10                  15

Asn Gln Phe Thr Asp Lys Asp Lys Asp Asn Val Ala Pro Pro Thr Asn
            20                  25                  30

Val Gly Ser Asn Gly Xaa
            35

<210> SEQ ID NO 87
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 87

Lys Cys Asn Thr Ala Thr Cys Thr Val Gln Arg Leu Ala His Gln Ile
1               5                   10                  15

Ala Gln Phe Thr Asp Lys Asn Lys Asp Asn Val Ala Pro Pro Thr Asn
            20                  25                  30

Val Gly Ser Asn Gly Xaa
            35

<210> SEQ ID NO 88
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 88

Lys Cys Asn Thr Ser Thr Cys Thr Val Gln Arg Leu Ala His Gln Ile
1               5                   10                  15

Ala Gln Phe Thr Asp Lys Asp Lys Asp Pro Val Ala Pro Pro Thr Asn
            20                  25                  30

Val Gly Ser Asn Gly Xaa
            35

<210> SEQ ID NO 89
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 89

Lys Cys Asn Thr Ala Thr Cys Thr Val Gln Arg Leu Ala Glu Gln Ile
1               5                   10                  15
```

Tyr Gln Phe Lys Asp Lys Asp Lys Asp Asn Val Ala Pro Pro Thr Asn
            20                  25                  30

Val Gly Ser Asn Gly Xaa
            35

<210> SEQ ID NO 90
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 90

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Asn Gly Xaa
            35

<210> SEQ ID NO 91
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 91

Lys Cys Asn Thr Ala Thr Cys Thr Val Gln Arg Leu Ala His Gln Ile
1               5                   10                  15

Tyr Gln Phe Thr Asp Lys Asn Lys Asp Asn Val Ala Pro Pro Thr Asn
            20                  25                  30

Val Gly Ser Asn Gly Xaa
            35

<210> SEQ ID NO 92
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 92

Lys Cys Asn Thr Ala Thr Cys Thr Val Gln Arg Leu Ala His Gln Ile
1               5                   10                  15

Ala Gln Phe Thr Asp Lys Asp Lys Asp Pro Val Ala Pro Pro Thr Asn
            20                  25                  30

Val Gly Ser Asn Gly Xaa
            35

<210> SEQ ID NO 93
<211> LENGTH: 37
<212> TYPE: PRT

<213> ORGANISM: Artificial Sequence
<220> FEATURE:
<223> OTHER INFORMATION: Designed polypeptide

<400> SEQUENCE: 93

Lys Cys Asn Thr Ala Thr Cys Ala Thr Gln Arg Leu Ala Asn Phe Leu
1               5                   10                  15

Val His Ser Ser Asn Asn Phe Gly Ala Ile Ala Pro Ser Thr Lys Val
            20                  25                  30

Gly Ser Asn Gly Tyr
        35

<210> SEQ ID NO 94
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 94

Lys Cys Asn Thr Ala Thr Cys Thr Val Gln Arg Leu Ala His Gln Ile
1               5                   10                  15

Ala Gln Phe Tyr Asp Lys Asp Lys Asp Asn Val Ala Pro Pro Thr Asn
            20                  25                  30

Val Gly Ser Asn Gly Xaa
        35

<210> SEQ ID NO 95
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 95

Lys Cys Asn Thr Ala Thr Cys Thr Val Gln Arg Leu Ala His Gln Ile
1               5                   10                  15

Ala Gln Phe Thr Asn Lys Asp Lys Asp Asn Val Ala Pro Pro Thr Asn
            20                  25                  30

Val Gly Ser Asn Gly Xaa
        35

<210> SEQ ID NO 96
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 96

Lys Cys Asn Thr Ala Thr Cys Thr Val Gln Arg Leu Ala Glu Gln Ile
1               5                   10                  15

```
Tyr Gln Phe Thr Asp Lys Asp Lys Asp Asn Val Ala Pro Pro Thr Asn
            20                  25                  30

Val Gly Ser Asn Thr Xaa
        35

<210> SEQ ID NO 97
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 97

Lys Cys Ala Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 98
<211> LENGTH: 38
<212> TYPE: PRT
<213> ORGANISM: Artificial Sequence
<220> FEATURE:
<223> OTHER INFORMATION: Designed polypeptide

<400> SEQUENCE: 98

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Asn Gly Tyr
        35

<210> SEQ ID NO 99
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 99

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Xaa
        35

<210> SEQ ID NO 100
<211> LENGTH: 38
<212> TYPE: PRT
<213> ORGANISM: Artificial Sequence
<220> FEATURE:
<223> OTHER INFORMATION: Designed polypeptide
```

```
<220> FEATURE:
<221> NAME/KEY: MOD_RES
<222> LOCATION: (38)..(38)
<223> OTHER INFORMATION: 4Hyp

<400> SEQUENCE: 100

Lys Cys Asn Thr Ala Thr Cys Thr Val Gln Arg Leu Ala Glu Gln Ile
1               5                   10                  15

Tyr Gln Phe Thr Asp Lys Asp Lys Asp Gln Val Ala Pro Pro Thr Asn
            20                  25                  30

Val Gly Ser Asn Gly Xaa
            35

<210> SEQ ID NO 101
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 101

Lys Cys Asn Ala Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 102
<211> LENGTH: 38
<212> TYPE: PRT
<213> ORGANISM: Artificial Sequence
<220> FEATURE:
<223> OTHER INFORMATION: Designed polypeptide

<400> SEQUENCE: 102

Lys Cys Asn Thr Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Glu
            20                  25                  30

Val Gly Ser Asn Gly Tyr
            35

<210> SEQ ID NO 103
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 103

Lys Cys Asn Thr Ala Thr Cys Thr Val Val Arg Leu Ala His Gln Ile
1               5                   10                  15
```

-continued

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 104
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 104

Lys Cys Asn Thr Ala Thr Cys Thr Val Gln Arg Leu Ala His Gln Ile
1               5                   10                  15

Tyr Gln Phe Tyr Asp Lys Asp Lys Asp Asn Val Ala Pro Pro Thr Asn
            20                  25                  30

Val Gly Ser Asn Gly Xaa
        35

<210> SEQ ID NO 105
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 105

Lys Cys Asn Thr Ala Thr Cys Thr Val Gln Arg Leu Ala His Gln Ile
1               5                   10                  15

Ala Gln Phe Ala Asp Lys Asp Lys Asp Asn Val Ala Pro Pro Thr Asn
            20                  25                  30

Val Gly Ser Asn Gly Xaa
        35

<210> SEQ ID NO 106
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 106

Lys Cys Asn Thr Ala Thr Cys Thr Val Gln Arg Leu Ala Glu Gln Ile
1               5                   10                  15

Tyr Gln Phe Thr Ala Lys Asp Lys Asp Asn Val Ala Pro Pro Thr Asn
            20                  25                  30

Val Gly Ser Asn Gly Xaa
        35

<210> SEQ ID NO 107
<211> LENGTH: 38

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 107

Lys Cys Asn Thr Ala Thr Cys Thr Val Ala Arg Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 108
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 108

Lys Cys Asn Thr Ala Thr Cys Thr Val Gln Arg Leu Ala Glu Gln Ile
1               5                   10                  15

Tyr Gln Phe Thr Asp Lys Asp Lys Ala Asn Val Ala Pro Pro Thr Asn
            20                  25                  30

Val Gly Ser Asn Gly Xaa
        35

<210> SEQ ID NO 109
<211> LENGTH: 38
<212> TYPE: PRT
<213> ORGANISM: Artificial Sequence
<220> FEATURE:
<223> OTHER INFORMATION: Designed polypeptide

<400> SEQUENCE: 109

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Tyr
        35

<210> SEQ ID NO 110
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 110

Lys Cys Asn Thr Ala Thr Cys Thr Val Gln Arg Leu Ala His Gln Ile
1               5                   10                  15
```

Glu Gln Phe Thr Asp Lys Asp Lys Asp Asn Val Ala Pro Pro Thr Asn
            20                  25                  30

Val Gly Ser Asn Gly Xaa
        35

<210> SEQ ID NO 111
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 111

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Xaa
        35

<210> SEQ ID NO 112
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 112

Lys Cys Asn Thr Ala Thr Cys Thr Val Asp Arg Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 113
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 113

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Asn Gly Xaa
        35

<210> SEQ ID NO 114
<211> LENGTH: 38
<212> TYPE: PRT

```
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 114

Lys Cys Asn Thr Ala Thr Cys Thr Val Gln Arg Leu Ala His Gln Ile
1               5                   10                  15

Tyr Gln Ala Thr Asp Lys Asp Lys Asp Asn Val Ala Pro Pro Thr Asn
            20                  25                  30

Val Gly Ser Asn Gly Xaa
            35

<210> SEQ ID NO 115
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 115

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Asn Gly Xaa
            35

<210> SEQ ID NO 116
<211> LENGTH: 38
<212> TYPE: PRT
<213> ORGANISM: Artificial Sequence
<220> FEATURE:
<223> OTHER INFORMATION: Designed polypeptide

<400> SEQUENCE: 116

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Gln Gly Tyr
            35

<210> SEQ ID NO 117
<211> LENGTH: 38
<212> TYPE: PRT
<213> ORGANISM: Artificial Sequence
<220> FEATURE:
<223> OTHER INFORMATION: Designed polypeptide

<400> SEQUENCE: 117

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Val Gly Ser Asn Gly Tyr
            35
```

<210> SEQ ID NO 118
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 118

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Gln Gly Xaa
        35

<210> SEQ ID NO 119
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (38)..(38)
<223> OTHER INFORMATION: 4Hyp

<400> SEQUENCE: 119

Lys Cys Asn Thr Xaa Thr Cys Thr Val Gln Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 120
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 120

Lys Cys Asn Thr Ala Thr Cys Thr Val Gln Arg Leu Ala His Gln Ile
1               5                   10                  15

Ala Gln Phe Thr Asp Lys Asp Lys Asp Pro Val Ala Pro Pro Thr Asn
            20                  25                  30

Val Gly Ser Asn Ser Xaa
        35

<210> SEQ ID NO 121
<211> LENGTH: 38
<212> TYPE: PRT
<213> ORGANISM: Artificial Sequence

```
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 121

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Xaa
        35

<210> SEQ ID NO 122
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 122

Lys Cys Asn Thr Ala Thr Cys Thr Val Gln Arg Leu Ala Glu Gln Ile
1               5                   10                  15

Tyr Gln Phe Thr Asp Lys Ala Lys Asp Asn Val Ala Pro Pro Thr Asn
            20                  25                  30

Val Gly Ser Asn Gly Xaa
        35

<210> SEQ ID NO 123
<211> LENGTH: 37
<212> TYPE: PRT
<213> ORGANISM: Artificial Sequence
<220> FEATURE:
<223> OTHER INFORMATION: Designed polypeptide

<400> SEQUENCE: 123

Gly Cys Arg Phe Gly Thr Cys Thr Val Gln Arg Leu Ala His Phe Leu
1               5                   10                  15

Tyr Gln Phe Thr Asp Lys Asp Gly Ala Ile Ala Pro Arg Thr Lys Ile
            20                  25                  30

Gly Ser Gln Gly Tyr
        35

<210> SEQ ID NO 124
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 124

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30
```

Ile Gly Pro Asn Gly Xaa
        35

<210> SEQ ID NO 125
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 125

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
                20                  25                  30

Val Ser Pro Gln Gly Xaa
        35

<210> SEQ ID NO 126
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 126

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
                20                  25                  30

Val Gly Ser Asn Gly Xaa
        35

<210> SEQ ID NO 127
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 127

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
                20                  25                  30

Ile Gly Pro Gln Gly Xaa
        35

<210> SEQ ID NO 128
<211> LENGTH: 37
<212> TYPE: PRT
<213> ORGANISM: Artificial Sequence
<220> FEATURE:

<223> OTHER INFORMATION: Designed polypeptide

<400> SEQUENCE: 128

Lys Cys Asn Thr Ala Thr Cys Ala Thr Gln Arg Leu Ala Asn Phe Leu
1               5                   10                  15

Val His Ser Ser Asn Asn Phe Gly Ala Ile Ala Pro Ser Thr Lys Ile
            20                  25                  30

Gly Pro Asn Gly Tyr
        35

<210> SEQ ID NO 129
<211> LENGTH: 38
<212> TYPE: PRT
<213> ORGANISM: Artificial Sequence
<220> FEATURE:
<223> OTHER INFORMATION: Designed polypeptide

<400> SEQUENCE: 129

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Tyr
        35

<210> SEQ ID NO 130
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 130

Lys Cys Asn Thr Ala Thr Cys Thr Val Asp Arg Leu Ala His Gln Ile
1               5                   10                  15

Ala Gln Phe Thr Asp Lys Asp Lys Asp Pro Val Ala Pro Pro Thr Asn
            20                  25                  30

Val Gly Ser Asn Gly Xaa
        35

<210> SEQ ID NO 131
<211> LENGTH: 38
<212> TYPE: PRT
<213> ORGANISM: Artificial Sequence
<220> FEATURE:
<223> OTHER INFORMATION: Designed polypeptide

<400> SEQUENCE: 131

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Tyr
        35

<210> SEQ ID NO 132
<211> LENGTH: 38
<212> TYPE: PRT
<213> ORGANISM: Artificial Sequence

```
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 132

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Gln Gly Xaa
        35

<210> SEQ ID NO 133
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 133

Lys Cys Asn Thr Ala Thr Cys Thr Val Ala Arg Leu Ala Glu Gln Ile
1               5                   10                  15

Tyr Gln Phe Thr Asp Lys Asp Lys Asp Pro Val Ala Pro Pro Thr Asn
            20                  25                  30

Val Gly Ser Asn Gly Xaa
        35

<210> SEQ ID NO 134
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 134

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Asn Gly Xaa
        35

<210> SEQ ID NO 135
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

```
<400> SEQUENCE: 135

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Xaa
            35

<210> SEQ ID NO 136
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 136

Lys Cys Asn Thr Ala Thr Cys Thr Val Gln Arg Leu Ala Glu Gln Ile
1               5                   10                  15

Lys Gln Phe Thr Asp Lys Asp Lys Asp Asn Val Ala Pro Pro Thr Asn
            20                  25                  30

Val Gly Ser Asn Gly Xaa
            35

<210> SEQ ID NO 137
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 137

Lys Cys Asn Thr Ala Thr Cys Thr Val Ala Arg Leu Ala His Gln Ile
1               5                   10                  15

Asn Gln Phe Thr Asp Lys Asp Lys Asp Pro Val Ala Pro Pro Thr Asn
            20                  25                  30

Val Gly Ser Asn Gly Xaa
            35

<210> SEQ ID NO 138
<211> LENGTH: 38
<212> TYPE: PRT
<213> ORGANISM: Artificial Sequence
<220> FEATURE:
<223> OTHER INFORMATION: Designed polypeptide

<400> SEQUENCE: 138

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Tyr
            35

<210> SEQ ID NO 139
```

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 139

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Asn Gly Xaa
        35

<210> SEQ ID NO 140
<211> LENGTH: 38
<212> TYPE: PRT
<213> ORGANISM: Artificial Sequence
<220> FEATURE:
<223> OTHER INFORMATION: Designed polypeptide

<400> SEQUENCE: 140

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Gln Gly Tyr
        35

<210> SEQ ID NO 141
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 141

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Gln Gly Xaa
        35

<210> SEQ ID NO 142
<211> LENGTH: 38
<212> TYPE: PRT
<213> ORGANISM: Artificial Sequence
<220> FEATURE:
<223> OTHER INFORMATION: Designed polypeptide

<400> SEQUENCE: 142

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30
```

Ile Gly Pro Asn Gly Tyr
        35

<210> SEQ ID NO 143
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 143

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Xaa
        35

<210> SEQ ID NO 144
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 144

Lys Cys Asn Thr Ala Thr Cys Thr Val Gln Arg Leu Ala Glu Gln Ile
1               5                   10                  15

Ala Gln Phe Thr Asp Lys Asp Lys Asp Pro Val Ala Pro Pro Thr Asn
            20                  25                  30

Val Gly Ser Asn Gly Xaa
        35

<210> SEQ ID NO 145
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 145

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Xaa
        35

<210> SEQ ID NO 146
<211> LENGTH: 38
<212> TYPE: PRT
<213> ORGANISM: Artificial Sequence
<220> FEATURE:
<223> OTHER INFORMATION: Designed polypeptide

```
<220> FEATURE:
<221> NAME/KEY: MOD_RES
<222> LOCATION: (38)..(38)
<223> OTHER INFORMATION: 4Hyp

<400> SEQUENCE: 146

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Gln Gly Xaa
            35

<210> SEQ ID NO 147
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 147

Gly Cys Arg Ile Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Xaa
            35

<210> SEQ ID NO 148
<211> LENGTH: 37
<212> TYPE: PRT
<213> ORGANISM: Artificial Sequence
<220> FEATURE:
<223> OTHER INFORMATION: Designed polypeptide

<400> SEQUENCE: 148

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Lys Ile
            20                  25                  30

Gly Ser Asn Gly Tyr
            35

<210> SEQ ID NO 149
<211> LENGTH: 37
<212> TYPE: PRT
<213> ORGANISM: Artificial Sequence
<220> FEATURE:
<223> OTHER INFORMATION: Designed polypeptide

<400> SEQUENCE: 149

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Lys Val
            20                  25                  30

Gly Pro Asn Gly Tyr
            35

<210> SEQ ID NO 150
```

<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 150

Gly Cys Arg Trp Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Thr Xaa
        35

<210> SEQ ID NO 151
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 151

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Asn Gly Xaa
        35

<210> SEQ ID NO 152
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 152

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Xaa
        35

<210> SEQ ID NO 153
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:

<221> NAME/KEY: MOD_RES
<222> LOCATION: (38)..(38)
<223> OTHER INFORMATION: 4Hyp

<400> SEQUENCE: 153

Lys Cys Asn Thr Ala Thr Cys Thr Val Gln Xaa Leu Ala Glu Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 154
<211> LENGTH: 38
<212> TYPE: PRT
<213> ORGANISM: Artificial Sequence
<220> FEATURE:
<223> OTHER INFORMATION: Designed polypeptide

<400> SEQUENCE: 154

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 155
<211> LENGTH: 38
<212> TYPE: PRT
<213> ORGANISM: Artificial Sequence
<220> FEATURE:
<223> OTHER INFORMATION: Designed polypeptide

<400> SEQUENCE: 155

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Gln Gly Tyr
        35

<210> SEQ ID NO 156
<211> LENGTH: 38
<212> TYPE: PRT
<213> ORGANISM: Artificial Sequence
<220> FEATURE:
<223> OTHER INFORMATION: Designed polypeptide

<400> SEQUENCE: 156

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 157
<211> LENGTH: 38
<212> TYPE: PRT
<213> ORGANISM: Artificial Sequence
<220> FEATURE:
<223> OTHER INFORMATION: Designed polypeptide

```
<220> FEATURE:
<221> NAME/KEY: MOD_RES
<222> LOCATION: (38)..(38)
<223> OTHER INFORMATION: 4Hyp

<400> SEQUENCE: 157

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Gly Pro Asn Gly Xaa
            35

<210> SEQ ID NO 158
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 158

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Ser Pro Gln Gly Xaa
            35

<210> SEQ ID NO 159
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 159

Lys Cys Asn Thr Ala Thr Cys Thr Val Ile Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 160
<211> LENGTH: 38
<212> TYPE: PRT
<213> ORGANISM: Artificial Sequence
<220> FEATURE:
<223> OTHER INFORMATION: Designed polypeptide

<400> SEQUENCE: 160

Gly Cys Arg Thr Gly Thr Cys Thr Val Gln Arg Leu Ala His Gln Ile
1               5                   10                  15
```

Tyr Gln Phe Thr Asp Lys Asp Lys Asp Asn Val Ala Pro Arg Thr Asn
            20                  25                  30

Ile Gly Pro Gln Gly Tyr
        35

<210> SEQ ID NO 161
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 161

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Xaa
        35

<210> SEQ ID NO 162
<211> LENGTH: 37
<212> TYPE: PRT
<213> ORGANISM: Artificial Sequence
<220> FEATURE:
<223> OTHER INFORMATION: Designed polypeptide

<400> SEQUENCE: 162

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Lys Ile
            20                  25                  30

Gly Pro Asn Gly Tyr
        35

<210> SEQ ID NO 163
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 163

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Asn Gly Xaa
        35

<210> SEQ ID NO 164
<211> LENGTH: 38
<212> TYPE: PRT
<213> ORGANISM: Artificial Sequence
<220> FEATURE:
<223> OTHER INFORMATION: Designed polypeptide

<400> SEQUENCE: 164

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Gln Gly Tyr
        35

<210> SEQ ID NO 165
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 165

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Gln Gly Xaa
        35

<210> SEQ ID NO 166
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 166

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Asn Gly Xaa
        35

<210> SEQ ID NO 167
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 167

Gly Cys Arg Phe Gly Thr Cys Thr Val Gln Arg Leu Ala His Gln Ile
1               5                   10                  15

-continued

Tyr Gln Phe Thr Asp Lys Asp Lys Asp Asn Val Ala Pro Arg Ser Lys
            20                  25                  30

Val Ser Pro Gln Gly Xaa
        35

<210> SEQ ID NO 168
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 168

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Thr Xaa
        35

<210> SEQ ID NO 169
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 169

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Xaa
        35

<210> SEQ ID NO 170
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 170

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Asn Gly Xaa
        35

<210> SEQ ID NO 171
<211> LENGTH: 38

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 171

Gly Cys Arg Trp Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Xaa
        35

<210> SEQ ID NO 172
<211> LENGTH: 38
<212> TYPE: PRT
<213> ORGANISM: Artificial Sequence
<220> FEATURE:
<223> OTHER INFORMATION: Designed polypeptide

<400> SEQUENCE: 172

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Asn Gly Tyr
        35

<210> SEQ ID NO 173
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 173

Gly Cys Arg Met Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Xaa
        35

<210> SEQ ID NO 174
<211> LENGTH: 38
<212> TYPE: PRT
<213> ORGANISM: Artificial Sequence
<220> FEATURE:
<223> OTHER INFORMATION: Designed polypeptide

<400> SEQUENCE: 174

Gly Cys Arg Phe Gly Thr Cys Thr Val Gln Arg Leu Ala His Gln Ile
1               5                   10                  15
```

-continued

Tyr Gln Phe Thr Asp Lys Asp Lys Asp Asn Val Ala Pro Arg Ser Lys
                20                  25                  30

Val Ser Pro Gln Gly Tyr
        35

<210> SEQ ID NO 175
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 175

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
                20                  25                  30

Val Ser Pro Asn Gly Xaa
        35

<210> SEQ ID NO 176
<211> LENGTH: 38
<212> TYPE: PRT
<213> ORGANISM: Artificial Sequence
<220> FEATURE:
<223> OTHER INFORMATION: Designed polypeptide

<400> SEQUENCE: 176

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
                20                  25                  30

Val Ser Pro Gln Gly Tyr
        35

<210> SEQ ID NO 177
<211> LENGTH: 38
<212> TYPE: PRT
<213> ORGANISM: Artificial Sequence
<220> FEATURE:
<223> OTHER INFORMATION: Designed polypeptide

<400> SEQUENCE: 177

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
                20                  25                  30

Val Gly Pro Asn Gly Tyr
        35

<210> SEQ ID NO 178
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 178

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Gln Gly Xaa
            35

<210> SEQ ID NO 179
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 179

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Gly Pro Gln Gly Xaa
            35

<210> SEQ ID NO 180
<211> LENGTH: 37
<212> TYPE: PRT
<213> ORGANISM: Artificial Sequence
<220> FEATURE:
<223> OTHER INFORMATION: Designed polypeptide

<400> SEQUENCE: 180

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Lys Ile
            20                  25                  30

Gly Ser Asn Thr Tyr
            35

<210> SEQ ID NO 181
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 181

Lys Cys Asn Thr Ala Thr Cys Thr Val Gln Arg Leu Ala His Gln Ile
1               5                   10                  15

Tyr Phe Thr Asp Lys Asp Lys Asp Asn Val Ala Pro Pro Thr Asn Val
            20                  25                  30

Gly Ser Asn Gly Xaa
            35

<210> SEQ ID NO 182

```
<211> LENGTH: 38
<212> TYPE: PRT
<213> ORGANISM: Artificial Sequence
<220> FEATURE:
<223> OTHER INFORMATION: Designed polypeptide

<400> SEQUENCE: 182

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Ser Pro Gln Gly Tyr
        35

<210> SEQ ID NO 183
<211> LENGTH: 38
<212> TYPE: PRT
<213> ORGANISM: Artificial Sequence
<220> FEATURE:
<223> OTHER INFORMATION: Designed polypeptide

<400> SEQUENCE: 183

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Tyr
        35

<210> SEQ ID NO 184
<211> LENGTH: 38
<212> TYPE: PRT
<213> ORGANISM: Artificial Sequence
<220> FEATURE:
<223> OTHER INFORMATION: Designed polypeptide

<400> SEQUENCE: 184

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Trp
        35

<210> SEQ ID NO 185
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 185

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Trp Xaa
        35
```

-continued

```
<210> SEQ ID NO 186
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 186

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Tyr Xaa
            35

<210> SEQ ID NO 187
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 187

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Xaa
            35

<210> SEQ ID NO 188
<211> LENGTH: 38
<212> TYPE: PRT
<213> ORGANISM: Artificial Sequence
<220> FEATURE:
<223> OTHER INFORMATION: Designed polypeptide

<400> SEQUENCE: 188

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Asn Gly Tyr
            35

<210> SEQ ID NO 189
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

<400> SEQUENCE: 189

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Gln Gly Xaa
            35

<210> SEQ ID NO 190
<211> LENGTH: 38
<212> TYPE: PRT
<213> ORGANISM: Artificial Sequence
<220> FEATURE:
<223> OTHER INFORMATION: Designed polypeptide

<400> SEQUENCE: 190

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Asn Gly Tyr
            35

<210> SEQ ID NO 191
<211> LENGTH: 38
<212> TYPE: PRT
<213> ORGANISM: Artificial Sequence
<220> FEATURE:
<223> OTHER INFORMATION: Designed polypeptide

<400> SEQUENCE: 191

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Gln Gly Tyr
            35

<210> SEQ ID NO 192
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 192

Gly Cys Arg Met Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Thr Xaa
            35

<210> SEQ ID NO 193
<211> LENGTH: 38
<212> TYPE: PRT
<213> ORGANISM: Artificial Sequence
<220> FEATURE:

```
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 193

Gly Cys Arg Thr Gly Thr Cys Thr Val Gln Arg Leu Ala His Gln Ile
1               5                   10                  15
His Gln Phe Thr Asp Lys Phe Lys Asp Asn Val Ala Pro Arg Ser Lys
            20                  25                  30
Ile Ser Pro Gln Thr Xaa
        35

<210> SEQ ID NO 194
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 194

Lys Cys Arg Met Gly Thr Cys Thr Val Gln Arg Leu Ala His Gln Ile
1               5                   10                  15
Tyr Gln Phe Thr Asp Lys Asp Lys Asp Asn Val Ala Pro Arg Ser Lys
            20                  25                  30
Ile Ser Pro Gln Thr Xaa
        35

<210> SEQ ID NO 195
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 195

Lys Cys Asn Thr Ala Thr Cys Thr Val Gln Arg Leu Ala His Gln Ile
1               5                   10                  15
Tyr Gln Thr Asp Lys Asp Lys Asp Asn Val Ala Pro Pro Thr Asn Val
            20                  25                  30
Gly Ser Asn Gly Xaa
        35

<210> SEQ ID NO 196
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 196

Gly Cys Arg Thr Gly Thr Cys Thr Val Gln Arg Leu Ala His Gln Ile
1               5                   10                  15
```

-continued

Ala Gln Phe Thr Asp Lys Phe Lys Asp Asn Val Ala Pro Arg Ser Lys
            20                  25                  30

Ile Ser Pro Gln Thr Xaa
        35

<210> SEQ ID NO 197
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 197

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Asn Gly Xaa
        35

<210> SEQ ID NO 198
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 198

Gly Cys Arg Ile Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Thr Xaa
        35

<210> SEQ ID NO 199
<211> LENGTH: 38
<212> TYPE: PRT
<213> ORGANISM: Artificial Sequence
<220> FEATURE:
<223> OTHER INFORMATION: Designed polypeptide

<400> SEQUENCE: 199

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Gln Gly Tyr
        35

<210> SEQ ID NO 200
<211> LENGTH: 38
<212> TYPE: PRT
<213> ORGANISM: Artificial Sequence
<220> FEATURE:
<223> OTHER INFORMATION: Designed polypeptide

<400> SEQUENCE: 200

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
        35

<210> SEQ ID NO 201
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 201

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln His Xaa
        35

<210> SEQ ID NO 202
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 202

Gly Cys Arg Trp Gly Thr Cys Thr Val Gln Arg Leu Ala His Gln Ile
1               5                   10                  15

Tyr Gln Phe Thr Asp Lys Asp Lys Asp Asn Val Ala Pro Ser Ser Lys
            20                  25                  30

Ile Ser Pro Gln Thr Xaa
        35

<210> SEQ ID NO 203
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 203

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Pro Xaa
        35

<210> SEQ ID NO 204
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 204

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Ser Pro Asn Gly Xaa
        35

<210> SEQ ID NO 205
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 205

Lys Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Thr Xaa
        35

<210> SEQ ID NO 206
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 206

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Lys Xaa
        35

<210> SEQ ID NO 207
<211> LENGTH: 37

```
<212> TYPE: PRT
<213> ORGANISM: Artificial Sequence
<220> FEATURE:
<223> OTHER INFORMATION: Designed polypeptide

<400> SEQUENCE: 207

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Lys Ile
            20                  25                  30

Gly Ser Asn Gly Tyr
        35

<210> SEQ ID NO 208
<211> LENGTH: 38
<212> TYPE: PRT
<213> ORGANISM: Artificial Sequence
<220> FEATURE:
<223> OTHER INFORMATION: Designed polypeptide

<400> SEQUENCE: 208

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Asn
            20                  25                  30

Val Gly Ser Asn Thr Tyr
        35

<210> SEQ ID NO 209
<211> LENGTH: 38
<212> TYPE: PRT
<213> ORGANISM: Artificial Sequence
<220> FEATURE:
<223> OTHER INFORMATION: Designed polypeptide

<400> SEQUENCE: 209

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Gln Gly Tyr
        35

<210> SEQ ID NO 210
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 210

Lys Cys Asn Thr Ala Thr Cys Thr Val Gln Arg Leu Ala His Gln Ala
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 211
```

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 211

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Phe Xaa
        35

<210> SEQ ID NO 212
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 212

Gly Cys Arg Phe Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Xaa
        35

<210> SEQ ID NO 213
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 213

Gly Cys Arg Thr Gly Thr Cys Thr Val Gln Arg Leu Ala His Gln Ile
1               5                   10                  15

Trp Gln Phe Thr Asp Lys Phe Lys Asp Asn Val Ala Pro Arg Ser Lys
            20                  25                  30

Ile Ser Pro Gln Thr Xaa
        35

<210> SEQ ID NO 214
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

```
<400> SEQUENCE: 214

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Gln Gly Xaa
            35

<210> SEQ ID NO 215
<211> LENGTH: 38
<212> TYPE: PRT
<213> ORGANISM: Artificial Sequence
<220> FEATURE:
<223> OTHER INFORMATION: Designed polypeptide

<400> SEQUENCE: 215

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Met
            35

<210> SEQ ID NO 216
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 216

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Gln Gly Xaa
            35

<210> SEQ ID NO 217
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 217

Gly Cys Arg Phe Gly Thr Cys Thr Val Gln Arg Leu Ala His Gln Leu
1               5                   10                  15

Tyr Gln Phe Thr Asp Lys Asp Lys Asp Asn Val Ala Pro Arg Ser Lys
            20                  25                  30

Ile Ser Pro Gln Thr Xaa
            35

<210> SEQ ID NO 218
<211> LENGTH: 38
```

-continued

<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 218

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Ala Xaa
        35

<210> SEQ ID NO 219
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 219

Gly Cys Arg Thr Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln His Xaa
        35

<210> SEQ ID NO 220
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 220

Gly Cys Arg Thr Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Trp Xaa
        35

<210> SEQ ID NO 221
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 221

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 222
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 222

Gly Cys Arg Met Gly Thr Cys Thr Val Gln Arg Leu Ala His Gln Ile
1               5                   10                  15

Tyr Gln Phe Thr Asp Lys Asp Lys Asp Asn Val Ala Pro Ser Ser Lys
            20                  25                  30

Ile Ser Pro Gln Thr Xaa
            35

<210> SEQ ID NO 223
<211> LENGTH: 38
<212> TYPE: PRT
<213> ORGANISM: Artificial Sequence
<220> FEATURE:
<223> OTHER INFORMATION: Designed polypeptide

<400> SEQUENCE: 223

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Val Gly Ser Asn Gly Tyr
            35

<210> SEQ ID NO 224
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 224

Gly Cys Arg Thr Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Xaa
            35

<210> SEQ ID NO 225

-continued

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 225

Lys Cys Asn Thr Leu Thr Cys Thr Val Gln Arg Leu Ala His Gln Ile
 1               5                  10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 226
<211> LENGTH: 38
<212> TYPE: PRT
<213> ORGANISM: Artificial Sequence
<220> FEATURE:
<223> OTHER INFORMATION: Designed polypeptide

<400> SEQUENCE: 226

Gly Cys Arg Thr Gly Thr Cys Thr Val Gln Arg Leu Ala His Gln Ile
 1               5                  10                  15

Tyr Gln Phe Thr Asn Lys Asp Lys Asp Asn Val Ala Pro Arg Ser Lys
            20                  25                  30

Ile Ser Pro Gln Thr Trp
            35

<210> SEQ ID NO 227
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 227

Gly Cys Arg Thr Gly Thr Cys Thr Val Gln Arg Leu Ala His Gln Ile
 1               5                  10                  15

His Gln Phe Thr Asn Lys Asp Lys Asp Asn Val Ala Pro Arg Ser Lys
            20                  25                  30

Ile Ser Pro Gln Thr Xaa
            35

<210> SEQ ID NO 228
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 228

Gly Cys Arg Thr Gly Thr Cys Thr Val Gln Arg Leu Ala His Gln Ile
 1               5                  10                  15
```

His Gln Phe Thr Asp Lys Asp Lys Asp Asn Val Ala Pro Arg Ser Lys
            20                  25                  30

Ile Ser Pro Gln Thr Xaa
        35

<210> SEQ ID NO 229
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 229

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Gln Gly Xaa
        35

<210> SEQ ID NO 230
<211> LENGTH: 38
<212> TYPE: PRT
<213> ORGANISM: Artificial Sequence
<220> FEATURE:
<223> OTHER INFORMATION: Designed polypeptide

<400> SEQUENCE: 230

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Tyr
        35

<210> SEQ ID NO 231
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 231

Lys Cys Asn Thr Tyr Thr Cys Thr Val Gln Arg Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 232
<211> LENGTH: 38
<212> TYPE: PRT
<213> ORGANISM: Artificial Sequence
<220> FEATURE:
<223> OTHER INFORMATION: Designed polypeptide

```
<220> FEATURE:
<221> NAME/KEY: MOD_RES
<222> LOCATION: (38)..(38)
<223> OTHER INFORMATION: 4Hyp

<400> SEQUENCE: 232

Gly Cys Arg Thr Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Gln Xaa
        35

<210> SEQ ID NO 233
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 233

Lys Cys Asn Thr Ala Thr Cys Thr Val Gln Arg Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 234
<211> LENGTH: 38
<212> TYPE: PRT
<213> ORGANISM: Artificial Sequence
<220> FEATURE:
<223> OTHER INFORMATION: Designed polypeptide

<400> SEQUENCE: 234

Lys Cys Asn Thr Ala Thr Cys Ala Thr Gln Arg Leu Ala Asn Phe Leu
1               5                   10                  15

Val Gln Phe Thr Asp Lys Asp Lys Asp Asn Val Ala Pro Arg Ser Lys
            20                  25                  30

Ile Ser Pro Gln Gly Tyr
        35

<210> SEQ ID NO 235
<211> LENGTH: 38
<212> TYPE: PRT
<213> ORGANISM: Artificial Sequence
<220> FEATURE:
<223> OTHER INFORMATION: Designed polypeptide

<400> SEQUENCE: 235

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Pro
        35

<210> SEQ ID NO 236
```

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 236

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Met Xaa
        35

<210> SEQ ID NO 237
<211> LENGTH: 38
<212> TYPE: PRT
<213> ORGANISM: Artificial Sequence
<220> FEATURE:
<223> OTHER INFORMATION: Designed polypeptide

<400> SEQUENCE: 237

Gly Cys Arg Thr Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Thr Met
        35

<210> SEQ ID NO 238
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 238

Gly Cys Arg Thr Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Phe Xaa
        35

<210> SEQ ID NO 239
<211> LENGTH: 38
<212> TYPE: PRT
<213> ORGANISM: Artificial Sequence
<220> FEATURE:
<223> OTHER INFORMATION: Designed polypeptide

<400> SEQUENCE: 239

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30
```

Ile Ser Pro Gln Thr Phe
        35

<210> SEQ ID NO 240
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 240

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Ser Ser Lys
            20                  25                  30

Ile Ser Pro Gln Thr Xaa
        35

<210> SEQ ID NO 241
<211> LENGTH: 38
<212> TYPE: PRT
<213> ORGANISM: Artificial Sequence
<220> FEATURE:
<223> OTHER INFORMATION: Designed polypeptide

<400> SEQUENCE: 241

Gly Cys Arg Thr Gly Thr Cys Thr Val Gln Arg Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Ala
        35

<210> SEQ ID NO 242
<211> LENGTH: 38
<212> TYPE: PRT
<213> ORGANISM: Artificial Sequence
<220> FEATURE:
<223> OTHER INFORMATION: Designed polypeptide

<400> SEQUENCE: 242

Gly Cys Arg Thr Gly Thr Cys Thr Val Gln Arg Leu Ala His Gln Ile
1               5                   10                  15

Tyr Gln Phe Thr Asn Lys Asp Lys Asp Asn Val Ala Pro Arg Ser Lys
            20                  25                  30

Ile Ser Pro Gln Thr Arg
        35

<210> SEQ ID NO 243
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 243

Lys Cys Asn Thr Ala Thr Cys Thr Val Gln Xaa Leu Ala Ala Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 244
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 244

Lys Cys Asn Thr Ser Thr Cys Thr Val Ala Xaa Leu Ala Asp Gln Ile
1               5                   10                  15

Thr Gln Phe Ser Asn Lys Asp Lys Ala Gln Val Ser Pro Pro Thr Glu
            20                  25                  30

Val Gly Pro Asn Ser Xaa
            35

<210> SEQ ID NO 245
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 245

Arg Cys Asn Ala Ser Thr Cys Thr Val Asn Xaa Leu Ala Asp Gln Ile
1               5                   10                  15

Thr Gln Phe Ser Asn Lys Asp Lys Ala Gln Val Ser Pro Pro Thr Glu
            20                  25                  30

Val Gly Pro Asn Ser Xaa
            35

<210> SEQ ID NO 246
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 246

Lys Cys Asn Thr Ala Thr Cys Thr Val Gln Xaa Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
            35

<210> SEQ ID NO 247
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 247

Lys Cys Asn Thr Ser Thr Cys Thr Val Ala Xaa Leu Ala Asp Gln Ile
1               5                   10                  15

Thr Gln Phe Ser Asp Lys Asp Lys Ala Asn Val Ser Pro Pro Thr Glu
            20                  25                  30

Val Gly Pro Asn Ser Xaa
            35

<210> SEQ ID NO 248
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 248

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Xaa
            35

<210> SEQ ID NO 249
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline -continued

```
<220> FEATURE:
<221> NAME/KEY: MOD_RES
<222> LOCATION: (38)..(38)
<223> OTHER INFORMATION: 4Hyp

<400> SEQUENCE: 249

Lys Cys Asn Thr Ala Thr Cys Thr Val Gln Xaa Leu Ala His Gln Ile
1               5                   10                  15

Tyr Gln Phe Ala Asp Lys Asp Lys Asp Asn Val Ala Pro Pro Thr Asn
            20                  25                  30

Val Gly Ser Asn Gly Xaa
            35

<210> SEQ ID NO 250
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 250

Lys Cys Asn Thr Ala Thr Cys Thr Val Gln Xaa Leu Ala His Gln Ile
1               5                   10                  15

Tyr Gln Phe Thr Asp Lys Asp Ala Asp Asn Val Ala Pro Pro Thr Asn
            20                  25                  30

Val Gly Ser Asn Gly Xaa
            35

<210> SEQ ID NO 251
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 251

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Ala Ala Pro Pro Thr Asn
            20                  25                  30

Val Gly Ser Asn Gly Xaa
            35

<210> SEQ ID NO 252
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
```

<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 252

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Pro Ala Thr Asn
            20                  25                  30

Val Gly Ser Asn Gly Xaa
        35

<210> SEQ ID NO 253
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (37)..(37)
<223> OTHER INFORMATION: 4Hyp

<400> SEQUENCE: 253

Lys Cys Asn Thr Ala Thr Cys Thr Val Gln Xaa Leu Ala His Gln Ile
1               5                   10                  15

Tyr Gln Phe Thr Lys Asp Lys Asp Asn Val Ala Pro Pro Thr Asn Val
            20                  25                  30

Gly Ser Asn Gly Xaa
        35

<210> SEQ ID NO 254
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (37)..(37)
<223> OTHER INFORMATION: 4Hyp

<400> SEQUENCE: 254

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Pro Pro Thr Asn Val
            20                  25                  30

Gly Ser Asn Gly Xaa
        35

<210> SEQ ID NO 255
<211> LENGTH: 37
<212> TYPE: PRT
<213> ORGANISM: Artificial Sequence
<220> FEATURE:
<223> OTHER INFORMATION: Designed polypeptide

```
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (37)..(37)
<223> OTHER INFORMATION: 4Hyp

<400> SEQUENCE: 255

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Pro Thr Asn Val
            20                  25                  30

Gly Ser Asn Gly Xaa
            35

<210> SEQ ID NO 256
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 256

Arg Cys Gln Thr Ser Thr Cys Thr Val Ala Xaa Leu Ala Glu Gln Ile
1               5                   10                  15

Ala Gln Tyr Thr Asp Lys Asp Lys Asp Gln Val Ala Pro Pro Thr Asn
            20                  25                  30

Val Gly Ser Asn Ser Xaa
            35

<210> SEQ ID NO 257
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 257

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Tyr
            35

<210> SEQ ID NO 258
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
```

```
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 258

Lys Cys Asn Thr Ala Thr Cys Thr Val Gln Xaa Leu Ala His Gln Ile
1               5                   10                  15

Tyr Gln Phe Thr Asp Lys Ala Lys Asp Asn Val Ala Pro Pro Thr Asn
            20                  25                  30

Val Gly Ser Asn Gly Xaa
        35

<210> SEQ ID NO 259
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 259

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Xaa
        35

<210> SEQ ID NO 260
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 260

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Gln Gly Xaa
        35

<210> SEQ ID NO 261
<211> LENGTH: 38
<212> TYPE: PRT
<213> ORGANISM: Artificial Sequence
<220> FEATURE:
<223> OTHER INFORMATION: Designed polypeptide
```

```
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 261

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Xaa
            35

<210> SEQ ID NO 262
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 262

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Ala Pro Thr Asn
            20                  25                  30

Val Gly Ser Asn Gly Xaa
            35

<210> SEQ ID NO 263
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 263

Gly Cys Arg Phe Gly Thr Cys Thr Val Gln Xaa Leu Ala His Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 264
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
```

<222> LOCATION: (11)..(11)
<223> OTHER INFORMATION: L-citrulline

<400> SEQUENCE: 264

Gly Cys Arg Phe Gly Thr Cys Thr Val Gln Xaa Leu Ala His Phe Leu
1               5                   10                  15

Tyr Gln Phe Thr Asp Lys Asp Lys Asp Asn Val Ala Pro Arg Thr Asn
            20                  25                  30

Val Gly Ser Asn Thr Tyr
            35

<210> SEQ ID NO 265
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (37)..(37)
<223> OTHER INFORMATION: 4Hyp

<400> SEQUENCE: 265

Lys Cys Asn Thr Ala Thr Cys Thr Val Gln Xaa Leu Ala His Gln Ile
1               5                   10                  15

Tyr Gln Phe Asp Lys Asp Lys Asp Asn Val Ala Pro Pro Thr Asn Val
            20                  25                  30

Gly Ser Asn Gly Xaa
            35

<210> SEQ ID NO 266
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 266

Lys Cys Asn Thr Ala Thr Cys Thr Val Gln Xaa Leu Ala Glu Gln Ile
1               5                   10                  15

Tyr Gln Phe Thr Asp Lys Asp Lys Asp Asn Val Ser Pro Pro Thr Asn
            20                  25                  30

Val Gly Ser Asn Gly Xaa
            35

<210> SEQ ID NO 267
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

```
<220> FEATURE:
<221> NAME/KEY: MOD_RES
<222> LOCATION: (38)..(38)
<223> OTHER INFORMATION: 4Hyp

<400> SEQUENCE: 267

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Xaa
            35

<210> SEQ ID NO 268
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 268

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 269
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 269

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Asn Gly Tyr
            35

<210> SEQ ID NO 270
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
```

```
<222> LOCATION: (38)..(38)
<223> OTHER INFORMATION: 4Hyp

<400> SEQUENCE: 270

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Asn Gly Xaa
            35

<210> SEQ ID NO 271
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 271

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Asn Gly Tyr
            35

<210> SEQ ID NO 272
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 272

Lys Cys Asn Thr Ala Thr Cys Thr Val Gln Xaa Leu Ala His Gln Ile
1               5                   10                  15

Tyr Gln Phe Thr Asp Lys Asp Lys Asp Asn Val Ala Pro Arg Thr Glu
            20                  25                  30

Val Gly Ser Asn Gly Tyr
            35

<210> SEQ ID NO 273
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 273

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30
```

Val Gly Pro Gln Gly Tyr
            35

<210> SEQ ID NO 274
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 274

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Xaa
            35

<210> SEQ ID NO 275
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 275

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Asn Gly Xaa
            35

<210> SEQ ID NO 276
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 276

Lys Cys Asn Thr Ala Thr Cys Thr Val Gln Xaa Leu Ala His Gln Ile
1               5                   10                  15

Tyr Gln Ala Thr Asp Lys Asp Lys Asp Asn Val Ala Pro Pro Thr Asn
            20                  25                  30

Val Gly Ser Asn Gly Xaa
        35

<210> SEQ ID NO 277
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 277

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Asn Gly Xaa
        35

<210> SEQ ID NO 278
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 278

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Gln Gly Tyr
        35

<210> SEQ ID NO 279
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 279

Gly Cys Arg Phe Gly Thr Cys Thr Val Gln Xaa Leu Ala His Phe Leu
1               5                   10                  15

Tyr Gln Phe Thr Asp Lys Asp Lys Asp Asn Val Ala Pro Arg Thr Lys
            20                  25                  30

Val Gly Ser Asn Gly Tyr
        35

<210> SEQ ID NO 280
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 280

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Gln Gly Xaa
        35

<210> SEQ ID NO 281
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 281

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Xaa
        35

<210> SEQ ID NO 282
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 282

Gly Cys Arg Phe Gly Thr Cys Thr Val Gln Xaa Leu Ala His Phe Leu
1               5                   10                  15

Tyr Gln Phe Thr Asp Lys Asp Gly Ala Ile Ala Pro Arg Thr Lys Ile
            20                  25                  30

Gly Ser Gln Gly Tyr
        35

<210> SEQ ID NO 283

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 283

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Gln Gly Xaa
        35

<210> SEQ ID NO 284
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 284

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Lys
            20                  25                  30

Ile Gly Pro Gln Gly Xaa
        35

<210> SEQ ID NO 285
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 285

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Tyr
        35

<210> SEQ ID NO 286
<211> LENGTH: 38
<212> TYPE: PRT
```

<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 286

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Tyr
        35

<210> SEQ ID NO 287
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 287

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Gln Gly Xaa
        35

<210> SEQ ID NO 288
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 288

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Asn Gly Xaa
        35

<210> SEQ ID NO 289
<211> LENGTH: 38
<212> TYPE: PRT
<213> ORGANISM: Artificial Sequence
<220> FEATURE:

<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 289

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Xaa
        35

<210> SEQ ID NO 290
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 290

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Asn Gly Xaa
        35

<210> SEQ ID NO 291
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 291

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Gln Gly Xaa
        35

<210> SEQ ID NO 292
<211> LENGTH: 38
<212> TYPE: PRT

```
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 292

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Xaa
        35

<210> SEQ ID NO 293
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 293

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Xaa
        35

<210> SEQ ID NO 294
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 294

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Gln Gly Xaa
        35

<210> SEQ ID NO 295
```

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 295

Gly Cys Arg Ile Gly Thr Cys Thr Val Gln Xaa Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Xaa
        35

<210> SEQ ID NO 296
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 296

Gly Cys Arg Trp Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Thr Xaa
        35

<210> SEQ ID NO 297
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 297

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Asn Gly Xaa
        35
```

-continued

<210> SEQ ID NO 298
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline

<400> SEQUENCE: 298

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 299
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 299

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Lys
            20                  25                  30

Ile Gly Pro Asn Gly Xaa
        35

<210> SEQ ID NO 300
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 300

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Ile Ser Pro Gln Gly Xaa
        35

<210> SEQ ID NO 301

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 301

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Xaa
        35

<210> SEQ ID NO 302
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 302

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Asn Gly Xaa
        35

<210> SEQ ID NO 303
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 303

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Gln Gly Xaa
        35
```

```
<210> SEQ ID NO 304
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 304

Gly Cys Arg Thr Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Asn Gly Xaa
        35

<210> SEQ ID NO 305
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (11)..(11)
<223> OTHER INFORMATION: L-citrulline
<220> FEATURE:
<221> NAME/KEY: MOD_RES
<222> LOCATION: (38)..(38)
<223> OTHER INFORMATION: 4Hyp

<400> SEQUENCE: 305

Gly Cys Arg Phe Gly Thr Cys Thr Val Gln Xaa Leu Ala His Gln Ile
1               5                   10                  15

Tyr Gln Phe Thr Asp Lys Asp Lys Asp Asn Val Ala Pro Arg Ser Lys
            20                  25                  30

Val Ser Pro Gln Gly Xaa
        35

<210> SEQ ID NO 306
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 306

Lys Cys Asn Thr Ser Thr Cys Thr Val Ala Trp Leu Ala Asp Gln Ile
1               5                   10                  15

Thr Gln Phe Ser Asn Lys Asp Lys Ala Gln Val Ser Pro Pro Thr Glu
            20                  25                  30

Val Gly Pro Asn Ser Xaa
        35

<210> SEQ ID NO 307
```

```
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 307

Arg Cys Asn Ala Ser Thr Cys Thr Val Asn Trp Leu Ala Asp Gln Ile
1               5                   10                  15

Thr Gln Phe Ser Asn Lys Asp Lys Ala Gln Val Ser Pro Pro Thr Glu
            20                  25                  30

Val Gly Pro Asn Ser Xaa
        35

<210> SEQ ID NO 308
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 308

Lys Cys Asn Thr Ala Thr Cys Thr Val Gln Trp Leu Ala His Ala Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 309
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 309

Lys Cys Asn Thr Ala Thr Cys Thr Val Gln Trp Leu Ala His Gln Ile
1               5                   10                  15

Ala Gln Phe Thr Asp Lys Asp Lys Asp Asn Val Ala Pro Pro Thr Asn
            20                  25                  30

Val Gly Ser Asn Gly Xaa
        35

<210> SEQ ID NO 310
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp
```

```
<400> SEQUENCE: 310

Lys Cys Asn Thr Ser Thr Cys Thr Val Ala Trp Leu Ala Asp Gln Ile
1               5                   10                  15

Thr Gln Phe Ser Asp Lys Asp Lys Ala Asn Val Ser Pro Pro Thr Glu
            20                  25                  30

Val Gly Pro Asn Ser Xaa
            35

<210> SEQ ID NO 311
<211> LENGTH: 38
<212> TYPE: PRT
<213> ORGANISM: Artificial Sequence
<220> FEATURE:
<223> OTHER INFORMATION: Designed polypeptide

<400> SEQUENCE: 311

Gly Cys Arg Phe Gly Thr Cys Thr Val Gln Trp Leu Ala Asn Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 312
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 312

Lys Cys Asn Thr Ala Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Xaa
            35

<210> SEQ ID NO 313
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 313

Lys Cys Asn Thr Ala Thr Cys Thr Val Gln Trp Leu Ala His Gln Ile
1               5                   10                  15

Tyr Gln Phe Ala Asp Lys Asp Lys Asp Asn Val Ala Pro Pro Thr Asn
            20                  25                  30

Val Gly Ser Asn Gly Xaa
            35

<210> SEQ ID NO 314
<211> LENGTH: 38
```

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 314

Lys Cys Asn Thr Ala Thr Cys Thr Val Gln Trp Leu Ala His Gln Ile
1               5                   10                  15

Tyr Gln Phe Thr Asp Lys Asp Lys Ala Asn Val Ala Pro Pro Thr Asn
            20                  25                  30

Val Gly Ser Asn Gly Xaa
        35

<210> SEQ ID NO 315
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 315

Lys Cys Asn Thr Ala Thr Cys Thr Val Gln Trp Leu Ala His Gln Ile
1               5                   10                  15

Tyr Gln Phe Thr Asp Lys Asp Lys Asp Asn Ala Ala Pro Pro Thr Asn
            20                  25                  30

Val Gly Ser Asn Gly Xaa
        35

<210> SEQ ID NO 316
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 316

Lys Cys Asn Thr Ala Thr Cys Thr Val Gln Trp Leu Ala His Gln Ile
1               5                   10                  15

Tyr Gln Phe Thr Asp Lys Asp Lys Asp Asn Val Ala Pro Ala Thr Asn
            20                  25                  30

Val Gly Ser Asn Gly Xaa
        35

<210> SEQ ID NO 317
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp
```

<400> SEQUENCE: 317

Lys Cys Asn Thr Ala Thr Cys Thr Val Gln Trp Leu Ala His Gln Ile
1               5                   10                  15

Tyr Gln Phe Thr Lys Asp Lys Asp Asn Val Ala Pro Pro Thr Asn Val
            20                  25                  30

Gly Ser Asn Gly Xaa
        35

<210> SEQ ID NO 318
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 318

Lys Cys Asn Thr Ala Thr Cys Thr Val Gln Trp Leu Ala His Gln Ile
1               5                   10                  15

Tyr Gln Phe Thr Asp Lys Asp Lys Asn Val Pro Pro Thr Asn Val
            20                  25                  30

Gly Ser Asn Gly Xaa
        35

<210> SEQ ID NO 319
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 319

Lys Cys Asn Thr Ala Thr Cys Thr Val Gln Trp Leu Ala His Gln Ile
1               5                   10                  15

Tyr Gln Phe Thr Asp Lys Asp Lys Asn Val Ala Pro Thr Asn Val
            20                  25                  30

Gly Ser Asn Gly Xaa
        35

<210> SEQ ID NO 320
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 320

Lys Cys Asn Thr Ala Thr Cys Thr Val Gln Trp Leu Ala His Gln Ile
1               5                   10                  15

-continued

```
Tyr Gln Phe Thr Asp Lys Ala Lys Asp Asn Val Ala Pro Pro Thr Asn
            20                  25                  30

Val Gly Ser Asn Gly Xaa
        35

<210> SEQ ID NO 321
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 321

Lys Cys Asn Thr Ala Thr Cys Thr Val Gln Trp Leu Ala Glu Gln Ile
 1               5                  10                  15

Tyr Gln Phe Thr Asp Lys Asp Lys Asp Asn Val Ala Pro Pro Tyr Asn
            20                  25                  30

Glu Gly Ser Asn Gly Xaa
        35

<210> SEQ ID NO 322
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 322

Gly Cys Arg Phe Gly Thr Cys Thr Val Gln Trp Leu Ala His Gln Ile
 1               5                  10                  15

Tyr Gln Phe Thr Asp Lys Asp Lys Asp Asn Val Ala Pro Arg Thr Lys
            20                  25                  30

Val Gly Pro Gln Gly Xaa
        35

<210> SEQ ID NO 323
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 323

Gly Cys Arg Thr Gly Thr Cys Thr Val Gln Trp Leu Ala His Gln Ile
 1               5                  10                  15

Tyr Gln Phe Thr Asp Lys Asp Lys Asp Asn Val Ala Pro Arg Thr Asn
            20                  25                  30

Val Gly Pro Gln Gly Xaa
        35

<210> SEQ ID NO 324
<211> LENGTH: 38
```

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 324

Lys Cys Asn Thr Ala Thr Cys Thr Val Gln Trp Leu Ala His Gln Ile
1               5                   10                  15

Tyr Gln Phe Thr Asp Lys Asp Lys Asp Ala Val Ala Pro Pro Thr Asn
            20                  25                  30

Val Gly Ser Asn Gly Xaa
            35

<210> SEQ ID NO 325
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 325

Lys Cys Asn Thr Ala Thr Cys Thr Val Gln Trp Leu Ala His Gln Ile
1               5                   10                  15

Tyr Gln Phe Thr Asp Lys Asp Lys Asp Asn Val Ala Ala Pro Thr Asn
            20                  25                  30

Val Gly Ser Asn Gly Xaa
            35

<210> SEQ ID NO 326
<211> LENGTH: 38
<212> TYPE: PRT
<213> ORGANISM: Artificial Sequence
<220> FEATURE:
<223> OTHER INFORMATION: Designed polypeptide

<400> SEQUENCE: 326

Gly Cys Arg Phe Gly Thr Cys Thr Val Gln Trp Leu Ala His Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 327
<211> LENGTH: 38
<212> TYPE: PRT
<213> ORGANISM: Artificial Sequence
<220> FEATURE:
<223> OTHER INFORMATION: Designed polypeptide

<400> SEQUENCE: 327

Gly Cys Arg Phe Gly Thr Cys Thr Val Gln Trp Leu Ala His Phe Leu
1               5                   10                  15
```

-continued

Tyr Gln Phe Thr Asp Lys Asp Lys Asp Asn Val Ala Pro Arg Thr Asn
            20                  25                  30

Val Gly Ser Asn Thr Tyr
            35

<210> SEQ ID NO 328
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 328

Lys Cys Asn Thr Ala Thr Cys Thr Val Gln Trp Leu Ala His Gln Ile
1               5                   10                  15

Tyr Gln Phe Thr Asp Ala Asp Lys Asp Asn Val Ala Pro Pro Thr Asn
            20                  25                  30

Val Gly Ser Asn Gly Xaa
            35

<210> SEQ ID NO 329
<211> LENGTH: 37
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (37)..(37)
<223> OTHER INFORMATION: 4Hyp

<400> SEQUENCE: 329

Lys Cys Asn Thr Ala Thr Cys Thr Val Gln Trp Leu Ala His Gln Ile
1               5                   10                  15

Tyr Gln Phe Asp Lys Asp Lys Asp Asn Val Ala Pro Pro Thr Asn Val
            20                  25                  30

Gly Ser Asn Gly Xaa
            35

<210> SEQ ID NO 330
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 330

Lys Cys Asn Thr Ala Thr Cys Thr Val Gln Trp Leu Ala His Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
            35

<210> SEQ ID NO 331
<211> LENGTH: 38

```
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 331

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Asn Gly Xaa
        35

<210> SEQ ID NO 332
<211> LENGTH: 38
<212> TYPE: PRT
<213> ORGANISM: Artificial Sequence
<220> FEATURE:
<223> OTHER INFORMATION: Designed polypeptide

<400> SEQUENCE: 332

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Asn Gly Tyr
        35

<210> SEQ ID NO 333
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 333

Lys Cys Asn Ala Ala Thr Cys Thr Val Gln Trp Leu Ala Glu Gln Ile
1               5                   10                  15

Tyr Gln Phe Thr Asp Lys Asp Lys Asp Asn Val Ala Pro Pro Thr Asn
            20                  25                  30

Val Gly Ser Asn Gly Xaa
        35

<210> SEQ ID NO 334
<211> LENGTH: 38
<212> TYPE: PRT
<213> ORGANISM: Artificial Sequence
<220> FEATURE:
<223> OTHER INFORMATION: Designed polypeptide

<400> SEQUENCE: 334

Lys Cys Asn Thr Ala Thr Cys Thr Val Gln Trp Leu Ala His Gln Ile
1               5                   10                  15
```

```
Tyr Gln Phe Thr Asp Lys Asp Lys Asp Asn Val Ala Pro Arg Thr Glu
            20                  25                  30

Val Gly Ser Asn Gly Tyr
        35

<210> SEQ ID NO 335
<211> LENGTH: 38
<212> TYPE: PRT
<213> ORGANISM: Artificial Sequence
<220> FEATURE:
<223> OTHER INFORMATION: Designed polypeptide

<400> SEQUENCE: 335

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Tyr
        35

<210> SEQ ID NO 336
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 336

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Xaa
        35

<210> SEQ ID NO 337
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 337

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Asn Gly Xaa
        35

<210> SEQ ID NO 338
<211> LENGTH: 38
<212> TYPE: PRT
<213> ORGANISM: Artificial Sequence
<220> FEATURE:
<223> OTHER INFORMATION: Designed polypeptide
```

<220> FEATURE:
<221> NAME/KEY: MOD_RES
<222> LOCATION: (38)..(38)
<223> OTHER INFORMATION: 4Hyp

<400> SEQUENCE: 338

Lys Cys Asn Thr Ala Thr Cys Thr Val Gln Trp Leu Ala His Gln Ile
1               5                   10                  15

Tyr Gln Ala Thr Asp Lys Asp Lys Asp Asn Val Ala Pro Pro Thr Asn
            20                  25                  30

Val Gly Ser Asn Gly Xaa
        35

<210> SEQ ID NO 339
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 339

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Asn Gly Xaa
        35

<210> SEQ ID NO 340
<211> LENGTH: 38
<212> TYPE: PRT
<213> ORGANISM: Artificial Sequence
<220> FEATURE:
<223> OTHER INFORMATION: Designed polypeptide

<400> SEQUENCE: 340

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Gln Gly Tyr
        35

<210> SEQ ID NO 341
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 341

Gly Cys Arg Thr Gly Thr Cys Thr Val Gln Trp Leu Ala His Gln Ile
1               5                   10                  15

```
Tyr Gln Phe Thr Asp Lys Asp Lys Asp Asn Val Ala Pro Arg Thr Asn
            20                  25                  30

Ile Gly Pro Gln Gly Xaa
        35

<210> SEQ ID NO 342
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 342

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Xaa
        35

<210> SEQ ID NO 343
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 343

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Asn Gly Xaa
        35

<210> SEQ ID NO 344
<211> LENGTH: 38
<212> TYPE: PRT
<213> ORGANISM: Artificial Sequence
<220> FEATURE:
<223> OTHER INFORMATION: Designed polypeptide

<400> SEQUENCE: 344

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Tyr
        35

<210> SEQ ID NO 345
<211> LENGTH: 38
<212> TYPE: PRT
<213> ORGANISM: Artificial Sequence
<220> FEATURE:
<223> OTHER INFORMATION: Designed polypeptide
```

<400> SEQUENCE: 345

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Asn
            20                  25                  30

Val Ser Pro Gln Gly Tyr
            35

<210> SEQ ID NO 346
<211> LENGTH: 38
<212> TYPE: PRT
<213> ORGANISM: Artificial Sequence
<220> FEATURE:
<223> OTHER INFORMATION: Designed polypeptide

<400> SEQUENCE: 346

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Tyr
            35

<210> SEQ ID NO 347
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 347

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Asn Gly Xaa
            35

<210> SEQ ID NO 348
<211> LENGTH: 38
<212> TYPE: PRT
<213> ORGANISM: Artificial Sequence
<220> FEATURE:
<223> OTHER INFORMATION: Designed polypeptide

<400> SEQUENCE: 348

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Asn Gly Tyr
            35

<210> SEQ ID NO 349
<211> LENGTH: 38
<212> TYPE: PRT
<213> ORGANISM: Artificial Sequence
<220> FEATURE:

<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 349

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Xaa
        35

<210> SEQ ID NO 350
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 350

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Gln Gly Xaa
        35

<210> SEQ ID NO 351
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 351

Gly Cys Arg Ile Gly Thr Cys Thr Val Gln Trp Leu Ala His Gln Ile
1               5                   10                  15

Tyr Gln Phe Thr Asp Lys Phe Lys Asp Asn Val Ala Pro Arg Ser Lys
            20                  25                  30

Ile Ser Pro Gln Thr Xaa
        35

<210> SEQ ID NO 352
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 352

Gly Cys Arg Thr Gly Thr Cys Thr Val Gln Trp Leu Ala His Gln Ile
1               5                   10                  15

-continued

Tyr Gln Phe Thr Asp Lys Asp Lys Asp Asn Val Ala Pro Arg Ser Asn
            20                  25                  30

Ile Gly Pro Asn Gly Xaa
        35

<210> SEQ ID NO 353
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 353

Gly Cys Arg Phe Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Xaa
        35

<210> SEQ ID NO 354
<211> LENGTH: 38
<212> TYPE: PRT
<213> ORGANISM: Artificial Sequence
<220> FEATURE:
<223> OTHER INFORMATION: Designed polypeptide

<400> SEQUENCE: 354

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 355
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 355

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Lys
            20                  25                  30

Ile Gly Pro Asn Gly Xaa
        35

<210> SEQ ID NO 356
<211> LENGTH: 38
<212> TYPE: PRT
<213> ORGANISM: Artificial Sequence
<220> FEATURE:
<223> OTHER INFORMATION: Designed polypeptide

<400> SEQUENCE: 356

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Gln Gly Tyr
        35

<210> SEQ ID NO 357
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 357

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Xaa
        35

<210> SEQ ID NO 358
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 358

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Thr Asn
            20                  25                  30

Val Ser Pro Asn Gly Xaa
        35

<210> SEQ ID NO 359
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 359

Gly Cys Arg Thr Gly Thr Cys Thr Val Gln Trp Leu Ala His Gln Ile
1               5                   10                  15

-continued

Tyr Gln Phe Thr Asp Lys Asp Lys Asp Asn Val Ala Pro Arg Ser Asn
                20                  25                  30

Ile Gly Pro Gln Gly Xaa
        35

<210> SEQ ID NO 360
<211> LENGTH: 38
<212> TYPE: PRT
<213> ORGANISM: Artificial Sequence
<220> FEATURE:
<223> OTHER INFORMATION: Designed polypeptide
<220> FEATURE:
<221> NAME/KEY: MOD_RES
<222> LOCATION: (38)..(38)
<223> OTHER INFORMATION: 4Hyp

<400> SEQUENCE: 360

Gly Cys Arg Thr Gly Thr Cys Thr Val Gln Trp Leu Ala His Gln Ile
1               5                   10                  15

Tyr Gln Phe Thr Asp Lys Asp Lys Asp Asn Val Ala Pro Arg Ser Asn
                20                  25                  30

Val Ser Pro Asn Gly Xaa
        35

<210> SEQ ID NO 361
<211> LENGTH: 38
<212> TYPE: PRT
<213> ORGANISM: Artificial Sequence
<220> FEATURE:
<223> OTHER INFORMATION: Designed polypeptide

<400> SEQUENCE: 361

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
                20                  25                  30

Val Gly Ser Asn Gly Tyr
        35

<210> SEQ ID NO 362
<211> LENGTH: 38
<212> TYPE: PRT
<213> ORGANISM: Artificial Sequence
<220> FEATURE:
<223> OTHER INFORMATION: Designed polypeptide

<400> SEQUENCE: 362

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
                20                  25                  30

Val Gly Pro Gln Gly Tyr
        35

<210> SEQ ID NO 363
<211> LENGTH: 38
<212> TYPE: PRT
<213> ORGANISM: Artificial Sequence
<220> FEATURE:
<223> OTHER INFORMATION: Designed polypeptide

<400> SEQUENCE: 363

Lys Cys Asn Phe Ala Thr Cys Ala Thr Gln Arg Leu Ala Asn Phe Leu
1               5                   10                  15

Val Gln Phe Thr Asp Lys Asp Lys Asp Asn Val Ala Pro Arg Ser Lys
            20                  25                  30

Ile Gly Pro Gln Gly Tyr
            35

<210> SEQ ID NO 364
<211> LENGTH: 38
<212> TYPE: PRT
<213> ORGANISM: Artificial Sequence
<220> FEATURE:
<223> OTHER INFORMATION: Designed polypeptide

<400> SEQUENCE: 364

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Asn
            20                  25                  30

Ile Gly Pro Gln Gly Tyr
            35

<210> SEQ ID NO 365
<211> LENGTH: 38
<212> TYPE: PRT
<213> ORGANISM: Artificial Sequence
<220> FEATURE:
<223> OTHER INFORMATION: Designed polypeptide

<400> SEQUENCE: 365

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Ile Gly Pro Gln Gly Tyr
            35

<210> SEQ ID NO 366
<211> LENGTH: 38
<212> TYPE: PRT
<213> ORGANISM: Artificial Sequence
<220> FEATURE:
<223> OTHER INFORMATION: Designed polypeptide

<400> SEQUENCE: 366

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Ser Pro Asn Gly Tyr
            35

<210> SEQ ID NO 367
<211> LENGTH: 38
<212> TYPE: PRT
<213> ORGANISM: Artificial Sequence
<220> FEATURE:
<223> OTHER INFORMATION: Designed polypeptide

<400> SEQUENCE: 367

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Asn Gly Tyr
        35

<210> SEQ ID NO 368
<211> LENGTH: 38
<212> TYPE: PRT
<213> ORGANISM: Artificial Sequence
<220> FEATURE:
<223> OTHER INFORMATION: Designed polypeptide

<400> SEQUENCE: 368

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 369
<211> LENGTH: 38
<212> TYPE: PRT
<213> ORGANISM: Artificial Sequence
<220> FEATURE:
<223> OTHER INFORMATION: Designed polypeptide

<400> SEQUENCE: 369

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 370
<211> LENGTH: 38
<212> TYPE: PRT
<213> ORGANISM: Artificial Sequence
<220> FEATURE:
<223> OTHER INFORMATION: Designed polypeptide

<400> SEQUENCE: 370

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Glu
            20                  25                  30

Val Gly Ser Asn Gly Tyr
        35

<210> SEQ ID NO 371
<211> LENGTH: 38
<212> TYPE: PRT
<213> ORGANISM: Artificial Sequence
<220> FEATURE:
<223> OTHER INFORMATION: Designed polypeptide

<400> SEQUENCE: 371

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Ser Pro Asn Gly Tyr
            35

<210> SEQ ID NO 372
<211> LENGTH: 38
<212> TYPE: PRT
<213> ORGANISM: Artificial Sequence
<220> FEATURE:
<223> OTHER INFORMATION: Designed polypeptide

<400> SEQUENCE: 372

Gly Cys Arg Phe Gly Thr Cys Thr Val Gln Arg Leu Ala Asn Gln Ile
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 373
<211> LENGTH: 38
<212> TYPE: PRT
<213> ORGANISM: Artificial Sequence
<220> FEATURE:
<223> OTHER INFORMATION: Designed polypeptide

<400> SEQUENCE: 373

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Asn Gly Tyr
            35

<210> SEQ ID NO 374
<211> LENGTH: 38
<212> TYPE: PRT
<213> ORGANISM: Artificial Sequence
<220> FEATURE:
<223> OTHER INFORMATION: Designed polypeptide

<400> SEQUENCE: 374

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Val Gly Pro Gln Gly Tyr
            35

<210> SEQ ID NO 375
<211> LENGTH: 38
<212> TYPE: PRT
<213> ORGANISM: Artificial Sequence
<220> FEATURE:
<223> OTHER INFORMATION: Designed polypeptide

<400> SEQUENCE: 375

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Gly Pro Gln Gly Tyr
        35

<210> SEQ ID NO 376
<211> LENGTH: 38
<212> TYPE: PRT
<213> ORGANISM: Artificial Sequence
<220> FEATURE:
<223> OTHER INFORMATION: Designed polypeptide

<400> SEQUENCE: 376

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Ile Gly Ser Asn Gly Tyr
        35

<210> SEQ ID NO 377
<211> LENGTH: 38
<212> TYPE: PRT
<213> ORGANISM: Artificial Sequence
<220> FEATURE:
<223> OTHER INFORMATION: Designed polypeptide

<400> SEQUENCE: 377

Gly Cys Arg Phe Ala Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 378
<211> LENGTH: 38
<212> TYPE: PRT
<213> ORGANISM: Artificial Sequence
<220> FEATURE:
<223> OTHER INFORMATION: Designed polypeptide

<400> SEQUENCE: 378

Lys Cys Asn Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Ser Asn Gly Tyr
        35

<210> SEQ ID NO 379
<211> LENGTH: 38
<212> TYPE: PRT
<213> ORGANISM: Artificial Sequence
<220> FEATURE:
<223> OTHER INFORMATION: Designed polypeptide

<400> SEQUENCE: 379

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Gln Gly Tyr
        35

<210> SEQ ID NO 380
<211> LENGTH: 38
<212> TYPE: PRT
<213> ORGANISM: Artificial Sequence
<220> FEATURE:
<223> OTHER INFORMATION: Designed polypeptide

<400> SEQUENCE: 380

Gly Cys Arg Phe Ala Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Gly Pro Gln Gly Tyr
        35

<210> SEQ ID NO 381
<211> LENGTH: 38
<212> TYPE: PRT
<213> ORGANISM: Artificial Sequence
<220> FEATURE:
<223> OTHER INFORMATION: Designed polypeptide

<400> SEQUENCE: 381

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Asn
            20                  25                  30

Ile Gly Pro Asn Gly Tyr
        35

<210> SEQ ID NO 382
<211> LENGTH: 38
<212> TYPE: PRT
<213> ORGANISM: Artificial Sequence
<220> FEATURE:
<223> OTHER INFORMATION: Designed polypeptide

<400> SEQUENCE: 382

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Gly Pro Gln Gly Tyr
        35

<210> SEQ ID NO 383
<211> LENGTH: 38
<212> TYPE: PRT
<213> ORGANISM: Artificial Sequence
<220> FEATURE:
<223> OTHER INFORMATION: Designed polypeptide

<400> SEQUENCE: 383

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Asn
            20                  25                  30

Ile Ser Pro Asn Gly Tyr
            35

<210> SEQ ID NO 384
<211> LENGTH: 38
<212> TYPE: PRT
<213> ORGANISM: Artificial Sequence
<220> FEATURE:
<223> OTHER INFORMATION: Designed polypeptide

<400> SEQUENCE: 384

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Val Ser Pro Asn Gly Tyr
            35

<210> SEQ ID NO 385
<211> LENGTH: 38
<212> TYPE: PRT
<213> ORGANISM: Artificial Sequence
<220> FEATURE:
<223> OTHER INFORMATION: Designed polypeptide

<400> SEQUENCE: 385

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Val Ser Pro Asn Gly Tyr
            35

<210> SEQ ID NO 386
<211> LENGTH: 38
<212> TYPE: PRT
<213> ORGANISM: Artificial Sequence
<220> FEATURE:
<223> OTHER INFORMATION: Designed polypeptide

<400> SEQUENCE: 386

Gly Cys Arg Phe Gly Thr Cys Thr Val Gln Arg Leu Ala Asn Phe Leu
1               5                   10                  15

Tyr Gln Phe Thr Asp Lys Asp Lys Asp Asn Val Ala Pro Arg Thr Asn
            20                  25                  30

Val Gly Pro Gln Gly Tyr
            35

<210> SEQ ID NO 387
<211> LENGTH: 38
<212> TYPE: PRT
<213> ORGANISM: Artificial Sequence
<220> FEATURE:
<223> OTHER INFORMATION: Designed polypeptide -continued

<400> SEQUENCE: 387

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Gly Pro Gln Gly Tyr
            35

<210> SEQ ID NO 388
<211> LENGTH: 38
<212> TYPE: PRT
<213> ORGANISM: Artificial Sequence
<220> FEATURE:
<223> OTHER INFORMATION: Designed polypeptide

<400> SEQUENCE: 388

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Asn
            20                  25                  30

Ile Gly Pro Gln Gly Tyr
            35

<210> SEQ ID NO 389
<211> LENGTH: 38
<212> TYPE: PRT
<213> ORGANISM: Artificial Sequence
<220> FEATURE:
<223> OTHER INFORMATION: Designed polypeptide

<400> SEQUENCE: 389

Lys Cys Asn Phe Ala Thr Cys Ala Thr Gln Arg Leu Ala Asn Phe Leu
1               5                   10                  15

Val Gln Phe Thr Asp Lys Asp Lys Asp Asn Val Ala Pro Arg Ser Lys
            20                  25                  30

Ile Gly Pro Gln Gly Tyr
            35

<210> SEQ ID NO 390
<211> LENGTH: 38
<212> TYPE: PRT
<213> ORGANISM: Artificial Sequence
<220> FEATURE:
<223> OTHER INFORMATION: Designed polypeptide

<400> SEQUENCE: 390

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Ile Gly Pro Gln Gly Tyr
            35

<210> SEQ ID NO 391
<211> LENGTH: 38
<212> TYPE: PRT
<213> ORGANISM: Artificial Sequence
<220> FEATURE:
<223> OTHER INFORMATION: Designed polypeptide

```
<400> SEQUENCE: 391

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Thr Lys
            20                  25                  30

Ile Gly Pro Gln Gly Tyr
            35

<210> SEQ ID NO 392
<211> LENGTH: 38
<212> TYPE: PRT
<213> ORGANISM: Artificial Sequence
<220> FEATURE:
<223> OTHER INFORMATION: Designed polypeptide

<400> SEQUENCE: 392

Gly Cys Arg Phe Gly Thr Cys Thr Val Gln Arg Leu Ala His Phe Leu
1               5                   10                  15

Tyr Gln Phe Thr Asp Lys Asp Lys Asp Asn Val Ala Pro Arg Thr Lys
            20                  25                  30

Val Gly Pro Gln Gly Tyr
            35

<210> SEQ ID NO 393
<211> LENGTH: 52
<212> TYPE: PRT
<213> ORGANISM: Artificial Sequence
<220> FEATURE:
<223> OTHER INFORMATION: hAM

<400> SEQUENCE: 393

Tyr Arg Gln Ser Met Asn Asn Phe Gln Gly Leu Arg Ser Phe Gly Cys
1               5                   10                  15

Arg Phe Gly Thr Lys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gly Gly Tyr
    50

<210> SEQ ID NO 394
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (11)..(11)
<223> OTHER INFORMATION: Arg can be replaced by Trp or citrulline
<220> FEATURE:
<221> NAME/KEY: MOD_RES
<222> LOCATION: (11)..(11)
<223> OTHER INFORMATION: Citrulline
<220> FEATURE:
```

```
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: MOD_RES
<222> LOCATION: (38)..(38)
<223> OTHER INFORMATION: 4Hyp
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys

<400> SEQUENCE: 394

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 395
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp

<400> SEQUENCE: 395

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35
```

```
<210> SEQ ID NO 396
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp

<400> SEQUENCE: 396

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 397
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
```

<223> OTHER INFORMATION: 4Hyp

<400> SEQUENCE: 397

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 398
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp

<400> SEQUENCE: 398

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 399
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT

```
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 399

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
                20                  25                  30

Ile Ser Pro Gln Gly Tyr
            35

<210> SEQ ID NO 400
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp
<220> FEATURE:
<221> NAME/KEY: DISULFID
<222> LOCATION: (38)..(38)
<223> OTHER INFORMATION: Disulphide bridge

<400> SEQUENCE: 400

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
                20                  25                  30

Ile Ser Pro Gln Gly Tyr
            35

<210> SEQ ID NO 401
<211> LENGTH: 38
<212> TYPE: PRT
<213> ORGANISM: Artificial Sequence
<220> FEATURE:
```

```
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 401

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 402
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 402

Gly Cys Arg Phe Gly Thr Cys Thr Val Gln Arg Leu Ala His Gln Ile
1               5                   10                  15
```

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 403
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (17)..(17)
<223> OTHER INFORMATION: Tyr can be replaced by Trp or His
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 403

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 404
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT

```
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp

<400> SEQUENCE: 404

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 405
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp

<400> SEQUENCE: 405

Gly Cys Arg Phe Gly Thr Cys Thr Val Gln Arg Leu Ala His Gln Ile
1               5                   10                  15
```

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 406
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 406

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 407
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT

```
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Thr, Gln, Pro,
      Met, Ile, His, Phe, Glu, Ala, Arg or Lys
<220> FEATURE:
<221> NAME/KEY: MOD_RES
<222> LOCATION: (38)..(38)
<223> OTHER INFORMATION: 4Hyp

<400> SEQUENCE: 407

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 408
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Ser, Trp, Thr, Gln,
      Pro, Met, Ile, His, Phe, Glu, Ala, Arg, Cys or Lys
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp
```

<400> SEQUENCE: 408

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 409
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (4)..(4)
<223> OTHER INFORMATION: Phe can be replaced by Tyr, Trp, Thr, Met, Ile,
      Ala or Cys
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 409

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 410
<211> LENGTH: 38
<212> TYPE: PRT
<213> ORGANISM: Artificial Sequence
<220> FEATURE:
<223> OTHER INFORMATION: hAM15 52 analogue or a pharmaceutically
      acceptable salt
<220> FEATURE:
<221> NAME/KEY: DISULFID
<222> LOCATION: (2)..(7)
<223> OTHER INFORMATION: Disulphide bridge

```
-continued

<220> FEATURE:
<221> NAME/KEY: VARIANT
<222> LOCATION: (4)..(4)
<223> OTHER INFORMATION: Phe can be replaced by Trp, Met, Ile or Cys
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: VARIANT
<222> LOCATION: (17)..(17)
<223> OTHER INFORMATION: Tyr can be replaced by Trp, Thr, Gln, Met, Ile,
      His, Phe, Ala, Arg or Lys
<220> FEATURE:
<221> NAME/KEY: VARIANT
<222> LOCATION: (37)..(37)
<223> OTHER INFORMATION: Gly can be replaced by Tyr, Trp, Pro, His or
      Phe
<220> FEATURE:
<221> NAME/KEY: VARIANT
<222> LOCATION: (38)..(38)
<223> OTHER INFORMATION: Tyr can be replaced by Hyp, Trp, Met or Phe
<220> FEATURE:
<221> NAME/KEY: MOD_RES
<222> LOCATION: (38)..(38)
<223> OTHER INFORMATION: 4Hyp

<400> SEQUENCE: 410

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
            35

<210> SEQ ID NO 411
<211> LENGTH: 38
<212> TYPE: PRT
<213> ORGANISM: Artificial Sequence
<220> FEATURE:
<223> OTHER INFORMATION: hAM
<220> FEATURE:
<221> NAME/KEY: DISULFID
<222> LOCATION: (2)..(7)
<223> OTHER INFORMATION: Disulphide bridge
<220> FEATURE:
<221> NAME/KEY: VARIANT
<222> LOCATION: (11)..(11)
<223> OTHER INFORMATION: Arg can be replaced by Trp or Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: MOD_RES
<222> LOCATION: (38)..(38)
<223> OTHER INFORMATION: 4Hyp

<400> SEQUENCE: 411

Gly Cys Arg Phe Gly Thr Cys Thr Val Gln Arg Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Xaa
            35
```